(12) United States Patent
Knight et al.

(10) Patent No.: US 10,363,558 B2
(45) Date of Patent: Jul. 30, 2019

(54) SYSTEM AND METHOD FOR SERIAL PROCESSING OF MULTIPLE NUCLEIC ACID ASSAYS

(71) Applicant: Canon U.S. Life Sciences, Inc., Rockville, MD (US)

(72) Inventors: Ivor T. Knight, Arlington, VA (US); Kenton C. Hasson, Germantown, MD (US); Johnathan S. Coursey, Germantown, MD (US); Hongye Liang, Clarksville, MD (US); Sami Kanderian, Germantown, MD (US); Gregory H. Owen, Clarksburg, MD (US); Weidong Cao, N. Potomac, MD (US); Ying-Xin Wang, Rockville, MD (US); Scott Corey, Hydes, MD (US); Ben Lane, Hydes, MD (US); Conrad Laskowski, Baltimore, MD (US); Alex Flamm, Baltimore, MD (US); Brian Murphy, Baltimore, MD (US); Eric Schneider, Catonsville, MD (US); Takayoshi Hanagata, Newport News, VA (US); Hiroshi Inoue, Rockville, MD (US); Shulin Zeng, Gaithersburg, MD (US); Brian Bean, Baltimore, MD (US); Franklin Regan, Baltimore, MD (US)

(73) Assignee: Canon U.S. Life Sciences, Inc., Rockville, MD (US)

( * ) Notice: Subject to any disclaimer, the term of this patent is extended or adjusted under 35 U.S.C. 154(b) by 0 days.

(21) Appl. No.: 14/833,939

(22) Filed: Aug. 24, 2015

(65) Prior Publication Data
US 2016/0051985 A1 Feb. 25, 2016

Related U.S. Application Data

(62) Division of application No. 13/223,290, filed on Aug. 31, 2011, now Pat. No. 9,114,399.
(Continued)

(51) Int. Cl.
*B01L 3/00* (2006.01)
*B01L 7/00* (2006.01)
(Continued)

(52) U.S. Cl.
CPC ... *B01L 3/502746* (2013.01); *B01L 3/502784* (2013.01); *B01L 7/52* (2013.01);
(Continued)

(58) Field of Classification Search
CPC ......... B01L 3/502746; B01L 3/502784; B01L 7/52; B01L 7/525; B01L 2200/025;
(Continued)

(56) References Cited

U.S. PATENT DOCUMENTS

| 5,019,699 A | 5/1991 | Koenck |
| 6,086,825 A | 7/2000 | Sundberg et al. |

(Continued)

FOREIGN PATENT DOCUMENTS

| JP | 2002-523781 A | 7/2002 |
| WO | 2004/063731 A1 | 7/2004 |

(Continued)

*Primary Examiner* — Benjamin R Whatley
(74) *Attorney, Agent, or Firm* — Rothwell, Figg, Ernst & Manbeck, P.C.

(57) ABSTRACT

The present invention relates to systems and methods for the real time processing of nucleic acid during polymerase chain reaction (PCR) and thermal melt applications. According to an aspect of the invention, a system for the rapid serial processing of multiple nucleic acid assays is provided. In one embodiment, the system includes, but is not limited to: a microfluidic cartridge having microfluidic (flow-through)

(Continued)

channels, a fluorescence imaging system, a temperature measurement and control system; a pressure measurement and control system for applying variable pneumatic pressures to the microfluidic cartridge; a storage device for holding multiple reagents (e.g., a well-plate); a liquid handling system comprising at least one robotic pipettor for aspirating, mixing, and dispensing reagent mixtures to the microfluidic cartridge; systems for data storage, processing, and output; and a system controller to coordinate the various devices and functions.

22 Claims, 41 Drawing Sheets

Related U.S. Application Data

(60) Provisional application No. 61/378,824, filed on Aug. 31, 2010, provisional application No. 61/378,722, filed on Aug. 31, 2010, provisional application No. 61/378,543, filed on Aug. 31, 2010, provisional application No. 61/378,471, filed on Aug. 31, 2010, provisional application No. 61/378,558, filed on Aug. 31, 2010, provisional application No. 61/378,467, filed on Aug. 31, 2010, provisional application No. 61/378,591, filed on Aug. 31, 2010, provisional application No. 61/378,700, filed on Aug. 31, 2010.

(51) Int. Cl.
　　*G01N 21/77*　　(2006.01)
　　*C12Q 1/686*　　(2018.01)
　　*G01N 35/08*　　(2006.01)
　　*G01N 35/10*　　(2006.01)

(52) U.S. Cl.
　　CPC .............. *B01L 7/525* (2013.01); *C12Q 1/686* (2013.01); *G01N 21/77* (2013.01); *G01N 35/08* (2013.01); *G01N 35/1095* (2013.01); *B01L 2200/025* (2013.01); *B01L 2200/027* (2013.01); *B01L 2200/028* (2013.01); *B01L 2200/10* (2013.01); *B01L 2300/0663* (2013.01); *B01L 2300/0816* (2013.01); *B01L 2300/1822* (2013.01); *B01L 2300/1827* (2013.01); *B01L 2300/1844* (2013.01); *B01L 2400/0487* (2013.01); *G01N 2021/7786* (2013.01)

(58) Field of Classification Search
　　CPC ......... B01L 2200/027; B01L 2200/028; B01L 2200/10; B01L 2300/0663; B01L 2300/0816; B01L 2300/1822; B01L 2300/1827; B01L 2300/1844; B01L 2400/0487; C12Q 1/686; G01N 21/77; G01N 35/08; G01N 35/1095; G01N 2021/7786
　　See application file for complete search history.

(56) References Cited

U.S. PATENT DOCUMENTS

| | | | |
|---|---|---|---|
| 6,820,979 B1 * | 11/2004 | Stark | A61B 3/112 351/206 |
| 6,827,095 B2 * | 12/2004 | O'Connor | B01F 5/064 137/15.01 |
| 7,097,974 B1 | 8/2006 | Stähler et al. | |
| 7,593,560 B2 | 9/2009 | Hasson | |
| 7,629,124 B2 | 12/2009 | Hasson et al. | |
| 7,906,319 B2 | 3/2011 | Hasson et al. | |
| 2005/0277125 A1 * | 12/2005 | Benn | B01J 19/0046 435/6.11 |
| 2006/0073484 A1 | 4/2006 | Mathies et al. | |
| 2006/0166373 A1 | 7/2006 | Enoki et al. | |
| 2007/0026421 A1 | 2/2007 | Sundberg et al. | |
| 2007/0231799 A1 | 10/2007 | Knight et al. | |
| 2008/0003588 A1 | 1/2008 | Hasson et al. | |
| 2008/0003593 A1 | 1/2008 | Hasson et al. | |
| 2008/0003594 A1 * | 1/2008 | Hasson | B01L 7/52 435/6.16 |
| 2008/0014576 A1 * | 1/2008 | Jovanovich | B01L 11/0071 435/5 |
| 2008/0014589 A1 | 1/2008 | Link et al. | |
| 2008/0038163 A1 | 2/2008 | Boege et al. | |
| 2008/0176230 A1 | 7/2008 | Owen et al. | |
| 2009/0022625 A1 | 1/2009 | Lee et al. | |
| 2009/0047713 A1 * | 2/2009 | Handique | B01L 3/502707 435/91.2 |
| 2009/0060795 A1 * | 3/2009 | Owen | B01L 7/525 422/400 |
| 2009/0061489 A1 | 3/2009 | Hanagata et al. | |
| 2009/0130745 A1 | 3/2009 | Williams et al. | |
| 2009/0084530 A1 | 4/2009 | Shuy | |
| 2009/0112481 A1 | 4/2009 | Cao | |
| 2009/0112484 A1 | 4/2009 | Boles et al. | |
| 2009/0143233 A1 | 6/2009 | Knight et al. | |
| 2009/0148858 A1 * | 6/2009 | Patel | B01L 3/50273 435/7.1 |
| 2009/0248349 A1 | 10/2009 | Hasson et al. | |
| 2009/0318306 A1 | 12/2009 | Hasson et al. | |
| 2009/0320930 A1 | 12/2009 | Zeng et al. | |
| 2009/0325159 A1 | 12/2009 | Zeng | |
| 2010/0021910 A1 * | 1/2010 | Cao | B01L 3/502753 435/6.11 |
| 2010/0170799 A1 | 7/2010 | Amirkhanian et al. | |
| 2011/0008223 A1 * | 1/2011 | Tsao | B01L 3/502715 422/502 |
| 2011/0010103 A1 | 1/2011 | Kanderian | |
| 2011/0048547 A1 | 3/2011 | Hasson et al. | |
| 2011/0056926 A1 | 3/2011 | Coursey | |
| 2011/0077897 A1 | 3/2011 | Hasson et al. | |
| 2011/0091877 A1 | 4/2011 | Murphy et al. | |
| 2011/0269239 A1 | 11/2011 | Diessel et al. | |
| 2013/0040376 A1 | 2/2013 | Amshey et al. | |
| 2013/0260447 A1 * | 10/2013 | Link | G01N 1/38 435/287.2 |
| 2014/0073043 A1 | 3/2014 | Holmes | |
| 2014/0234949 A1 | 8/2014 | Wasson et al. | |

FOREIGN PATENT DOCUMENTS

| | | |
|---|---|---|
| WO | 2009/051416 A1 | 4/2009 |
| WO | 2010/037497 A1 | 4/2010 |
| WO | 2010/118430 A1 | 10/2010 |

* cited by examiner

SYSTEM AND METHOD FOR SERIAL PROCESSING OF MULTIPLE NUCLEIC ACID ASSAYS

CROSS-REFERENCE TO RELATED APPLICATION

This application is a divisional of U.S. application Ser. No. 13/223,290, filed on Aug. 31, 2011, which claims the benefit of priority to U.S. Provisional Application Nos. 61/378,824, filed Aug. 31, 2010; 61/378,722, filed Aug. 31, 2010; 61/378,543, filed Aug. 31, 2010; 61/378,471, filed Aug. 31, 2010; 61/378,558, filed Aug. 31, 2010; 61/378,467, filed Aug. 31, 2010; 61/378,591, filed Aug. 31, 2010; and 61/378,700, filed Aug. 31, 2010, the entire respective disclosures of which are hereby incorporated by reference.

BACKGROUND

Field of the Invention

The present invention relates generally to systems and methods for the rapid serial processing of multiple nucleic acid assays. More particularly, the present invention provides for the real time processing of nucleic acid during polymerase chain reaction (PCR) and thermal melt applications.

Description of the Background

The detection of nucleic acids is central to medicine, forensic science, industrial processing, crop and animal breeding, and many other fields. The ability to detect disease conditions (e.g., cancer), infectious organisms (e.g., HIV), genetic lineage, genetic markers, and the like, is ubiquitous technology for disease diagnosis and prognosis, marker assisted selection, identification of crime scene features, the ability to propagate industrial organisms and many other techniques. Determination of the integrity of a nucleic acid of interest can be relevant to the pathology of an infection or cancer.

One of the most powerful and basic technologies to detect small quantities of nucleic acids is to replicate some or all of a nucleic acid sequence many times, and then analyze the amplification products. PCR is a well-known technique for amplifying deoxyribonucleic acid (DNA). With PCR, one can produce millions of copies of DNA starting from a single template DNA molecule. PCR includes phases of "denaturation," "annealing," and "extension." These phases are part of a cycle which is repeated a number of times so that at the end of the process there are enough copies to be detected and analyzed. For general details concerning PCR, see Sambrook and Russell, Molecular Cloning—A Laboratory Manual (3rd Ed.), Vols. 1-3, Cold Spring Harbor Laboratory, Cold Spring Harbor, N.Y. (2000); Current Protocols in Molecular Biology, F. M. Ausubel et al., eds., Current Protocols, a joint venture between Greene Publishing Associates, Inc. and John Wiley & Sons, Inc., (supplemented through 2005) and PCR Protocols A Guide to Methods and Applications, M. A. Innis et al., eds., Academic Press Inc. San Diego, Calif. (1990).

The PCR process phases of denaturing, annealing, and extension occur at different temperatures and cause target DNA molecule samples to replicate themselves. Temperature cycling (thermocyling) requirements vary with particular nucleic acid samples and assays. In the denaturing phase, a double stranded DNA (dsDNA) is thermally separated into single stranded DNA (ssDNA). During the annealing phase, primers are attached to the single stranded DNA molecules. Single stranded DNA molecules grow to double stranded DNA again in the extension phase through specific bindings between nucleotides in the PCR solution and the single stranded DNA. Typical temperatures are 95° C. for denaturing, 55° C. for annealing, and 72° C. for extension. The temperature is held at each phase for a certain amount of time which may be a fraction of a second up to a few tens of seconds. The DNA is doubled at each cycle, and it generally takes 20 to 40 cycles to produce enough DNA for certain applications. To have good yield of target product, one has to accurately control the sample temperatures at the different phases to a specified degree.

Typical existing instruments for performing nucleic acid assays with PCR operate in a batch mode. Samples to be tested are mixed with assay reagents, and then typically loaded manually into the PCR instrument. A single sequence of amplification and analysis are run on that batch. If a replicate or modified assay is desired, a new batch must be prepared and run, which can be a time consuming and labor intensive task. Thus, there remains a need in the art for more efficient systems and methods of for performing nucleic acid assays.

The present invention changes that paradigm by providing the ability to perform rapid serial multiplex assays, on several samples simultaneously.

SUMMARY

The present invention relates to systems and methods for the rapid serial processing of multiple nucleic acid assays and, more particularly, provides for the real time processing of nucleic acid during PCR and thermal melt applications.

In one aspect, the present invention provides a system for rapid serial processing of nucleic acid assays. In a particular embodiment, the invention can include a microfluidic cartridge (also referred to herein as a microfluidic device) having at least one flow-through channel; an optical system (which can be a fluorescence imaging system); a temperature measurement and control system; a pressure measurement and control system for applying variable pneumatic pressures to the microfluidic cartridge; a storage device for holding multiple reagents, such as a well-plate; a liquid handling system comprising at least one robotic pipettor for aspirating, mixing, and dispensing reagent mixtures to the microfluidic cartridge; means for data storage, processing, and output; and a system controller to coordinate the various devices and functions.

In other embodiments, the fluorescence imaging system provides information on the position of a material within a microfluidic channel, and that information is used to control flow in that channel. In other embodiments, a sequence of alternating test and spacer slugs are created in the microfluidic cartridge. In other embodiments, the spacer slugs have a property that makes the spacer slug distinguishable from the test slug. In other embodiments, the robotic pipettor is used to mix a solution comprising nucleic acid with a solution comprising a locus-specific reagent. In other embodiments, the robotic pipettor is used to mix a solution comprising nucleic acid with a solution comprising an enzyme. In other embodiments, PCR amplification and melt analysis are performed on samples in the microfluidic cartridge. In other embodiments, the liquid handling system includes a means for removing excess liquid from the outside of the pipette tip. In other embodiments, the liquid handling system includes a means for automatically discarding and replacing pipette tips. In other embodiments, the microfluidic cartridge includes a means for reversibly docking with at least one pipette tip. In other embodiments, the topology of the channels in the microfluidic cartridge is a T shape. In other embodiments, the fluids are moved through the microfluidic channels in a stop and go pattern. In other embodiments, the results of one or more tests are used by the system.

Aspects of the invention are embodied in a system for serial processing of nucleic acid assays. The system comprises a microfluidic cartridge, a flow control module, a temperature measurement and control system, and a fluorescence imaging system. The microfluidic cartridge comprises an interface chip having at least one inlet port and microfluidic channel and a reaction chip having at least one microfluidic channel in fluid communication with an associated microfluidic channel of the interface chip. The flow control module is configured to control assay fluid flow through the at least one microfluidic channel and to selectively apply pneumatic pressures to the at least one microfluidic channel of the interface chip and the reaction chip. The flow control module configured to: (a) draw a first fluid into the microfluidic channel of the interface chip via the inlet port of the interface chip, (b) create a first fluid segment in the microfluidic channel of the reaction chip by drawing the first fluid from the associated microfluidic channel of the interface chip into the microfluidic channel of the reaction chip, (c) draw a second fluid into the microfluidic channel of the interface chip via the inlet port of the interface chip, and (d) create a second fluid segment in the microfluidic channel of the reaction chip by drawing the second fluid from the associated microfluidic channel of the interface chip into the microfluidic channel of the reaction chip. The temperature measurement and control system configured to control and measure a temperature of one or more portions of the at least microfluidic channel of the reaction chip. The fluorescence imaging system comprises one or more excitation elements and an imaging sensor and is configured to create images of fluorescent emissions from materials within the at least one microfluidic channel of the reaction chip.

In one embodiment, the fluorescence imaging system comprises a sensor element configured to generate a storable image of at least a portion of the microfluidic channel of the reaction chip, and a plurality of illumination elements disposed with respect to the sensor element and configured to illuminate a portion of the reaction chip to be imaged by the sensor element.

In another embodiment at least one of the illumination elements comprises an illumination assembly comprising an LED, a mask disposed in front of the LED and having an opening formed therein so as to control an area illuminated by the illumination assembly, a filter along an optic path of the illumination assembly for controlling the spectral content of light emitted by the illumination assembly, and a lens for imaging an area with light emitted by the illumination assembly, wherein the LED, the mask, the filter, and the lens are aligned along an optic axis of the illumination assembly. It is noted that the optic axis may continue behind the lens, particularly so that in one embodiment the filter can be placed on either side of the lens, depending on the specific conditions desired for the application.

In another embodiment, at least two of the illumination elements are configured to illuminate different portions of the reaction chip.

In another embodiment, the sensor element comprises a digital single lens reflex camera.

In another embodiment, each of the illumination elements comprises an LED.

In another embodiment, the fluorescence imaging system comprises four illumination elements disposed at 90-degree angular increments about the sensor element.

In another embodiment, the sensor element comprises a CMOS sensor.

In another embodiment, the sensor element includes a pixel array, and the system further comprises logic elements configured to detect an image of only a portion of the pixels of the pixel array.

In another embodiment, the sensor element is configured to generate multiple images.

In another embodiment, the sensor element is configured to generate an image having a JPEG format.

In another embodiment, the fluorescence imaging system comprises at least one extension tube between the sensor and the microfluidic channel of the reaction chip.

In another embodiment, the fluorescence imaging system further comprises an emission filter positioned between the sensor and the microfluidic channel of the reaction chip that is configured to allow light signals of only a selected wavelength to reach the sensor.

In another embodiment, the microfluidic channel of the reaction chip comprises a first zone and a second zone, and a first one of the LEDs is positioned and oriented to illuminate the second zone, a second and a third of the LEDs are spaced 180-degrees from each other and are disposed on opposed sides of the sensor and are positioned and oriented to illuminate the first zone, and a fourth one of the LEDs is positioned and oriented to illuminate both the first zone and the second zone.

In another embodiment, the system further comprises a liquid handling system comprising at least one pipettor configured to be accessible to the inlet port of the interface chip and configured to aspirate sample (which may include DNA material) and reagent fluids, mix the fluids, and dispense a mixture of sample and reagent fluids to the inlet port of the interface chip.

In another embodiment, the pipettor is configured to (a) draw a first volume of a first fluid into the pipettor, (b) draw a second volume of a second fluid into the pipettor, (c) expel a droplet including the first and second fluids from the pipettor without releasing the droplet from the pipettor, wherein a volume of the droplet is greater than half the sum of the first and second volumes, (d) draw the droplet back into the pipettor, and (e) repeat steps (c) and (d) at least one time before dispensing a mixture of the first and second fluids to the inlet port of the interface chip.

In another embodiment, the pipettor includes at least one pipette tip having a docking feature configured facilitate automatic alignment of the pipette tip with the inlet port of the interface chip.

In another embodiment, the inlet port of the interface chip includes a docking receptacle configured for cooperative engagement with the docking feature of the pipette tip to align the pipette tip with the inlet port In another embodiment, the pipettor is configured to engage the docking feature of the pipette tip containing the fluid mixture with the docking receptacle of the inlet port of the interface chip, and produce a bead of the fluid mixture that makes contact with the microfluidic channel of the interface chip while the flow control module pulls at least a portion of the fluid in the bead into the microfluidic channel of the microfluidic chip, wherein the docking feature and the docking receptacle are configured to position the pipette tip with respect to the inlet port such that the proximity of the pipette tip and the microfluidic channel allows a portion of the bead to contact the microfluidic channel while remaining attached to the pipette tip, and disengage the docking feature of the pipette tip from the docking receptacle of the inlet port of the interface chip while removing the bead from contact with the microfluidic channel of the interface chip, leaving fluid only inside the microfluidic channel and not in the inlet port of the interface chip. In another embodiment, the interface chip includes a plurality of inlet ports and a microfluidic channel associated with each inlet port and the reaction chip includes a plurality of microfluidic channels, each in fluid communication with an associated microfluidic channel of the interface chip, and wherein the pipettor is configured to simultaneously dispense a mixture of reagent fluids to two or more of the inlet ports of the interface chip.

In another embodiment, the flow control module comprises a first pumping system and a second pumping system, wherein the first pumping system is configured to control movement of fluid in the microfluidic channel of the interface chip, and the second pumping system is configured to control movement of fluid in the microfluidic channel of the reaction chip.

In another embodiment, the system further comprises a system controller in communication with the flow control module, the temperature measurement and control system, and the fluorescence imaging system, is configured transmit control signals to control operation of the flow control module, the temperature measurement and control system, and the fluorescence imaging system.

Other aspects of the invention are embodied in an instrument for serial processing of multiple nucleic acid assays. The system comprises a frame chassis, a processing drawer, a cooling manifold assembly, a liquid handling system, an optical imaging system. The processing drawer is configured to be moveable relative to the frame chassis between an open position and a closed position and includes a microfluidic device support structure configured to hold a microfluidic device. The cooling manifold assembly is carried on a portion of said frame chassis adjacent the processing drawer and is configured to be in an operative position with respect to the microfluidic device support structure when the processing drawer is in the closed position. The liquid handling system is supported by the frame chassis and is configured such that a microfluidic device mounted on the microfluidic device support structure is accessible to the liquid handling system when the processing drawer is in the closed position. The optical imaging system is configured to create images of fluorescent emissions from materials within a microfluidic channel of a microfluidic device. The optical imaging system is carried on a portion of the frame chassis adjacent the processing drawer and is configured to be in an operative position with respect to the microfluidic device support structure when the processing drawer is in the closed position.

In another embodiment, the cooling manifold assembly is positioned above the processing drawer.

In another embodiment, the optical imaging system is positioned below the processing drawer.

In another embodiment, the liquid handling system comprises at least one robotic pipettor supported by the frame chassis and configured for automated x, y, and z movement.

In another embodiment, the instrument further comprises a pipette tip loading and cleaning mechanism supported on a pipette tip loading and cleaning mechanism support structure of the processing drawer. The pipette tip loading and cleaning mechanism includes racks configured to removably hold a plurality pipette tips in positions that are accessible to the robotic pipettor when the processing drawer is in the closed position.

In another embodiment, the instrument further comprises a container support surface on said processing drawing that is configured to support a fluid container in a position accessible to the liquid handling system when the processing drawer is in the closed position.

In another embodiment, the instrument further comprises a removable tray configured to be removably supported on the processing drawer, wherein the container support surface and microfluidic device support structure are located on the removable tray.

In another embodiment, the instrument further comprises a microfluidic device supported on the microfluidic device support structure of the processing drawer, the microfluidic device comprising an interface chip having at least one inlet port and microfluidic channel and a reaction chip having at least one microfluidic channel in fluid communication with an associated microfluidic channel of the interface chip.

In another embodiment, the reaction chip comprises a plurality of microchannels, a plurality of resistive temperature detectors (RTDs) each adjacent to a portion of an associated one of the plurality of microchannels, a plurality of individual heater electrodes, each connected to an associated one of the plurality of RTDs, a first common electrode connected to each of the plurality of RTDs, a second common electrode connected the first common electrode and to each of the plurality of RTDs, and a heater control and measurement circuit configured to: (i) drive the plurality of RTDs with heater control signals transmitted to each RTD via the associated individual heater electrode, and (ii) sense a temperature of each of the plurality of RTDs.

In another embodiment, the instrument further comprises a multi-well tray supported on the container support surface on the processing drawer.

In another embodiment, the cooling manifold assembly is configured to direct airflow to a microfluidic device supported on the microfluidic device support structure while isolating the airflow from one or more inlet ports of the microfluidic device. In one embodiment, the cooling manifold assembly comprises an air inlet configured to receive the airflow, an air outlet, an inlet duct configured to direct the airflow from the air inlet to a portion of the microfluidic device, and an outlet duct configured to direct the airflow from the microfluidic device to the air outlet.

In another embodiment, the cooling manifold assembly comprises a bi-level cooling manifold for cooling a microfluidic device having one or more inlet ports. In one embodiment, the cooling manifold comprises a first duct and a second duct. The first duct comprises an upper confinement channel, and a vertical channel connected to the upper confinement channel. The second duct comprises a lower confinement channel, wherein at least a portion of the lower confinement channel is beneath the upper confinement channel, and an opening. The cooling manifold is configured to isolate airflow in the first and second ducts from one or more inlet ports of the microfluidic device.

In another embodiment, instrument further includes one or more gaskets disposed between the cooling manifold and the microfluidic device, each gasket being configured to provide a seal between the cooling manifold and the microfluidic device to substantially keep cooling air flowing in the cooling manifold from impinging on selected portions of the microfluidic device.

Further applications and advantages of various embodiments of the present invention are discussed below with reference to the drawing figures.

DETAILED DESCRIPTION OF PREFERRED EMBODIMENTS

While the present invention may be embodied in many different forms, a number of illustrative embodiments are described herein with the understanding that the present disclosure is to be considered as providing examples of the principles of the invention and such examples are not intended to limit the invention to the embodiments shown or described herein.

According to an aspect of the present invention, a system for the rapid serial processing of multiple nucleic acid assays is provided. In one embodiment, the system includes, but is not limited to: a microfluidic cartridge having microfluidic (flow-through) channels, an optical system, a temperature measurement and control system; a pressure measurement and control system for applying variable pneumatic pressures to the microfluidic cartridge; a storage device for holding multiple reagents (e.g., a well-plate); a liquid handling system comprising at least one robotic pipettor (e.g., micropipettor) for aspirating, mixing, and dispensing sample/reagent mixtures to the microfluidic cartridge; systems for data storage, processing, and output; and a system controller to coordinate the various devices and functions. These components and their configuration are described in greater detail below.

Exemplary systems for performing nucleic acid diagnostic assays with a microfluidic cartridge are described in U.S. Patent Application Publication No. 2008/0176230, "Systems And Methods For Real-Time PCR" and U.S. Pat. No. 7,629,124 "Real-Time PCR In Micro-Channels," the respective disclosures of which are hereby incorporated by reference.

Figure 1A:
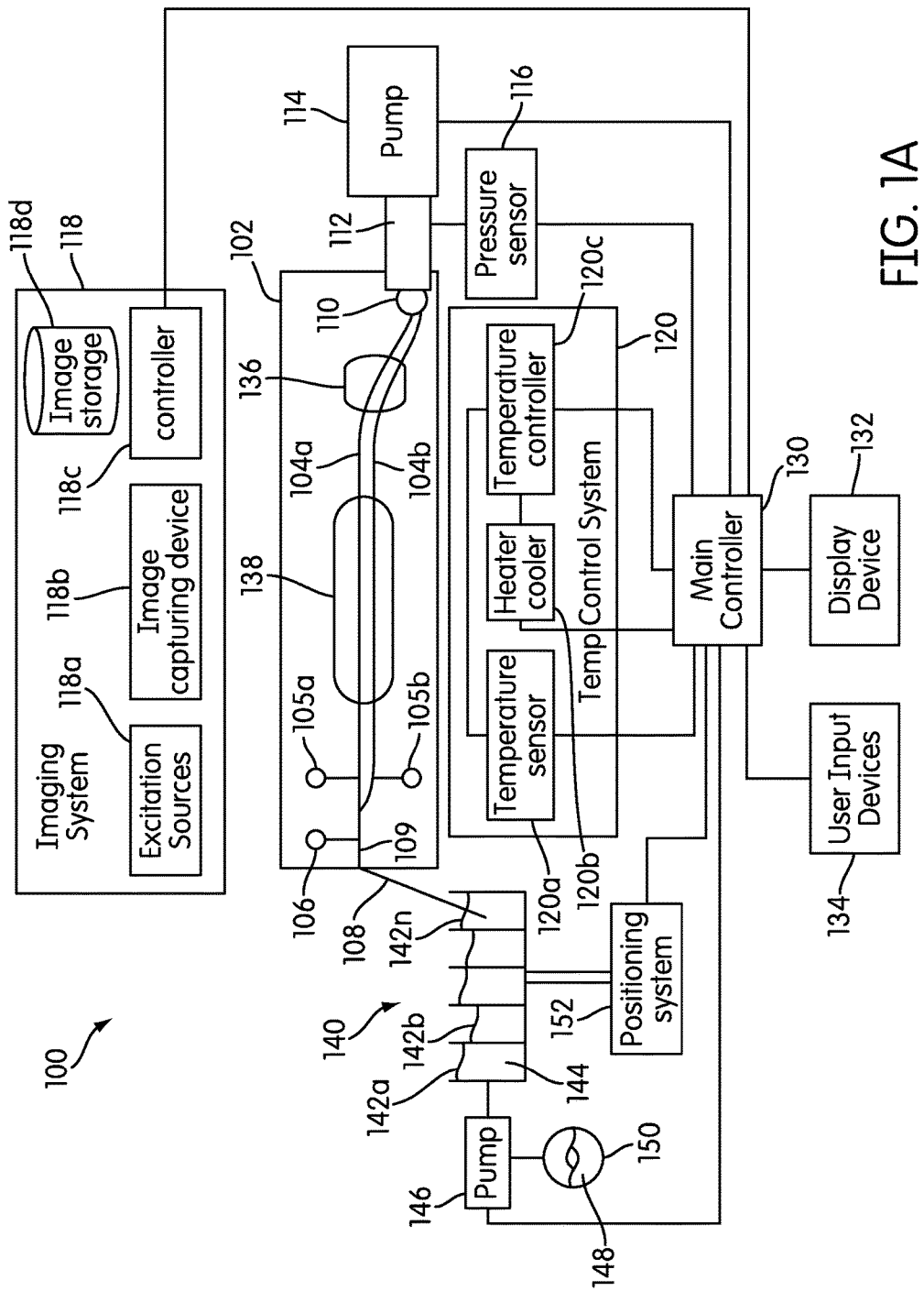
FIGS. 1A and 1B are block diagrams illustrating features of a system that may be implemented in embodiments of the invention.
Figure 1B:
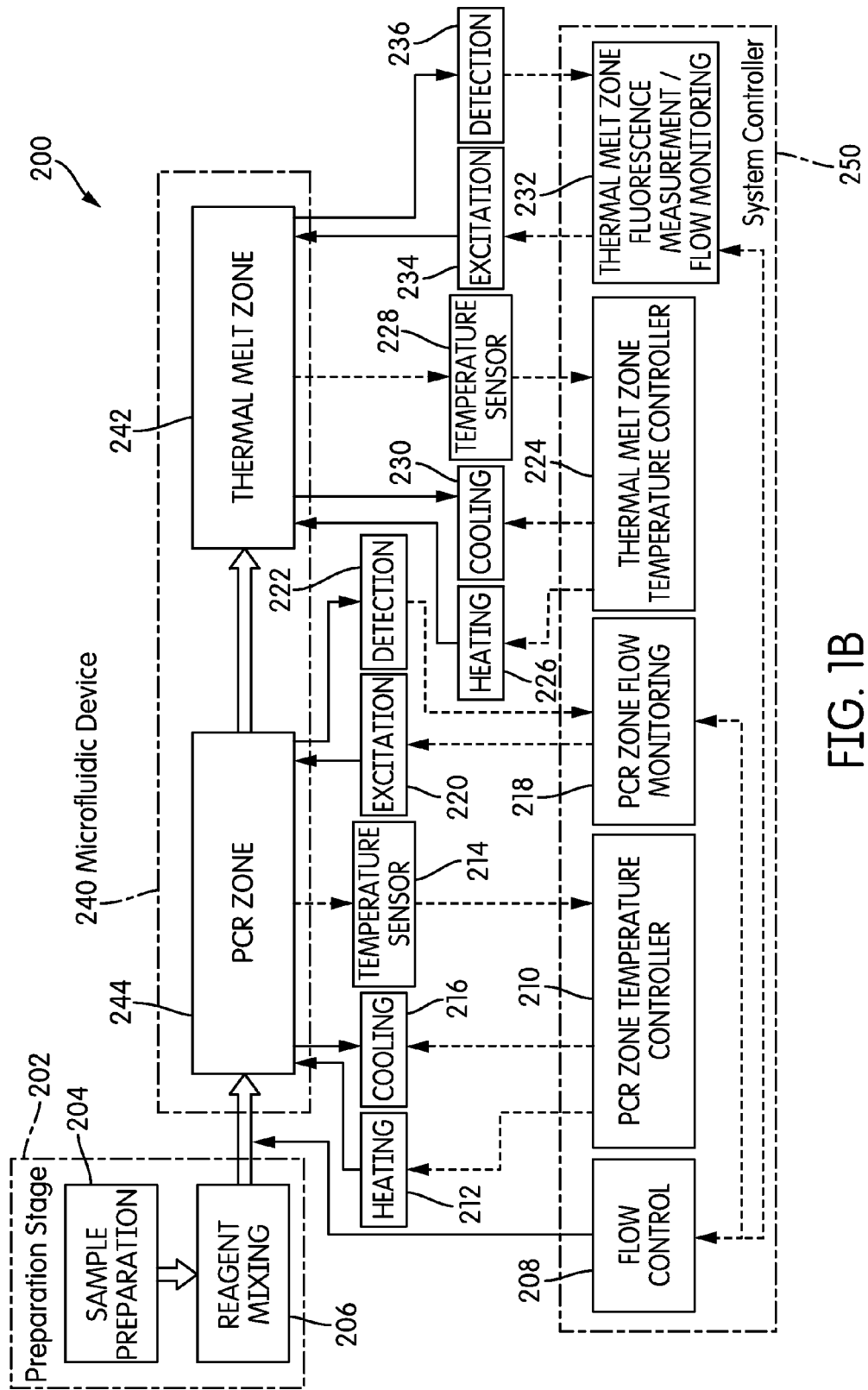

FIGS. 1A and 1B are block diagrams illustrating features of a system for processing of multiple nucleic acid assays that can be configured to embody various aspects of the invention. FIGS. 1A and 1B illustrate features that may be implemented in various combinations to implement a system having the characteristics and functionality preferred for an embodiment of the invention. Neither system shown in FIG. 1A or 1B need necessarily be implemented in its entirety and not all features of the systems shown in FIG. 1A or 1B need necessarily be implemented in a system having the characteristics and functionality preferred for an embodiment of the invention.

System 100 shown in FIG. 1A may include a microfluidic device 102. Microfluidic device 102 may include one or more microfluidic channels 104. In the examples shown, device 102 includes two microfluidic channels, channel 104a and channel 104b. Although only two channels are shown in the exemplary embodiment, it is contemplated that device 102 may have fewer than two or more than two channels. For example, in some embodiments, device 102 includes eight channels 104.

Device 102 may include two DNA processing zones, a DNA amplification zone 138 (a.k.a., PCR zone 138) and a DNA melting zone 136. A DNA sample traveling through the PCR zone 138 may undergo PCR, and a DNA sample passing through melt zone 136 may undergo high resolution thermal melting. As illustrated in FIG. 1A, PCR zone 138 includes a first portion of channels 104 and melt zone 136 includes a second portion of channels 104, which is down stream from the first portion.

Device 102 may also include a sipper 108. Sipper 108 may be in the form of a hollow tube. Sipper 108 has a proximal end that is connected to an inlet 109 which inlet couples the proximal end of sipper 108 to channels 104. Alternatively, or in addition to, the sipper 108, the system 100 may include other means for introducing materials into the device 102, such as, a liquid handling system that may include one or more robotic pipettors having pipette (e.g., micropipette) tips, as described below.

Device 102 may also include one or more common reagent wells 106 which is (are) connected to inlet 109. Device 102 may also include a locus specific reagent well 105 for each channel 104. For example, in the embodiment shown, device 102 includes a locus specific reagent well 105a, which is connected to channel 104a and may include a locus specific reagent well 105b which is connected to channel 104b. Device 102 may also include a waste well 110 for each channel 104.

The solution that is stored in the common reagent well(s) 106 may contain dNTPs, polymerase enzymes, salts, buffers, surface-passivating reagents, one or more non-specific fluorescent DNA detecting molecules, a fluid marker and the like. The solution that is stored in a locus specific reagent well 105 may contain PCR primers, a sequence-specific fluorescent DNA probe or marker, salts, buffers, surface-passivating reagents and the like.

In order to introduce a sample solution into the channels 104, system 100 may include a well plate 140 that includes a plurality of wells 142, at least some of which contain a sample solution (e.g., a solution containing a nucleic acid sample). In the embodiment shown, well plate 140 is connected to a positioning system 152 which is connected to a main controller 130.

Main controller 130 may comprise a programmed computer or other microprocessor, e.g., incorporated on a printed circuit board (PCB), and may be implemented using a PXI-8105 controller which is available from National Instruments Corporation of Austin, Tex. Positioning system 152 may include a positioner (e.g., the MX80 positioner available from Parker Hannifin Corporation of PA ("Parker")) for positioning well plate 140, a stepping drive (e.g., the E-AC Microstepping Drive available from Parker) for driving the positioner, and a controller (e.g., the 6K4 controller available from Parker) for controlling the stepping drive.

In one embodiment, to introduce a sample solution into the channels 104, the positioning system 152 is controlled to well plate 140 such that the distal end of sipper 108 is submerged in the sample solution stored in one of the wells 142. FIG. 1A shows the distal end of sipper 108 being submerged within the sample solution stored in well 142n. In an alternative embodiment, rather than carrying the well plate 140 on a positioning system 152 for moving the plate 140 relative to the stationary microfluidic device 102 to selectively place the sipper tube 108 in different wells 142a, 142b, . . . 142n, both the well plate 140 and the microfluidic device 102 may be held fixed, and the system may include a fluid handling system comprising one or more robotic pipettors configured to move relative to the well plate and the microfluidic device and to move fluids from the well plate to the microfluidic device.

In order to force the sample solution through the channels 104 (and up the sipper 108), a vacuum manifold 112 and pump module 114 (which may comprise one or more individual pumps) may be employed. The vacuum manifold 112 may be operably connected to a portion of device 102 (e.g., at waste well 110), and pump module 114 may be operably connected to manifold 112. Pump module 114 is connected to and controlled by the main controller 130. The system may include a flow control module and a PCR zone flow monitoring module which may comprise components of the main controller 130, or they may be separate components in communication with the main controller 130. A pressure sensor 116 (which may comprise one or more individual sensors) is connected to the manifold 112 (or is otherwise configured to detect system pressure) and to the main controller 130 (e.g., to the flow control module) to provide a feedback loop for controlling the pump module 114. When pump module 114 is activated via a control signal from the main controller 130, pump module 114 creates a pressure differential (e.g., pump module 114 may draw air out of a waste well 110), and this pressure differential causes the sample solution stored in well 142n to flow up sipper 108 and through inlet channel 109 into channels 104. Additionally, this causes the reagents in wells 106 and 105 to flow into a channel. Accordingly, pump module 114 functions to force a sample solution and real-time PCR reagents to flow through channels 104. As illustrated in FIG. 1A, melt zone 136 is located downstream from PCR zone 138. Thus, a sample solution will flow first through the PCR zone and then through the melting zone.

Referring back to well plate 140, well plate 140 may include a buffer solution well 142a. In one embodiment, buffer solution well 142a holds a buffer solution 148. Buffer solution 148 may comprise a conventional PCR buffer, such as a conventional real-time (RT) PCR buffer. Conventional PCR buffers are available from a number of suppliers, including: Bio-Rad Laboratories, Inc., Applied Biosystems, Roche Diagnostics, and others.

In order to replenish buffer solution well 142a with the buffer solution 148, system 100 may include a buffer solution storage container 150 and a pump 146 for pumping the buffer solution 148 from container 150 into well 142a. Additionally, pump 146 may be configured to not only add solution 148 to well 142a, but also remove solution 148 from well 142a, thereby re-circulating the solution 148.

In one configuration, as described in the U.S. Pat. No. 7,629,124, the system includes a test solution reservoir, which as described above, may be a reservoir containing multiple test solutions, such as a multi-well, microtiter plate 140, in which each well contains different test solutions, e.g., test samples. The system further includes a carrier fluid reservoir. In one embodiment, the test solution is substantially the same as the carrier fluid, except that the test solution comprises all the necessary real-time PCR reagents. The real-time PCR reagent mixture may include PCR primers, dNTPs, polymerase enzymes, salts, buffers, surface-passivating agents, and the like. In addition, the real-time PCR mixture may include a non-specific fluorescent DNA detecting molecule, a sequence-specific fluorescent DNA probe or a marker. In an additional embodiment, the carrier fluid is an immiscible fluid (such as an oil, a fluorinated liquid, or any other nonaqueous or hydrophobic solvent). The purpose of the carrier fluid is to deter transfer of material from one test bolus to another. Another purpose of the carrier fluid is to provide a distinguishable transition between boluses that may be used to track the fluid flow in the channel. In one embodiment, the carrier fluid may include a marker.

In one embodiment, the test solution and carrier fluid are introduced into a microchannels 104a, 104b through a switch (not shown) under control of the main controller 130 such that the carrier fluid and the test solution are sequentially, alternately introduced into microchannels 104a, 104b to form discrete boluses of test solution separated from one another by carrier fluid. The volume of the test solution and carrier fluid that is introduced into microchannels 104a, 104b is selected such that there is minimal blending between them during movement through microchannels 104a, 104b.

A multitude of reactions in series (or sequential reactions) can thus be carried out in each of the microchannels 104a, 104b as a result of the continuous movement of boluses of different test solutions through microchannels 104a, 104b, each separated by the carrier fluid. The flow rate of the carrier fluid and test solution boluses through microchannels 104a, 104b is controlled by pump module 114 under control of main controller 130 in order to regulate the flow rate of the test solution boluses and the carrier fluid in microchannels 104a, 104b. The flow rate may be regulated such that a desired number of PCR cycles are performed as the test solution boluses passes through PCR zone 138 of the microchannels 104a, 104b.

In order to achieve PCR for a DNA sample flowing through the PCR zone 138, the temperature of the sample must be cycled, as is well known in the art. Accordingly, in some embodiments, system 100 includes a temperature control system 120. The temperature control system 120 may include a temperature sensor 120a (which may comprise one or more sensors), a heater/cooler 120b (which may comprises one or more heater and/or cooler devices), and a temperature controller 120c, which may comprise a programmed computer or other microprocessor which sends control signals to the heater/cooler and/or receives signals from the temperature sensor. In some embodiments, a temperature control system 120 is interfaced with main controller 130 so that main controller 130 can control the temperature of the samples flowing through the PCR zone and the melting zone. Temperature controller 120c may be part of the main controller 130. Although a single temperature control system 120 is shown for the entire microchip 102, the temperature control system 120 may comprise separate temperature control sub-systems—each comprising, for example, a temperature sensor, a heater/cooler, and a temperature controller—for the PCR zone 138 and the melt zone 136. Specific details of an embodiment of a temperature control system will be described below.

Main controller 130 may be connected to a display device 132 for displaying a graphical user interface. Main controller 130 may also be connected to user input devices 134, which allow a user to input data and commands into main controller 130.

To monitor the PCR process and the melting process that occur in PCR zone 138 and melt zone 136, respectively, system 100 may include an imaging system 118. Imaging system 118 may include an excitation source 118a, an image capturing device 118b, a controller 118c, and an image storage unit 118d. Controller 118c may be part of the main controller 130. An exemplary imaging device is described below.

FIG. 1B illustrates a functional block diagram of a variation of a system 200 for using a microfluidic device 240 (which may correspond to microfluidic device 102 of the system 100 shown in FIG. 1), in accordance with one embodiment. The DNA sample is input in the microfluidic device 240 from a preparation stage 202. As described herein, the preparation stage 202 may also be referred to interchangeably as the pipettor system or liquid handling system. The preparation stage 202 may comprise appropriate devices for preparing the sample 204 and for adding one or more reagents 206 to the sample. Once the sample is input into the microfluidic device 240, e.g., at an input port, the sample flows through a channel into the PCR zone 244 where PCR takes place. That is, as the sample flows within a channel through the PCR zone 244, the sample/reagent mixture is exposed to the PCR temperature cycle a plurality of times to effect PCR amplification. Next, the sample flows into the thermal melt zone 242 where a high resolution thermal melt process occurs. Flow of sample into the microfluidic device 240 can be controlled by a flow control module 208. The flow control module 208 may be part of a control system 250 of the system 200. The control system 250 may comprise the flow control module 208, a PCR zone temperature controller 210, a PCR flow monitor 218, a thermal melt zone temperature controller 224, and/or a thermal melt zone fluorescence measurement/flow monitoring system 232. PCR and thermal melt zone flow control modes may be combined or used in an alternating fashion.

The temperature in the PCR zone 244 can be controlled by the PCR zone temperature controller 210. The PCR zone temperature controller 210, which may be a programmed computer or other microprocessor or analog temperature controller, sends signals to a heating device based on the temperature determined by a temperature sensor 214 (which may comprise one or more temperature sensors, such as, for example, a thin film resistive thermal detectors (RTD) or thin-film thermistor, or a thin-film thermocouple thermometer, described in more detail below). In this way, the temperature of the PCR zone 244 can be maintained at the desired level or cycled through a defined sequence. According to some embodiments of the present invention, the PCR zone 244 may also be cooled by a cooling device 216 (for example, to quickly bring the channel temperature from 95° C. down to 55° C.), which may also be controlled by the PCR zone temperature controller 210. In one embodiment, the cooling device 216 could be a peltier device, heat sink, or forced convection air cooled device, for example.

The flow of sample through the microfluidic channels can be measured by a PCR zone flow monitoring system 218 in communication with the flow control module 208 for controlling flow through the PCR zone 244. In one embodiment, the flow monitoring system can be a fluorescent dye imaging and tracking system illustrated in U.S. Pat. No. 7,629,124. According to one embodiment of the present invention, the channels in the PCR zone can be excited by an excitation device 220 and light fluoresced from the sample can be detected by a detection device 222. Exemplary excitation and detection devices are described below.

The thermal melt zone temperature controller 224, e.g. a programmed computer or other microprocessor or analog temperature controller, can be used to control the temperature of the thermal melt zone 242. As with the PCR zone temperature controller 210, the thermal melt zone temperature controller 224 sends signals to the heating component (which may comprise one or more heating components) 226 based on the temperature measured by a temperature sensor (which may comprise one or more sensors) 228 which can be, for example, an RTD, a thin-film thermistor, or thin-film thermocouple. Additionally, the thermal melt zone 242 may be independently cooled by cooling device 230 (which may comprise one or more cooling devices). The fluorescent signature of the sample can be measured by the thermal melt zone fluorescence measurement/flow monitoring system 232. The fluorescence measurement system 232 excites the sample with an excitation device 234, and the fluorescence of the sample can be detected by a detection device 236. Thermal melt zone fluorescence measurement/flow monitoring system 232 may also be in communication with the flow control module 208 for controlling flow through the thermal melt zone 242.

Figure 2:
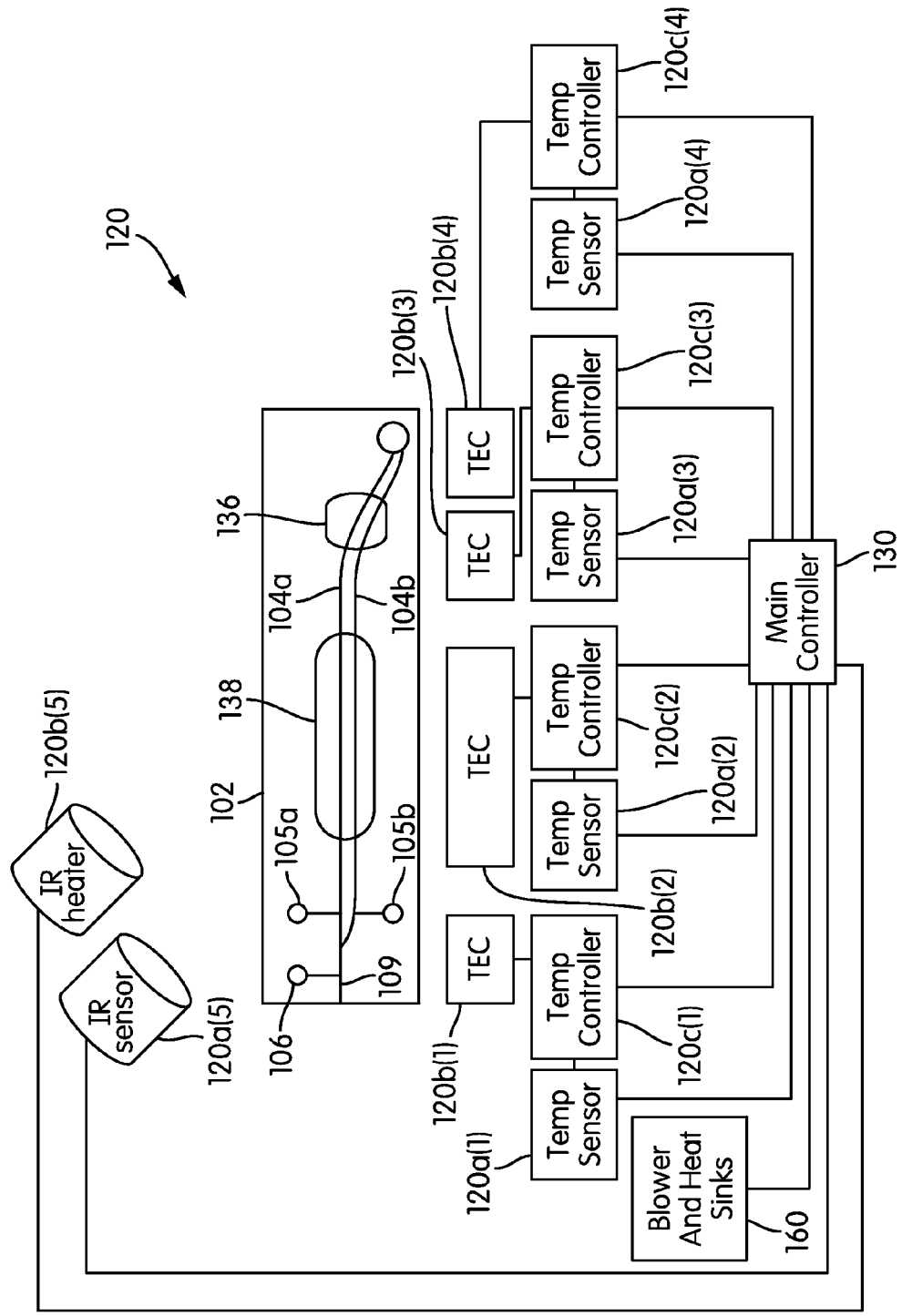
FIG. 2 is a block diagram illustrating a temperature control system that may be implemented in embodiments of the invention.

FIG. 2 illustrates an embodiment of a temperature control system 120. Temperature control system 120 may include a number of heating and/or cooling devices (e.g., a thermoelectric cooler (TEC), which is also known as a Peltier device, or other heating/cooling device), a number of temperature controllers, and a number of temperature sensors.

In the embodiment shown, temperature control system 120 includes a TEC 120*b*(1) for heating and cooling inlet 109, a TEC 120*b*(2) for heating and cooling the PCR zone 138, a TEC 120*b*(3) for heating and cooling the melting zone 136, and a TEC 120*b*(4) for heating and cooling the waste well 110. Each TEC 120*b*(1) 120*b*(4) may be connected to a temperature controller.

For example, in the embodiment shown, TEC 120*b*(1) is connected to temperature controller 120*c*(1), TEC 120*b*(2) is connected to temperature controller 120*c*(2), TEC 120*b*(3) is connected to temperature controller 120*c*(3), and TEC 120*b*(4) is connected to temperature controller 120*c*(4). In some embodiments, the temperature controllers 120*c*(1)-120*c*(4) may be implemented using the Model 3040 Temperature Controller, which is available from Newport Corporation of Irvine, Calif. In other embodiments, controllers 120*c*(1)-120*c*(4) may consist simply of a power amplifier.

The temperature controllers 120*c*(1)-120*c*(4) may be interfaced with main controller 130. This will enable main controller 130 to control the temperature of the different regions of microfluidic device 102. Temperature control system 120 may also include a temperature sensor 120*a*(1) for monitoring the temperature of inlet 109, a temperature sensor 120*a*(2) for monitoring the temperature of the PCR zone 138, a temperature sensor 120*a*(3) for monitoring the temperature of a melting zone 136, and a temperature sensor 120*a*(4) for monitoring the temperature of the waste well 110. Temperature sensors 120*a*(1)-120(4) may be in communication with a temperature controller 120*c*(1)-120*c*(4) and/or main controller 130, as is illustrated in FIG. 2.

Temperature control system 120 may further include an infrared sensor 120*a*(5) for monitoring the temperature of the PCR zone 138 and a source of electromagnetic radiation 120*b*(5) (e.g., a source of infrared, RF, Microwave, etc. radiation) for heating the PCR zone 138. Lastly, temperature control system 120 may include a blower and heat sinks 160 for cooling one or more of TEC 120*b*(1)-120*b*(4).

Figure 3:
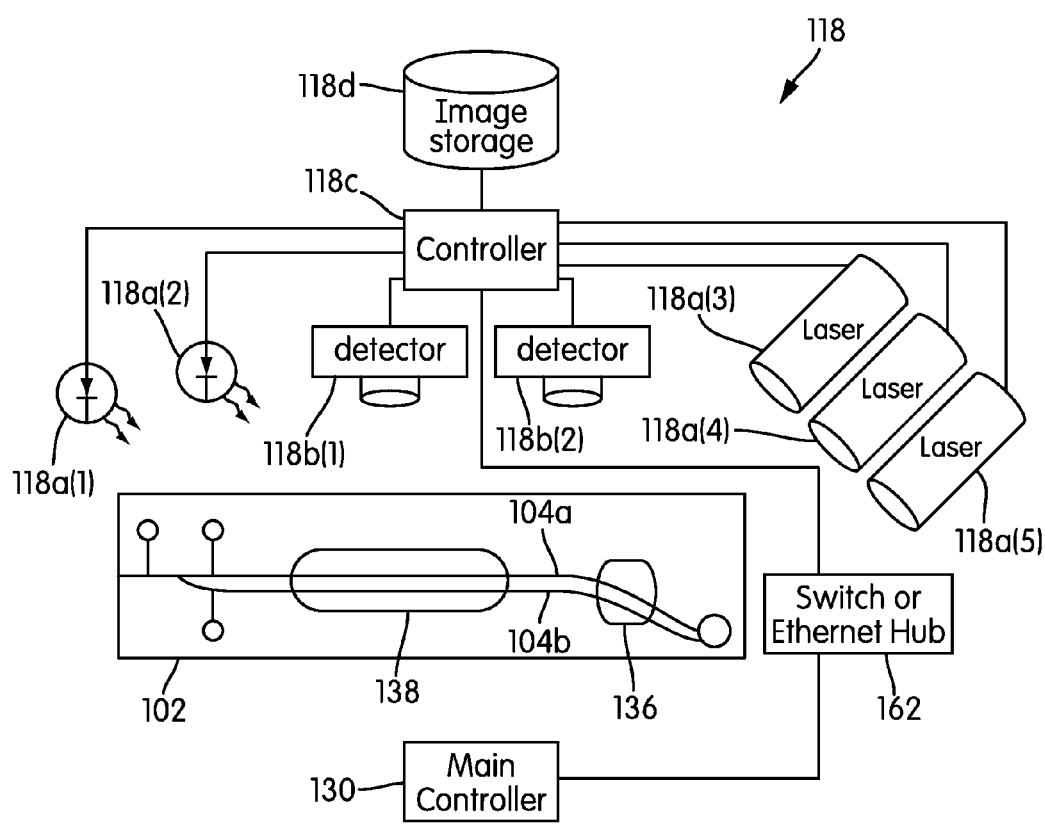
FIG. 3 is a block diagram illustrating an imaging system that may be implemented in embodiments of the invention.

FIG. 3 schematically illustrates an embodiment of an imaging system 118 according to some embodiments of the invention. Imaging system 118 may include a first detector 118*b*(1), a second detector 118*b*(2), a blue LED 118*a*(1), a red LED 118*a*(2), a first laser 118*a*(3), a second laser 118*a*(4), and a third laser 118*a*(5). Although two detectors 118*b*(1), 118*b*(2) are shown, it is contemplated that imaging system 118 may employ only a single detector.

Detector 118*b*(1) may be configured and arranged to detect emissions (e.g., fluorescent emissions) from PCR zone 138 and to output image data corresponding to the detected emissions. Detector 118*b*(1) may be implemented using a conventional digital camera, such as the Canon 5D digital SLR camera. Blue LED 118*a*(1) and red LED 118*a*(2) are configured and arranged such that when they are activated they will illuminate the PCR zone 138.

Detector 118*b*(2) may be configured and arranged to detect emissions from the melting zone 136 and to output image data corresponding to the detected emissions. Detector 118*b*(2) may be implemented using a digital video camera. In one embodiment, detector 118b(2) is implemented using an electron multiplying charge coupled device (EMCCD).

Lasers 118a(3), 118a(4), 118a(5) are configured and arranged to illuminate the melting zone. Each laser may output a different wave length of light. For example, laser 118a(3) may output light having a wavelength of about 488 nanometers, laser 118a(4) may output light having a wavelength of about 445 nanometers, and laser 118a(5) may output light having a wavelength of about 625 nanometers.

Imaging system 118 may include a controller 118c for controlling detector 118b(1), 118b(2) and excitation sources 118a(1), 118a(2), 118a(3), 118a(4), 118a(5). Controller 118c may also be configured to process image data produced by the detectors. Controller 118c may be implemented using a conventional microprocessor (e.g., controller 118c may consist of a conventional personal computer). Coupled to controller 118c may be an image storage device 118d for storing image data collected by detectors 118b(1) and 118b(2). Controller 118c may be in communication with main controller 130. Controller 118c may be directly connected to main controller or may be connected to main controller through a switch 162 or other communication device (e.g., an Ethernet hub).

Figure 4:
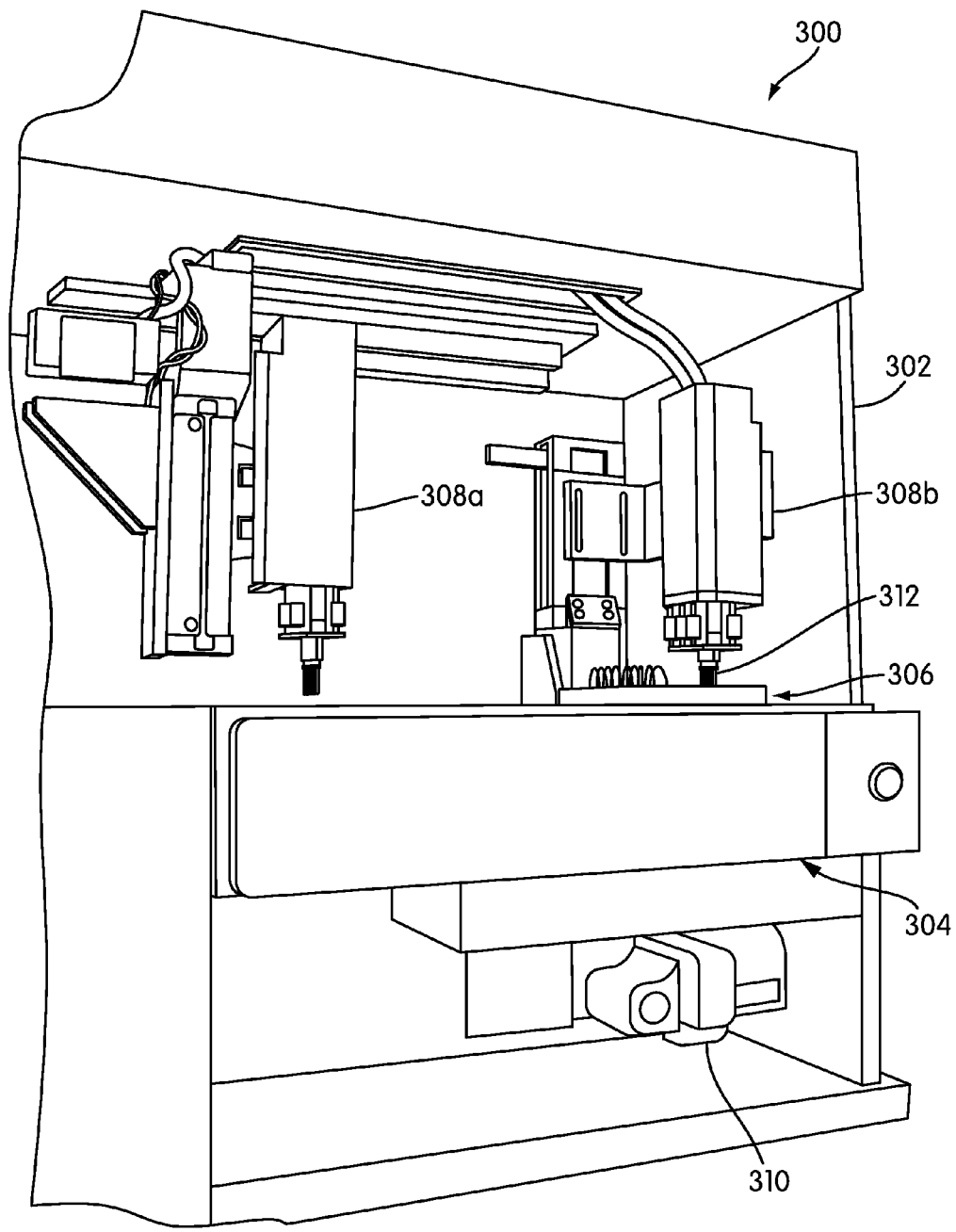
FIG. 4 is a front perspective view of an instrument and illustrates several functional components thereof according to one embodiment.

A cutaway drawing of the front side of an instrument 300 implementing a system for rapid serial processing of multiple nucleic acid assays, such as one of those described above, and embodying aspects of the present invention is shown in FIG. 4. As shown in FIG. 4, instrument 300 has a frame chassis 302, a processing drawer 304, a cooling manifold/connector assembly 306 (which may comprise components of the temperature control system 120 shown in FIGS. 1A and 2), a liquid handling system 308, and an optical system 310 (which may comprise components of the imaging system shown in 118 FIGS. 1A and 3, PCR zone flow monitoring system 218 shown in FIG. 1B, and/or the thermal melt zone fluorescence measurement system 232 shown in FIG. 1B). Liquid handling system 308 may comprise robotic pipettors 308a, 308b having pipette tips 312. Cooling manifold/connector assembly 306 may be located on a shelf of frame chassis 302 above processing drawer 304. Optical system 310 may be located below processing drawer 304. In preferred embodiments, the size of the instrument is such that it can fit on a typical laboratory bench-top.

Figure 5:
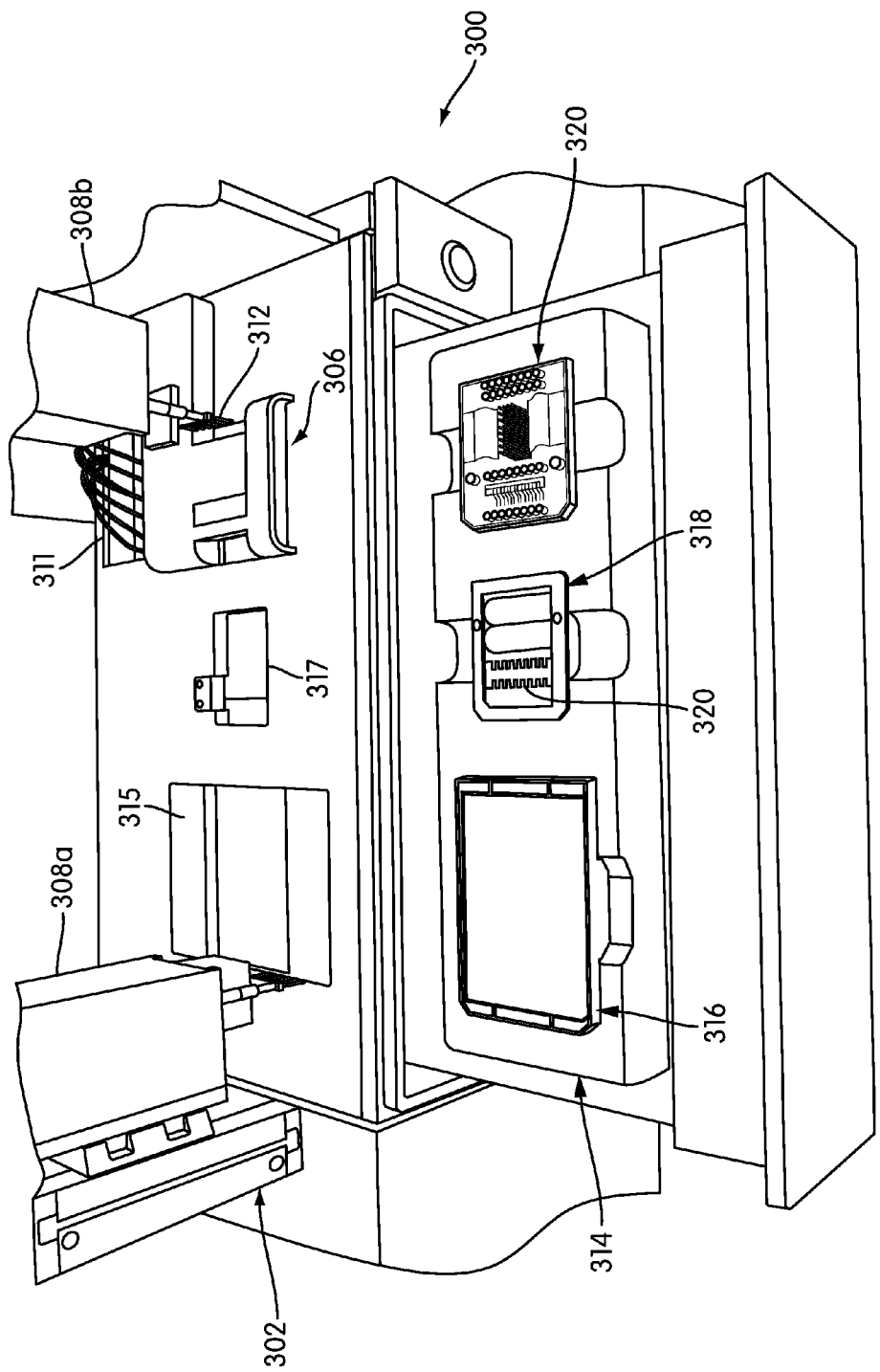
FIG. 5 is a partial top perspective view of the instrument shown in FIG. 4 with an open processing drawer according to one embodiment.

As shown in FIG. 5, processing drawer 304 may include a tray 314, which may be removable from the processing drawer 304. In one embodiment, a platform, or other support surface, 316, a pipette tip loading and cleaning station 318, and a microfluidic device 322, are carried on the tray 314. The platform/support surface 316 may carry a multi-well tray for holding a number of reagents and/or other fluid substances. The pipette tip loading and cleaning station 318 is supported on a pipette tip loading and cleaning station support structure of the tray 314 includes pipette tip racks 320 configured to removably hold a plurality (e.g., sixteen in the illustrated embodiment) pipette tips 312 and further includes a mechanism configured to clean the pipette tips. The microfluidic device 322, which may also be referred to herein as a microfluidic cartridge, is supported on a microfluidic device support structure of the tray 314 and includes an interface module and a microfluidic chip, as will be described in further detail below. Microfluidic device 322 may correspond to microfluidic device 102 in system 100 of FIG. 1A or microfluidic device 240 of system 200 of FIG. 1B. Microfluidic device 322 may include at least one channel with at least one dimension that is less than 1 mm that may contain fluid (e.g., liquid or gas). Microfluidic device 322 may have many channels and may be multifunctional. In preferred embodiments, microfluidic device 322 is capable of supporting PCR and/or thermal melt analysis. A multi-well tray carried on the platform 316 will be accessible to the robotic pipettors 308a, 308b through an opening 315 formed in the shelf of the frame chassis 302, and the pipette tip loading and cleaning station 318 will be accessible to the robotic pipettors 308a, 308b through an opening 317 formed in the shelf of the frame chassis 302.

In one embodiment, processing drawer 304 may open to allow input of disposables including, but not limited to: a reagent well-plate, a pipette tip loading and cleaning mechanism, and a microfluidic cartridge carried on the tray 314. For example, a user of instrument 300 places solutions into some or all of the wells of multi-well tray and places the multi-well tray on the platform 316 of the tray 314, places pipette tips on the racks 320 of the pipette tip loading and cleaning mechanism 318 and places the pipette tip loading and cleaning mechanism 318 on the tray 314, and places fluids (such as sample material) in storage wells of the a microfluidic device 322 and places the microfluidic device 322 on the tray 314. The tray 314 is then placed into the processing drawer 304, and the processing drawer is closed. The mechanism by which processing drawer 304 opens and closes may be either manual or motorized. The processing drawer 304 may also be computer-controlled to remain closed (and, optionally, locked) during a procedure while the instrument is running, and to open automatically at the completion of the procedure. The processing drawer 304 slides into the instrument 300 where it registers into the proper location. Insertion of the drawer 304 into the instrument frame chassis 302 places the components carried in the processing drawer in operational alignment with cooperating components and modules carried in the instrument above and below the processing drawer. For example, when the processing drawer 304 is closed, cooling manifold/connector assembly 306 may be located directly above microfluidic device 322, and optical system 310 may be located directly below the microfluidic device 322. The instrument 300 may also include a reader device (not shown), such as a bar-code reader or RFID reader, for reading a bar code or RFID tag placed on the microfluidic device 322 and which includes information data relating to identification of sample(s) to be assayed, dates, type(s) of assay(s) to be performed, etc. The reader device may comprises a hand-held device operated by an operator when the microfluidic device 322 is positioned within the drawer 304, or the reader device may be mounted on the frame chassis 302 and position relative to the microfluidic device support structure to read a bar code or RFID tag mounted on the microfluidic device 322 as the drawer 304 is closed.

Figure 6A:
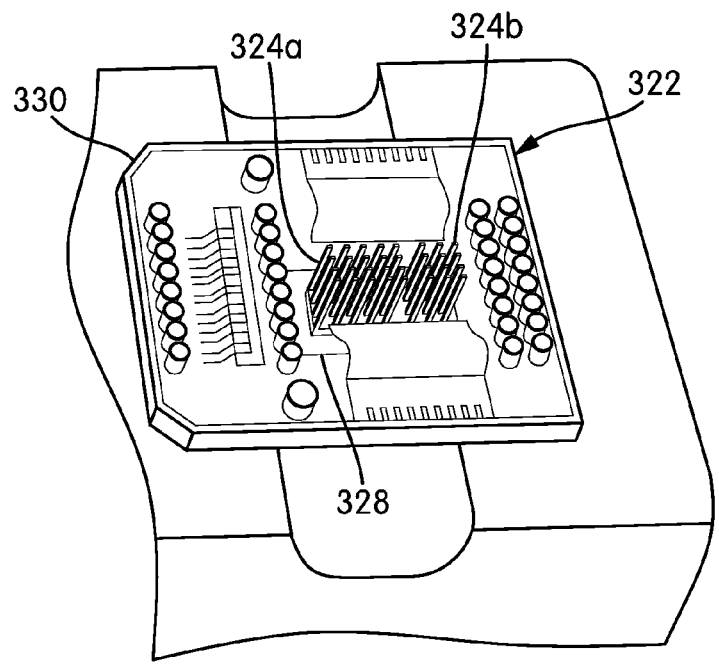
FIG. 6A is a perspective view of a microfluidic device according to one embodiment.
Figure 6B:
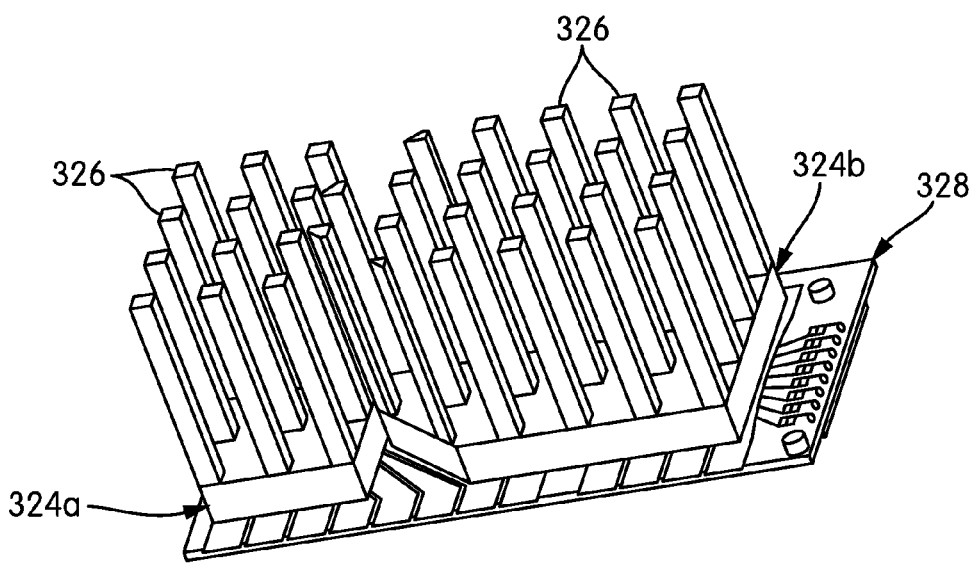
FIG. 6B is a perspective view of a heat sink assembly of a microfluidic device according to one embodiment.

FIGS. 6A and 6B show an example of the manner in which microfluidic device 322 may be configured, in accordance with one embodiment. Microfluidic device 322 includes an interface module 330 that couples fluids to a microfluidic chip 328 and may have a plurality of microfluidic channels extending across a substrate. Each channel may include one or more inlet ports and one or more outlet ports. Each channel may include a first portion extending through a PCR thermal zone and a second portion extending through a thermal melt zone. A sipper (not shown in FIGS. 6A and 6B) can be used to draw liquid into the plurality of microfluidic channels and/or the liquid handling system 308 may dispense fluids into the inlet ports(s) of the device 322. The microfluidic device 322 may include heater elements, which may be in the form of thin film resistive thermal detectors (RTDs) or thermistors. One or more heater elements may be associated with each microfluidic channel and may be located adjacent to the microfluidic channel. According to one embodiment of the present invention, when the microfluidic device 322 is positioned inside the instrument, the microfluidic device mates to the cooling manifold/connector assembly 306. According to one embodiment of the present invention, these connections are made on the upper surface of the microfluidic device 322. According to one embodiment, the wells and inlet ports of the microfluidic device 322 are accessible from above, while downstream vent and waste ports are covered by the cooling manifold and connected to the pressure control system. Tubes 311 shown in FIG. 4 connect a pressure source, e.g., a pump, with pressure ports on the underside of the manifold 306 which interface with the vent and waste ports of the microfluidic device 322.

Microfluidic device 322 may have one or more heat sinks 324a, 324b. In one embodiment, the heat sinks 324a, 324b may be extruded heat sinks. In the illustrated embodiment, microfluidic device 322 has two heat sinks 324a, 324b. One of the heat sinks 324a may be associated with at least one of a PCR thermal zone and a thermal melt zone of the microfluidic device, and another of the heat sinks 324b may be associated with at least the other of the PCR thermal zone and a thermal melt zone. In one embodiment, heat sinks 324a, 324b may be pin-fin heat sinks having fins 326 extending upwards from microfluidic device 322 in a substantially vertical direction, as illustrated in FIG. 6B.

Figure 7:
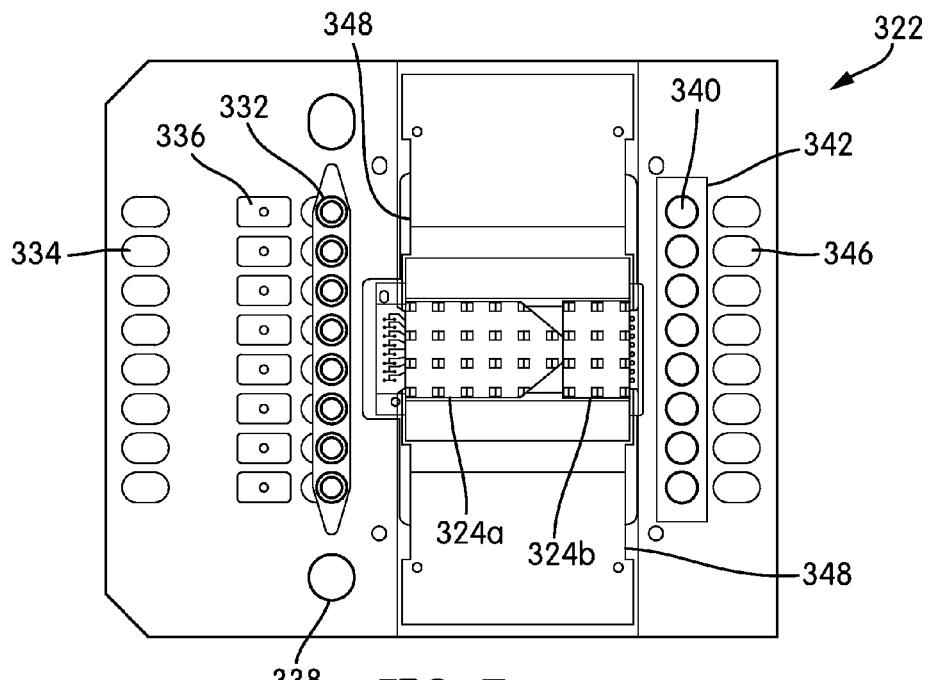
FIG. 7 is a top plan view of the microfluidic device according to one embodiment.
Figure 8:
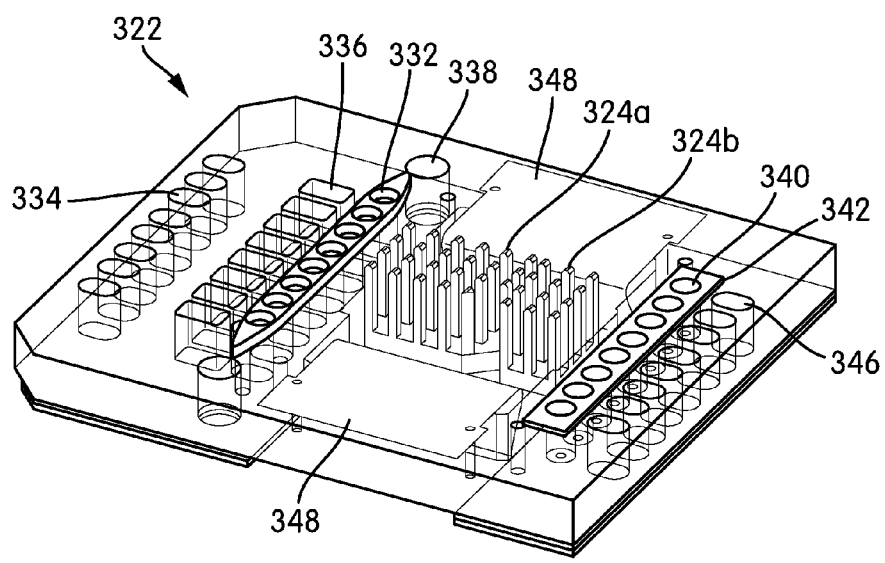
FIG. 8 is a perspective view of the microfluidic device according to one embodiment.

FIGS. 7, 8, 9, and 10 illustrate features of the microfluidic cartridge 322 in accordance with embodiments of the present invention. In one embodiment, the microfluidic device 322 comprises a PCR chip 328 (also illustrated in FIG. 9), made typically of glass, and an interface module 330 made from a polymer. Suitable polymers include PMMA, COC, COP, or polycarbonate. Suitable materials other than glass may also be used. As shown in FIG. 7, the microfluidic device 322 includes the interface module 330 which provides storage wells 334 for holding samples (e.g., nucleic acid samples). The interface module 330 also provides storage wells 346 for holding a blanking solution prior to its introduction to the microchannels. Additionally, the interface module 330 includes inlet ports 332 with pipettor docking features (described below), vent wells 336, registration features 338 (for aligning the module), downstream waste wells 340, a porous membrane filter 342 (for amplicon containment), PCR heat sinks 324a, 324b, and a flexible circuit connector from the PCR chip to the instrument.

In preferred embodiments, the microfluidic chip 328 and the interface module 330 each comprise micro-fluidic channels, and are bonded such that their micro-channels are connected. In a non-limiting embodiment, the microfluidic chip 328 and the interface module 330 are intended to handle eight independent nucleic acid samples. The interface module provides storage wells 334 for holding these eight samples. The interface module also provides eight storage wells 346 for storing the blanking solution prior to its introduction to the micro-channels.

Figure 9:
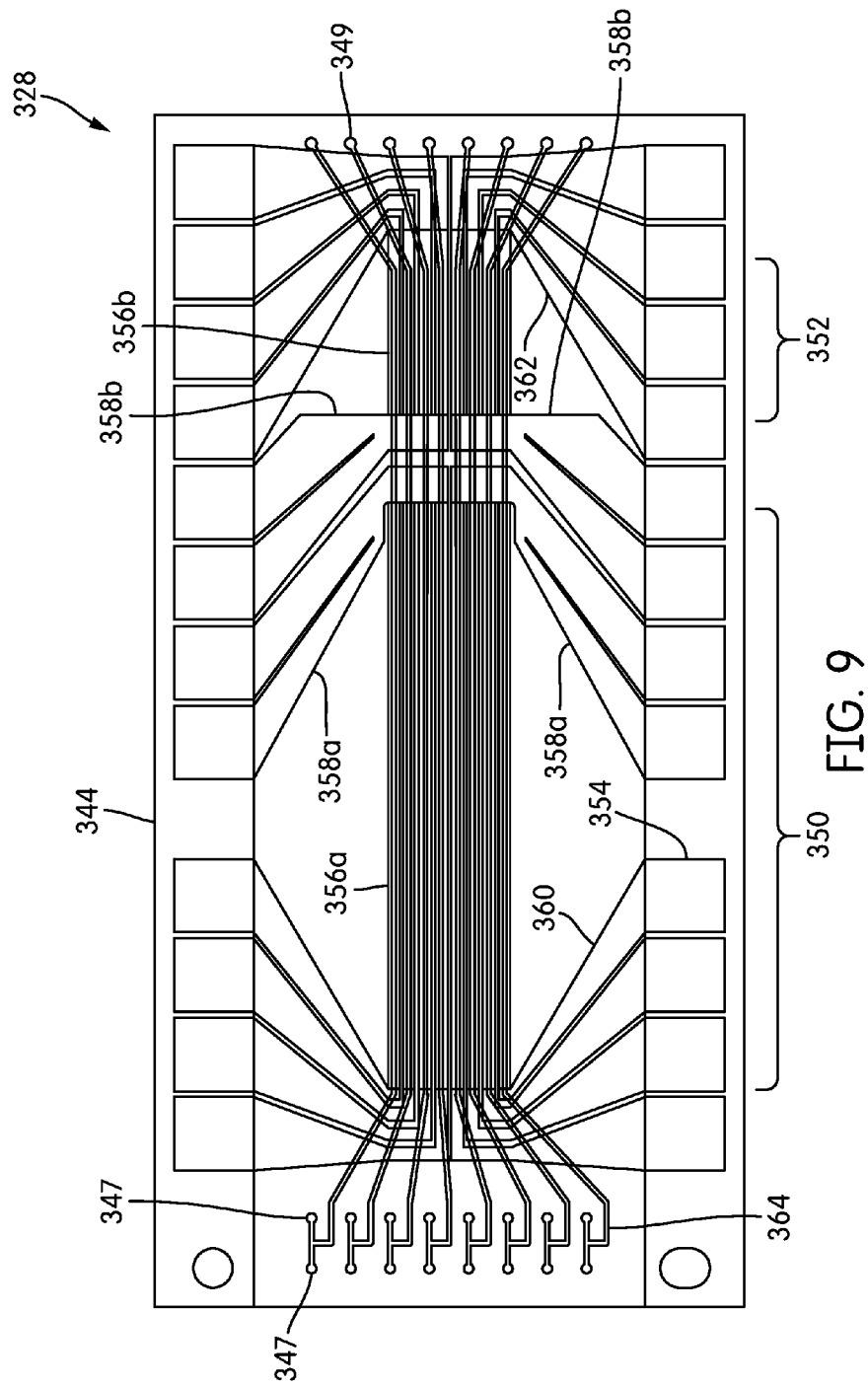
FIG. 9 is a top plan view of a microfluidic chip of the microfluidic device according to one embodiment.
Figure 10:
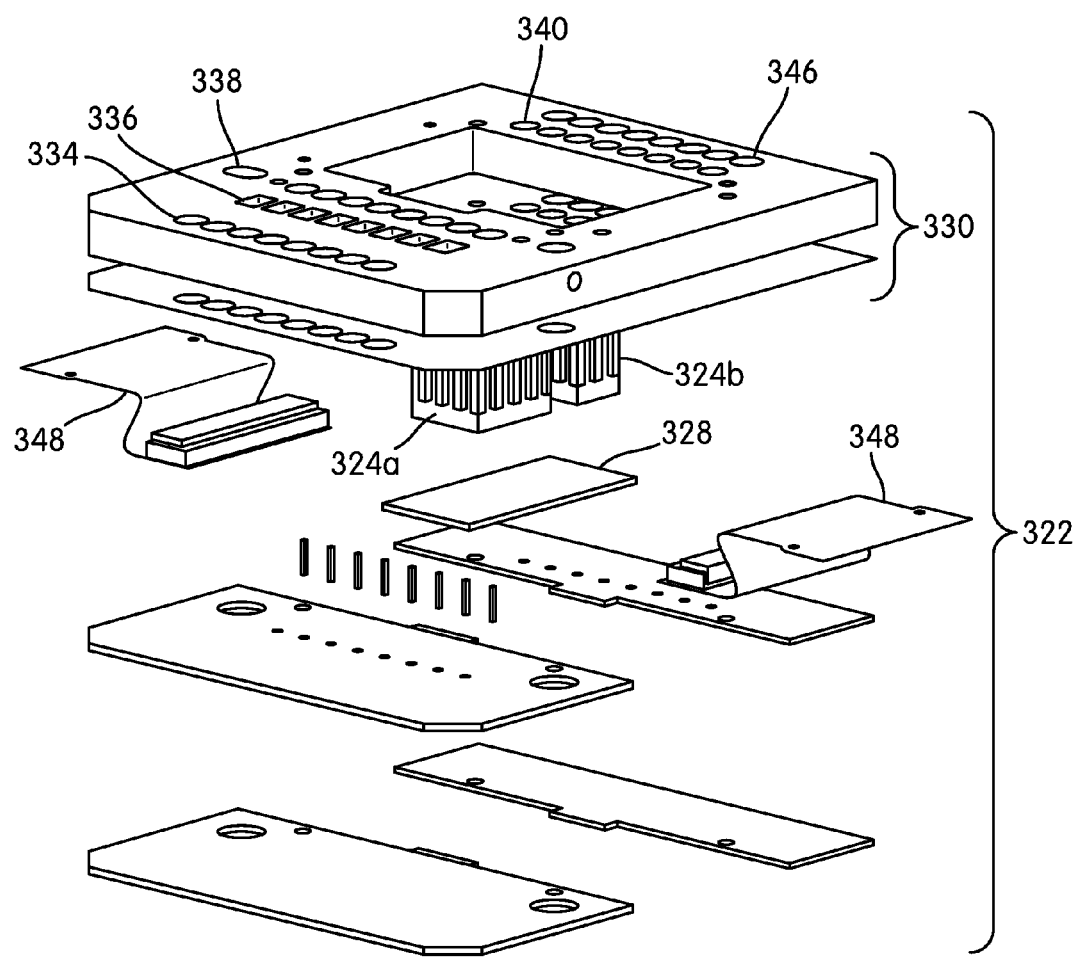
FIG. 10 is an exploded perspective view of the microfluidic device.

FIG. 9 illustrates the microfluidic chip 328 embodying aspects of the present invention. In the illustrative embodiment, the microfluidic chip 328 includes several microfluidic channels 364 extending across a substrate 344. Each channel 364 includes one or more inlet ports 347 (the illustrated embodiment shows two inlet ports 347 per channel 364) and one or more outlet ports 349 (the illustrated embodiment shows one outlet port 349 per channel 364). In exemplary embodiments, as described above, each channel may be subdivided into a first portion extending through a PCR thermal zone 350 and a second portion extending through a thermal melt zone 352.

In an embodiment, the microfluidic chip 328 further includes thermal control elements in the form of thin film resistive heaters associated with the microfluidic channels 364. In one non-limiting embodiment, the thin film resistive heaters 356 may be platinum resistive heaters whose resistances are measured in order to control their respective temperatures. In the embodiment illustrated in FIG. 9, each heater element comprises two heater sections: a PCR heater 356a section in the PCR zone 350, and a thermal melt heater section 356b in the thermal melt zone 352.

In one embodiment, the microfluidic chip 328 includes a plurality of heater electrodes 354 connected to the various thin-film heaters 356a and 356b. The flexible circuit connectors 348 have individual contacts (not shown) for connecting to each heater electrode 354. The flexible connectors may also included extra contacts for detecting the chip 328. In non-limiting embodiments, heater electrodes 354 may include PCR section leads 360, one or more PCR section common lead 358a, thermal melt section leads 362, and one or more thermal melt section common lead 358b. According to one embodiment of the present invention, a separate PCR section lead 360 is connected to each of the thin-film PCR heaters 356a, and a separate thermal melt section lead 362 is connected to each of the thin-film thermal melt heaters 356b.

In one embodiment, as shown in FIG. 9, the eight channels 364 do not fluidly connect with each other. Each channel has the topology of a "T" or three branches extending to inlet port 347, a vent port, and outlet port 349. The ends of the branches connect to the inlet port 332, the vent well 336, and the waste well 340, respectively, of the interface module 330. The three branches converge at a "T" junction inside the chip 328. This topology allows one to create short boluses, or slugs, of reaction materials in the chip by alternately pulling sample and blanking solution by applying a slight negative pressure (such as, for example, approximately −0.2 psi) at the vent well 336. Net flow in the chip 328 can be held at zero until the desired concentration of reactants is reached at the T junction near the beginning of the PCR zone 104. In a non-limiting embodiment, after the desired concentration is reached, flow from the inlet port 332 is stopped and negative pressure is applied to the waste well 340 of the interface module 330 to pull a new slug into the chip. The pattern is repeated, alternating sample slugs with blanking slugs.

FIG. 9 further illustrates that in the chip 328, reagent solutions are introduced via inlet ports 347 at the "T" junction on the left, according to one embodiment. In the illustrated embodiment, negative pressure applied at the downstream outlet ports 349 pulls new fluids into the main channels 364 and flow moves from left to right.

Further structural details of the embodiment of the microfluidic cartridge 322 are shown in U.S. Design patent application No. 29/368,929, entitled "Cartridge assembly," U.S. Design patent application No. 29/368,936, entitled "Cartridge assembly," and U.S. Design patent application No. 29/368,874 entitled "Two-Part Heat Spreader Design for Compact Microheaters," the respective disclosures of which are hereby incorporated by reference.

As discussed above, in one embodiment of the present invention, liquids are introduced to the microfluidic channels of the cartridge 322 by way of inlet ports 332 on the top side of the interface module 330 of the cartridge 322. These inlet ports are accessible to the robotic pipettors 308a, 308b of the liquid handling system 308. In one embodiment, the robotic pipettors are mounted on motorized translation stages that enable movement in x, y, and/or z directions. In one embodiment, the liquid handling system 308 operates by moving the pipettors to pick up the desired amount of reagent solution from each desired well location in tray 202, mixing the different solutions if needed, moving to the inlet ports 332, and pushing a droplet into contact with the inlet port 332. The robot remains stationary while in contact with the inlet port, and fluid is drawn into the cartridge by applying partial negative pressure to a downstream vent well of that channel. After fluid is drawn into the cartridge, the robot pipettor can reversibly break and re-establish the connection to the inlet port. The top side of the cartridge also may include wells, such as storage wells 334, 346, for storing solutions before they are picked up and loaded into the micro-channels.

Referring back to the exemplary embodiment of the instrument 300 illustrated in FIG. 4, two robotic pipettors are shown 308a. 308b. Each robotic pipettor may be configured to dispense a different fluid into the inlet ports of the microfluidic device. For example, in accordance with one non-limiting embodiment, on the left is an 8-channel pipettor 308a (referred to as the "PCR robot") dedicated to creating the PCR test slugs. On the right is an 8-channel pipettor 308b (referred to as the "blanking robot") dedicated to creating spacer slugs that are use to separate the test slugs and to allow fluid flow rates within the cartridge to be monitored and controlled. In an exemplary embodiment, the instrument includes at least one robotic pipettor 308a, 308b, a bank of syringe pumps for use with the robotic pipettor during assays, such as PCR, a well-plate, the processing drawer, a bank of syringe pumps for blanking using a robotic pipettor, motorized translation stages configured to move the pipettors, a cooling manifold/connector assembly, microfluidic device, and a pipette tip loading station. In an alternative embodiment, creating PCR test slugs and creating spacer slugs are performed by a single robotic pipettor.

Figure 11:
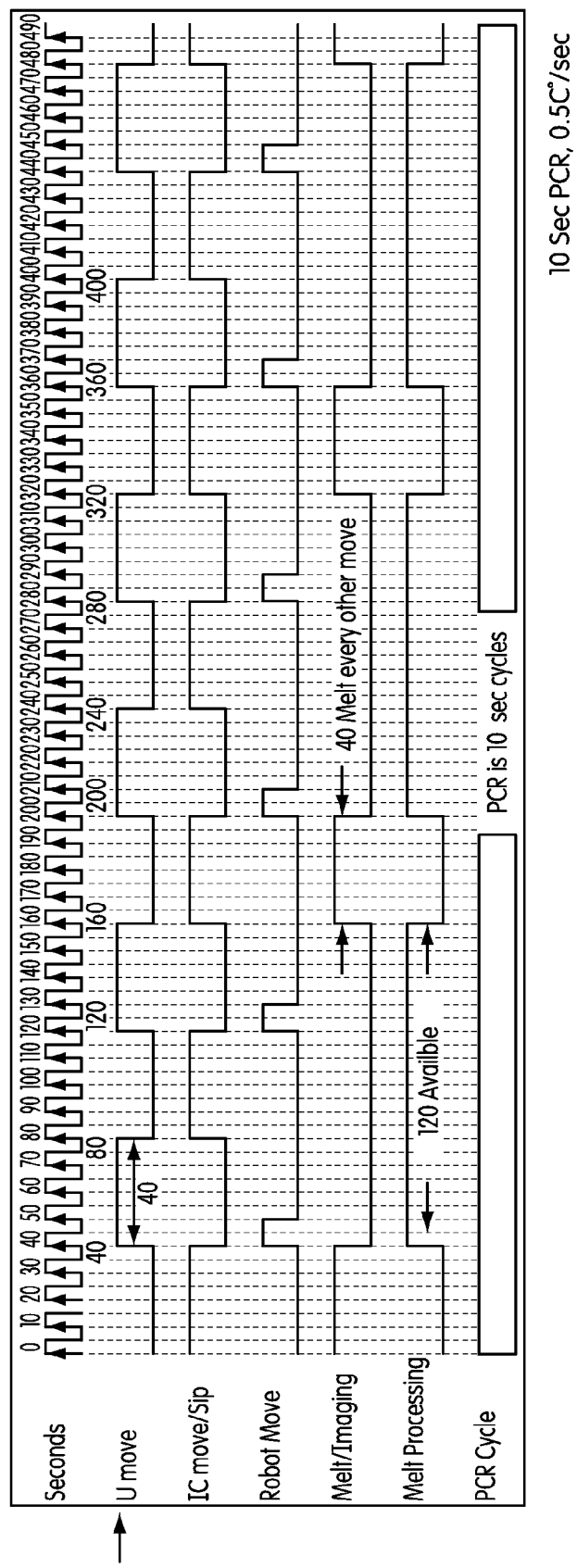
FIG. 11 is a timing diagram showing alternating movement of fluids in a microfluidic device and interface chip according to one embodiment.

A non-limiting example of one possible timing diagram of the sequence is illustrated in FIG. 11. As shown in FIG. 11, a timing diagram is illustrated showing alternating movement of fluids in a PCR chip (U Move) and interface chip (IC Move/Sip). These movements are also coordinated with the timing of the melt data acquisition (melt imaging) and melt processing. According to this non-limiting exemplary timing diagram, a new sample is processed every 160 seconds. This method counteracts the effects of slug dispersion as it travels through a channel, especially in the less precise and typically large channels of the interface module. The ability to create and maintain short slugs is advantageous because it allows multiple processing steps to happen simultaneously and therefore increase test throughput.

Additional details of an embodiment of the microfluidic device 322 and an associated pipette and pipette docking features are further described in application U.S. Patent Application No. 61/378,722, entitled "Method, Devices, and Systems For Fluid Mixing and Chip Interface," and U.S. application Ser. No. 13/222,450 claiming priority therefrom, the disclosures of which are hereby incorporated by reference. The microfluidic device and the system described therein can be used in conjunction with aspects of the present invention. For example, one can obtain multiple reagents, mix them, deliver them to a microfluidic device (e.g., an interface module), and utilize the flow control module 208 to create fluid segments that flow through the microfluidic device 240 (see FIG. 1B) with minimal mixing between the fluid segments, in accordance with aspects of the invention.

In non-limiting embodiments of the present invention, two or more fluids can be mixed utilizing a pipette, such as, for example, a positive air displacement pipette, pressure driven pipette, or capillary. Mixing can occur with the pipette tip itself and fluids can be delivered in a mixed state, for example, to a microchannel embedded in a microfluidic interface module.

Figure 14:
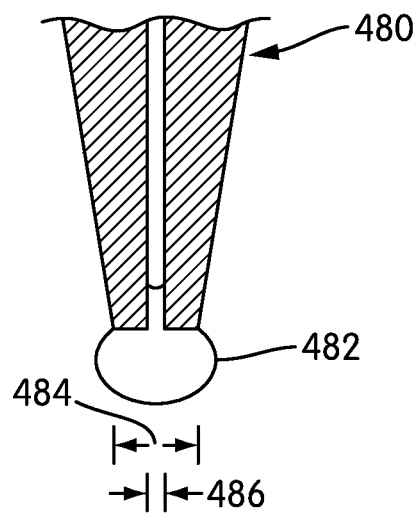
FIG. 14 is a partial cross-sectional view of a pipette tip that may be used in association with an embodiment of the present invention.

FIG. 14 is a partial cross-section of the distal end of a pipette tip 480 of such an embodiment. The pipette tip 480 may be constructed such that the fluid remains a bead 482 on the end of the tip and does not move up the sides of the pipette tip. In some preferred embodiments, the ratio of the outside diameter 484 of the pipette tip to inside diameter 486 of the pipette tip is sufficiently large at the orifice of the pipette tip such that inside diameter 306 is small enough to accurately collect less than 1 μL of fluid, while the outside diameter 484 is large enough to prevent liquid from wicking up the outside of the pipette tip when a bead is formed outside the tip. In one embodiment, the outside diameter 484 is 1.9 mm and the inside diameter 486 is 0.297 mm for a ratio of approximately 6.4. Furthermore, in preferred embodiments, the ratio of the outside diameter 484 to the inside diameter 486 provides sufficient surface area for a fluid bead 482 to attach by surface tension or other adhesion means. In some embodiments, the pipette tip 480 can comprise a 10 μL tip with a disk (not shown) attached to the end of the tip. In one preferred embodiment, the disk has a 2.2 mm diameter and is 0.4 mm thick. The disk can provide sufficient surface area for a fluid bead to attach, while preventing the bead from climbing up the outside of the pipette tip.

Figure 15:
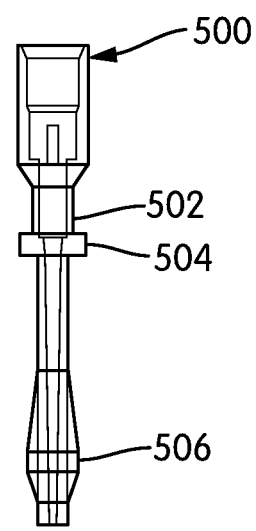
FIG. 15 is a side view of a pipette tip that may be used in association with an embodiment of the present invention.

FIG. 15 illustrates a pipette tip 500 (which may correspond to pipette tip 312 show in FIG. 4) embodying aspects of the present invention. As illustrated in FIG. 15, in some embodiments the pipette tip 500 includes a filter receiver 502 for storing a filter (not shown). In some embodiments, a filter can be located in the filter receiver 502 to minimize contamination beyond the pipette tip (that is, to prevent fluids in the disposable pipette tip from contaminating the pipettor 308a, 308b).

In some embodiments, the pipette tip 500 also includes a load and eject interface 504. The interface 504 can be used to facilitate the automatic loading and removal of pipette tips, for example using a robotic control system in communication with a main controller, such as main controller 130 in FIG. 1A.

Figure 16A:
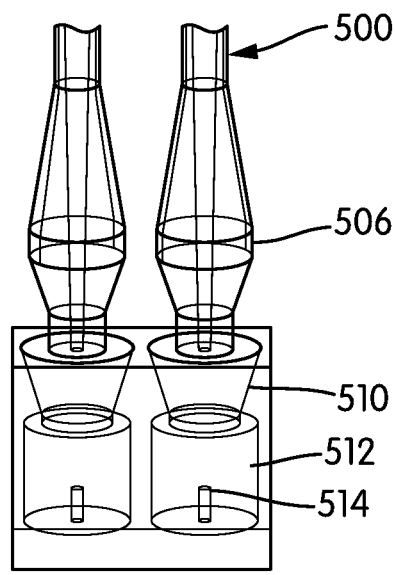
FIGS. 16A and 16B are a perspective view and a side view, respectively, of pipettes and microfluidic devices that may be used in association with the present invention.
Figure 16B:
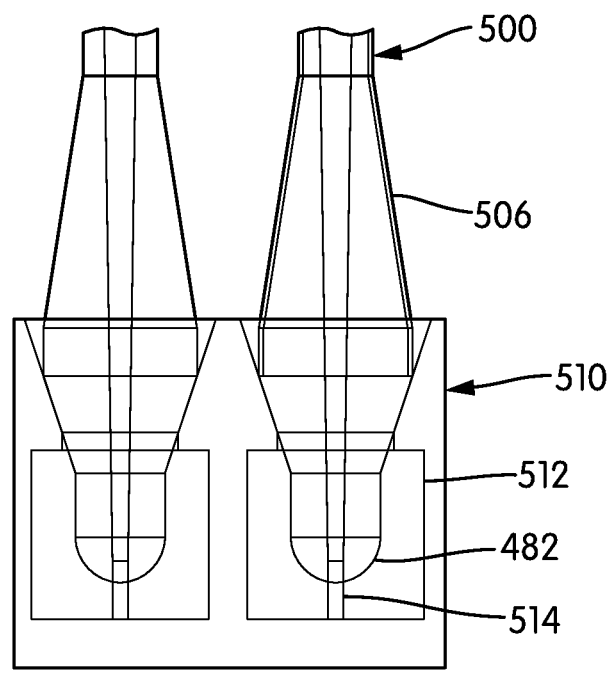

In some embodiments, the pipette tip 500 also includes a docking feature 506. The docking feature 506 can be used to enable automatic alignment of multiple tips with multiple capillaries (e.g., microchannels), for example, by aligning each pipette tip with a microchannel when the pipette tip is moved toward that microchannel (e.g., when delivering fluids to an inlet port of a microfluidic device). An example of the docking feature 506 is depicted in FIGS. 16A and 16B. FIG. 16A depicts pipette tip 500 having a docking feature 506 positioned above a reservoir or well 512 (e.g., inlet port 332) of a microfluidic device having a docking receptacle 510 and a microchannel 514 (e.g., a microfluidic channel extending from the well 512). FIG. 16A depicts pipette tip 500 engaged with the reservoir or well 512 via the docking feature 506 and docking receptacle 510. Once engaged with the docking receptacle 510, the proximity of the pipette tip 500 and the microchannel 514 allows the fluid bead 482 to contact the microchannel 514 while remaining attached to the pipette tip 500.

In one embodiment, mixing of the fluids can be accomplished by pushing the majority (i.e., more than half) of the fluid out of the pipette, to form a bead at the pipette tip, and retracting the bead back into the pipette tip. In some embodiments, this is repeated multiple times, such as, for example, four times. Surface tension prevents the bead from falling off of the pipette tip. As this bead is pushed forward and then retracted multiple times, the fluids swirl together and mix. In some embodiments, a small amount of fluid is used (for example, less than 10 µL) to ensure that the bead of liquid does not separate from the pipette tip.

Figure 17:
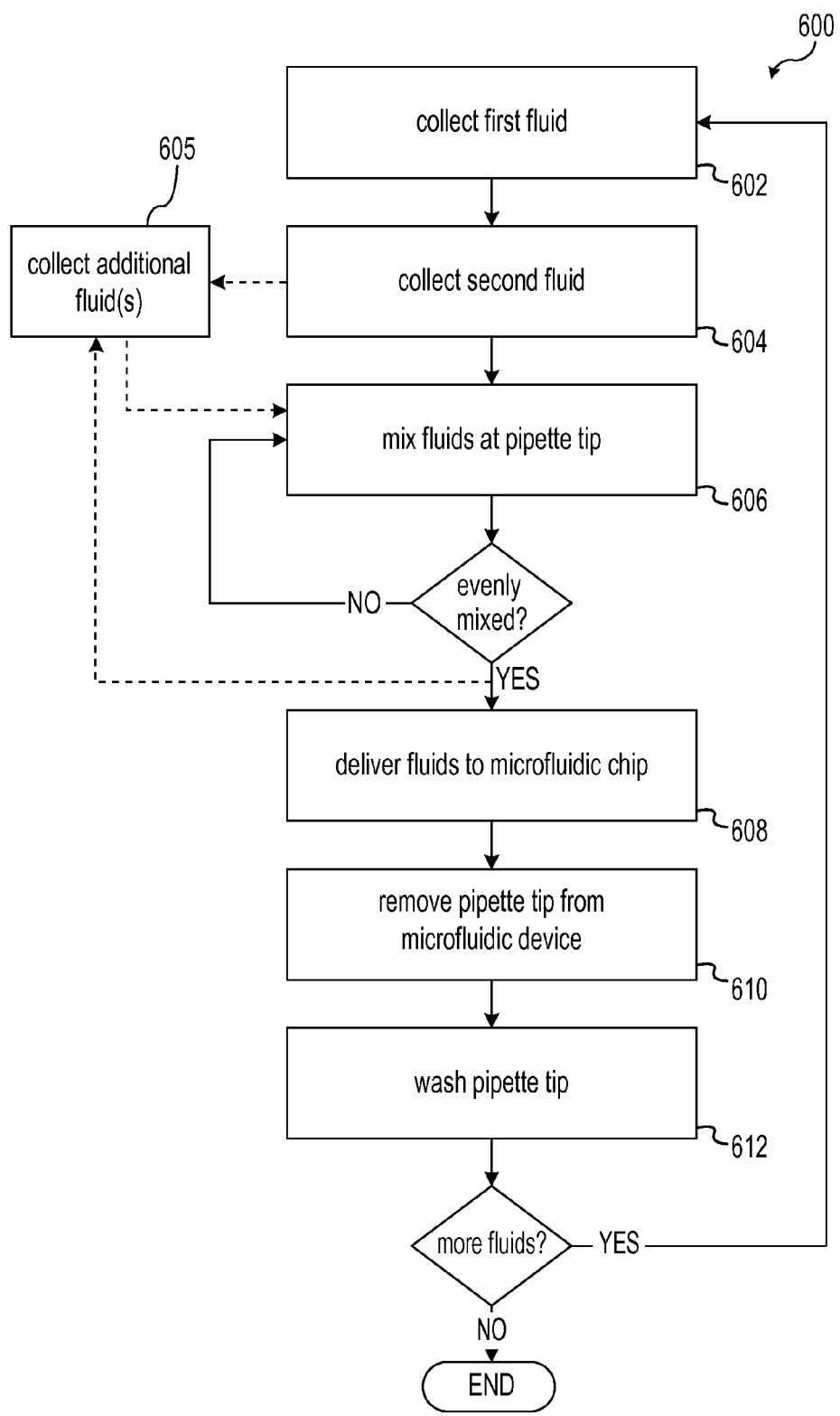
FIG. 17 is a flow chart illustrating a process for mixing two or more fluids according to aspects of the present invention.

FIG. 17 illustrates a process 600 for obtaining multiple fluids (for example, reagent fluids), fully mixing them, and delivering them to a microfluidic chip. The process 600 may be performed, for example, under the control of one or more robots (i.e., an automated controller of pipettes for collecting, mixing, and delivering samples). The robot may be, for example, a PCR robot (i.e., an automated controller of pipettes for collecting, mixing, and delivering PCR samples). The robot may or may not operate in conjunction with flow control module 208.

The process 600 may begin at step 602 at which a pipette collects an amount of a first fluid. The first fluid may be, for example, a common reagent ("CR") fluid, but this is not required. The amount of the first fluid may be, for example, 1 µL. However, other amounts (e.g., more or less than 1 µL) of the first fluid may be collected by the pipette. As will be understood by those having skill in the art, this can include drawing the first fluid up into the pipette tip from, for example, a multi-well plate, such as plate 140 in FIG. 1A, disposed on platform 316 shown in FIG. 5.

At step 604, the same pipette collects an amount of a second fluid. The second fluid may be, for example, a primer fluid or a common reagent fluid. The amount of the second fluid may be, for example, 1 µL. However, other amounts (e.g., more or less than 1 µL) of the second fluid may be collected by the pipette. As will be understood by those having skill in the art, this can include drawing the second fluid up into the pipette tip from, for example, a multi-well plate. Additional fluids may also be aspirated.

At step 606, the fluids are mixed, if needed, within the pipette. As described above, step 606 can include expelling a droplet of the fluids, that is, pushing the majority of the fluid out of the pipette to form a bead (e.g., a bead of approximately 2 µL) at the pipette tip and then drawing the bead back into the pipette tip. In some embodiments, the expelled droplet has a volume approximately equal to the volume of fluid that was collected by the pipette. In one non-limiting example, if 1 µL of the first fluid and 1 µL of the second fluid were collected by the pipette, in step 606, the pipette may expel a droplet having a volume approximately equal to the 2 µL.

In some embodiments, the step 606 can be repeated multiple times to ensure that the fluids are evenly mixed. For example, in some embodiments the bead can be cycled out of and into the pipette 2, 3 or 4 or more times. The number of cycles necessary to achieve adequate mixing may be empirically determined. In other embodiments, the number of cycles need not be pre-set; the mixing could be monitored by the system through optical, conductive, acoustic, or other means known in the art. In addition, the system controller can vary the number of cycles, the speed of the cycle, timing of the cycles, etc., based on feedback relating to degree of mixing if the number of cycles is not pre-determined. Moreover, mixing could be performed using a combination of pre-determined cycles and feedback control. That is, a pre-determined number of cycles can be specified and performed, feedback can be used to determine if the fluids are fully mixed, and, if necessary, one or more additional cycles can be performed.

At step 608, the fluids are delivered in a mixed state to a microfluidic chip. In some embodiments, for each fluid mix that is introduced into the interface module, the pipette produces a small bead of fluid (e.g., approximately 1-4 µL) and causes the bead to make contact with the top of a microchannel in the microfluidic chip. After this contact is made, the pressure in the chip can be lowered (e.g., via the flow control module 208) to pull fluid into one or more channels of the chip. The pipettor may dispense additional fluid into the bead as it is aspirated into the chip.

At step 610, the pipette tip is removed from the microfluidic chip. In some embodiments, this can include removing the bead from contact with the microchannel. When the pipette tip is removed from the microchannel, the residual fluid remaining in the bead (i.e., fluid in the bead that was not drawn into the microchannel) remains with the pipette tip due to higher surface tension on the tip relative to the microchannel, thus leaving fluid only inside the microchannel. This allows for fluids to be switched into the chip without leaving residual fluid in the area of the microchannel.

In some embodiments, the inside diameter of the microchannel is made small enough that the negative pressure used to move liquids into the chip does not exceed the back pressure due to surface tension within the mouth of the microchannel. Thus, air cannot enter the microchannel which would cause bubbles in the microchannel that block flow. This feature can prevent air bubbles from entering the microfluidic chip via the microchannel.

At step 612, the pipette tip is washed, if necessary, to remove any residue of the mixed fluids. After step 612, the process 600 may return to step 602 to begin obtaining new fluids for mixing and delivery to the micro fluidic device.

In other embodiments of the present invention, beads can be made of sizes smaller or larger than those bead sizes described above. In addition, although the fluids are described as being drawn up from a multi-well plate, it is not necessary that both fluids be drawn from the same multi-well plate. The fluids may instead be drawn from different multi-well plates. Also, the fluids may be drawn up into the pipette tip from other sources, such as, for example, a single-well plate, single tube, flowing or stationary fluid reservoir, jug—essentially anything capable of holding a liquid.

The system and method described above is a non-limiting manner utilizing two fluids and one pipette. In other embodiments, the fluid handling system can be configured to simultaneously mix three or more fluids in one pipette, as shown in step 605. For example, process 600 may include a step of collecting a third fluid (e.g., a patient sample) after the pipette collects an amount of a second fluid at step 604 and before the fluids are mixed within the pipette at step 606. There may also be one or more intermediate mixing steps before all of the fluids to be mixed in the pipette have been collected. Mixing can be done in any manner—2, 3, 4 or more fluids can be mixed at once, some subset of fluids can be mixed first followed by the addition of additional fluids and remix, etc. In one embodiment of PCR, three fluids are mixed: master mix, DNA sample, and primers In further embodiments, the present invention can be configured to simultaneously mix three or more fluids in a plurality of pipettes. For example, in one embodiment, FIG.

Figure 38:
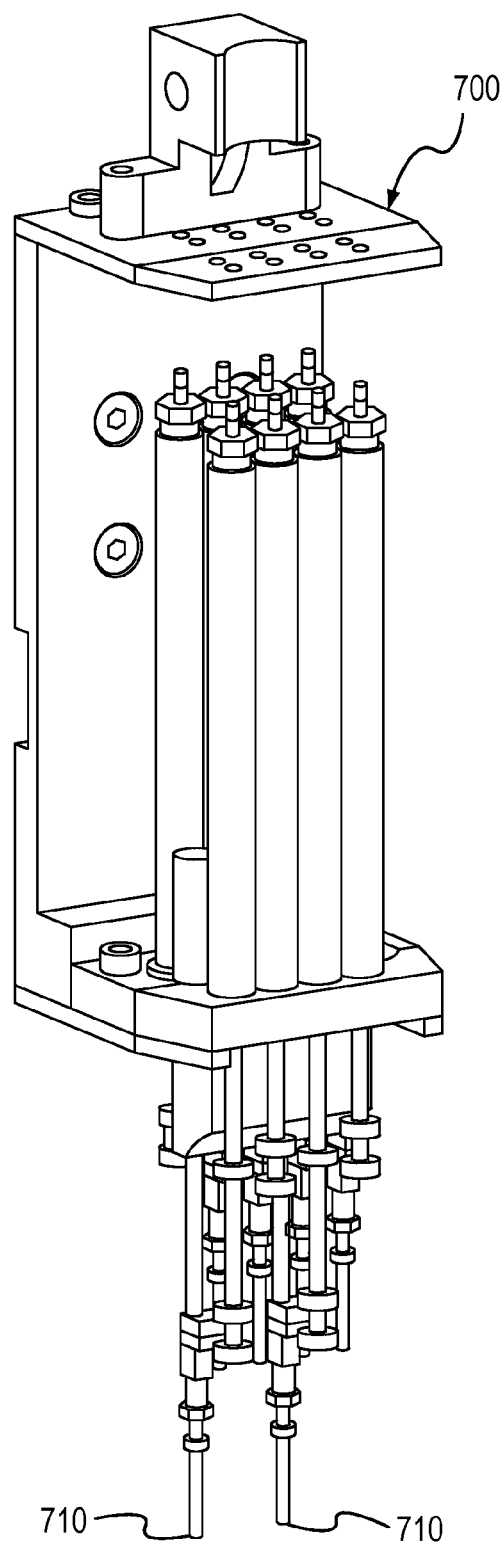
FIG. 38 is a perspective view of a multichannel pipettor assembly embodying aspects of the present invention.

38 illustrates an eight-channel pipettor 700 (which may correspond to robotic pipettor 308), that is, an assembly of eight pipettor channels 710 that can be moved as a unit, for example, by robotic control (not illustrated) in an x, y, or z direction (or any combination thereof). In some preferred embodiments, the eight-channel pipettor 700 is configured such that each pipettor channel 710 can be individually extended (e.g., actuated in the z direction) to engage a pipette tip or for fluid delivery and/or retrieval. For example, in FIG. 38, two of the eight pipettor channels 710 are extended. This feature provides an embodiment wherein any specific reagent can be mixed with any of eight different patient samples. However, other multichannel pipettors may be used. One such example is shown in U.S. Design patent application No. 29/365,966, entitled "Pipettor Head Assembly," the disclosure of which is hereby incorporated by reference.

As shown in FIGS. 4 and 5, each robotic pipettor 308a, 308b includes pipette tips 312. In one embodiment, each pipettor channel 710 of the eight-channel pipettor 700 shown in FIG. 38 engages an individual pipette tip 500 (FIG. 15) carried on the pipette tip racks 320 of the pipette tip loading and cleaning mechanism 318 (FIG. 5) to removably secure the pipette tip on a distal end of the pipettor channel 710. The pipettor 700 is positioned above opening 317 above the pipette tip loading and cleaning mechanism 318, and the pipettor channels 710 engage an associated one of the pipette tips 500 by moving downwardly into the opening 317 to insert the distal end of the pipettor channel 710 into the pipette tip 500. All eight pipettor channels 710 may engage associated pipette tips simultaneously, or the pipettor channels 710 may engage the associated pipette tips 500 one at time. When all the pipettor channels 710 have engaged associated pipette tips 500, the pipettor 700 moves laterally to move the pipette tips 500 out of the pipette tip rack 320 before the raising the pipettor 700 out of the opening 317.

Figure 39:
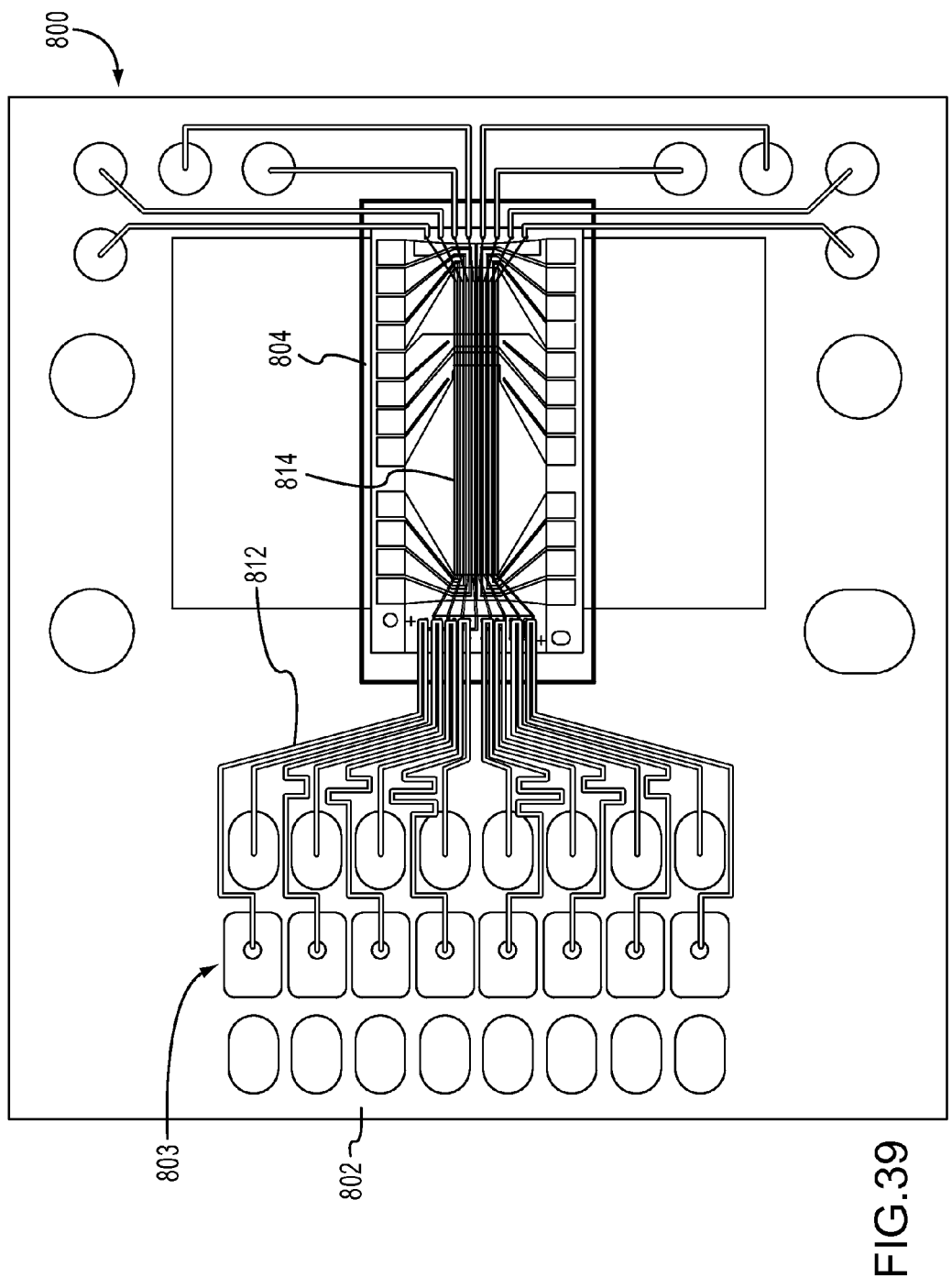
FIG. 39 is a top plan view of an alternative microfluidic device according to an embodiment.

FIG. 39 illustrates a microfluidic device 800 similar to the microfluidic device 322 (see FIG. 7) described above for providing fluid segments that move through a microfluidic chip with minimal mixing between serial segments, in accordance with some embodiments of the present invention (microfluidic device 322 could also be used and microfluidic devices 322 and 800 are, in many respects, functionally interchangeable). In the non-limiting exemplary embodiment of FIG. 39, the microfluidic device, or cartridge, 800 includes an interface module (also referred to as interface chip) 802 and a microfluidic chip (also referred to as a reaction chip) 804. In some embodiments, the interface module 802 can include inlet ports or wells 803 that allow different fluids to be entered into the microfluidic device in series, such as by the process 600 (see FIG. 17) described above. In some embodiments, the reaction chip 804 is a smaller chip that carries out the reaction chemistry, such as PCR and thermal melting.

In an exemplary process for moving fluid segments serially through a microfluidic chip, a first fluid is drawn by a first pumping system into the microchannels 812 of the interface module 802 to fill the microchannels 812. For example, in some embodiments the first fluid may include a fluid mixed and provided to the interface module 802 as described above with reference to the process 600, such as fluids for individual PCR reactions. In some embodiments, the step may be performed by the flow control modules. It is not necessary that the same first fluid is drawn into each of the microchannels 812. The first fluid drawn into any one of the microfluidic channels 812 may be different from the first fluid drawn into any of the other microfluidic channels 812.

Next, a second pumping system (which may comprise the first pumping system or components of the first pumping system) moves a segment of fluid from the microchannels 812 of the interface module 802 into the microchannels 814 of the reaction chip 804. In some embodiments, this step may be performed by the flow control module (such as flow control module 208 of the system 200 shown in FIG. 1B). In some embodiments, the same flow control module may control both the first and second pumping systems independently; in some embodiments, a separate flow control module may control each pumping system.

Next, a second fluid is drawn by the first pumping system into the microchannels 812 of the interface module 802 to fill the microchannels 812 with the second fluid. For example, in some embodiments, the second fluid may be a different mixture of fluids provided to the interface module 802 as described above with reference to the process 600, such as spacer (blanking) fluid between the PCR reactions. In some preferred embodiments, drawing the second fluid into the microfluidic channels 812 of the interface module does not move the segment of the first fluid that is already in the microfluidic channels 814 of the reaction chip. In some embodiments, this step may be performed by one or more flow control modules. Again it is not necessary that the same second fluid is drawn into each of the microchannels 812 in this step. The second fluid drawn into any one of the microchannels 812 may be different from the second fluid drawn into any of the other microfluidic channels 812.

In a next step, the second pumping system moves a segment of second fluid from the microchannels 812 of the interface module 802 into the microchannels 814 of the reaction chip 804. The segments of second fluid in the microchannels 814 of the reaction chip may be adjacent to the segments of first fluid in the microchannels 814 of the reaction chip. In some embodiments, as the second fluid is drawn into the microfluidic channels 814, the fluid segments of the first fluid within the microfluidic channels 814 are drawn further into the microfluidic channels 814 of the reaction chip 804. In some embodiments, there are no air bubbles between the segments of the first fluid and the segment of the second fluid within the microfluidic channels 814.

After a segment of the second fluid is provided to the microchannels 814 of the reaction chip 804, if more segments are desired for the reaction chip 804, the process can be repeated to provide another segment of the first fluid to the interface module 802. In this way, the process may be used to create fluid segments alternating, for example, between the first and second fluids.

The process has been described above as creating fluid segments alternating between two fluids. As will be understood by those having skill in the art, in some embodiments, the above described methods can be readily adapted to creating segments of three or more different fluids that flow serially through a microfluidic device (e.g., the reaction chip 804).

Figure 40:
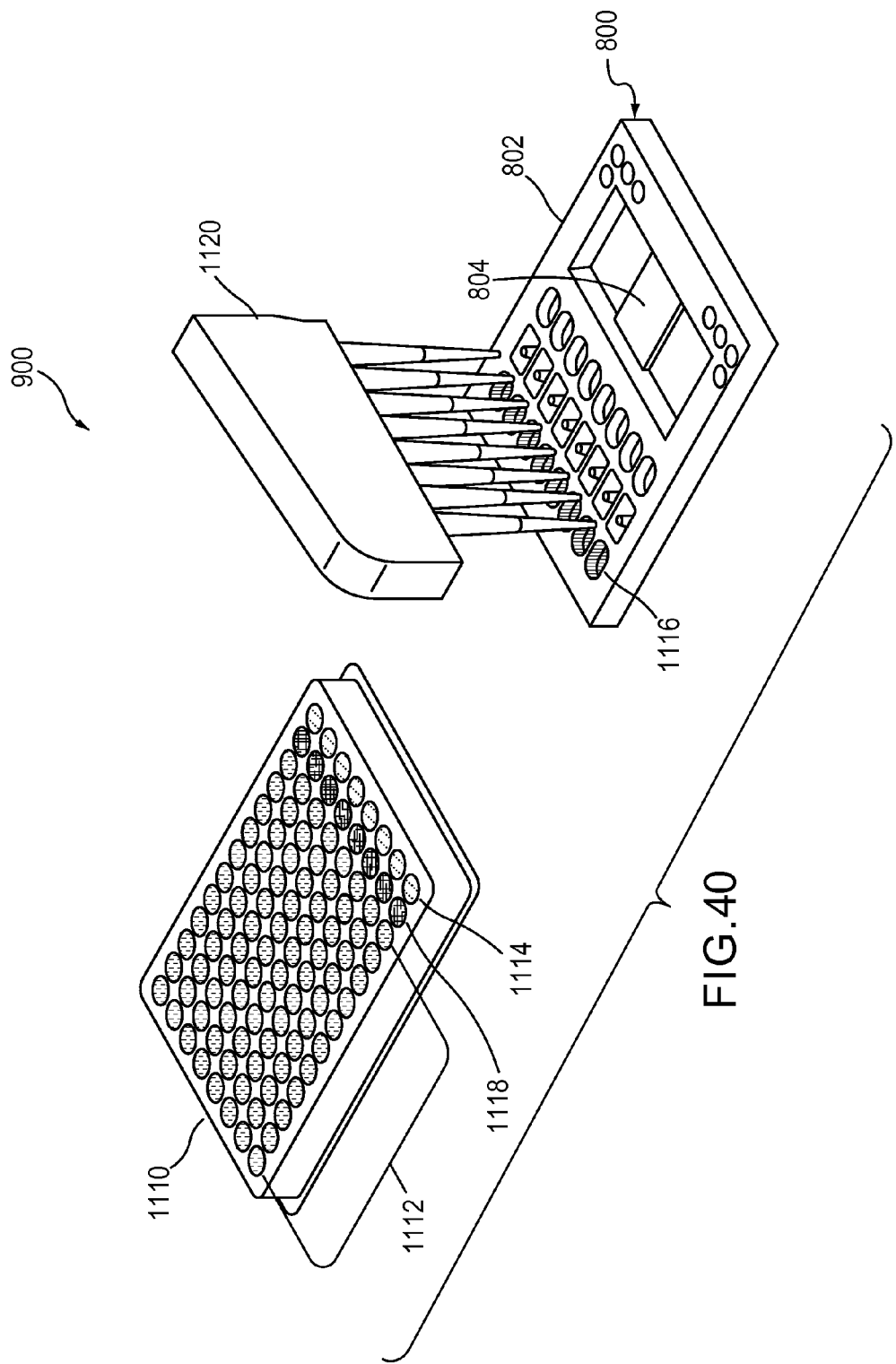
FIG. 40 is a partial perspective view of a fluid handling system and a PCR system according to aspects of the invention.

Using the above methods for reagent selection, mixing, and delivery to a reaction chip, a completely random access microfluidic reaction device can be constructed, whereby patient samples can be assayed using any one of a panel of diagnostic test reagents. FIG. 40 illustrates an embodiment of a random access PCR system 900 according to aspects of the present invention. In some embodiments, the system 900 that may be incorporated into instrument 300 and includes a multi-well sample tray 1110 (which would, in some embodiments, be positioned on platform 316 (see FIG. 5)), one or more pipettes 1120 (e.g., the eight-channel pipette 700 that comprises a component of one or both of the robotic pipettors 308a, 308b), a microfluidic device 800 that includes an interface module 802 and a reaction chip 804 (microfluidic device 322 could also be used). As described elsewhere in this disclosure, the random access PCR system 900 may include one or more additional features of the system 100 and/or system 200 of FIG. 1B, such as a flow control module 208, temperature controllers 210 and 224, and an optical system for recording fluorescence data (e.g., PCR zone flow monitor 218 and thermal melt zone fluorescence measurement unit 232). The sample tray 1110 and the microfluidic device 800 may be carried in the processing drawer 304 of the instrument 300 along with a pipette tip loading and cleaning mechanism 318 carrying a number of pipette tips (e.g., eight pipette tips for the eight channel robotic pipettor or sixteen pipette tips for two eight channel robotic pipettors) that can be engaged by the pipette channels (fluid transfer tubes) of the pipettor 1120 to removably secure a pipette tip onto each channel.

In a process for performing a random access PCR assay, in accordance with one embodiment of the present invention, one or more pipettes 1120 collect a primer liquid 1112, for example, from the micro-well sample tray 1110. In some embodiments, each pipette tip can be independently actuated to collect a different primer liquid 1112.

Next, each pipette 1120 collects a common reagent 1114 from the micro-well tray 110.

Next, each pipette 1120 collects a patient sample 1116. For example, a patient sample 1116 can be stored in a storage well on the interface module 802.

Next, the each pipette mixes the three fluids therein. In some embodiments, this may be accomplished according to step 606 of the process 600 (see FIG. 17), described above.

Next, the mixed fluids are delivered to inlet ports of the interface module 802. In some embodiments, this may be accomplished according to step 608 of the process 600, described above.

Figure 41:
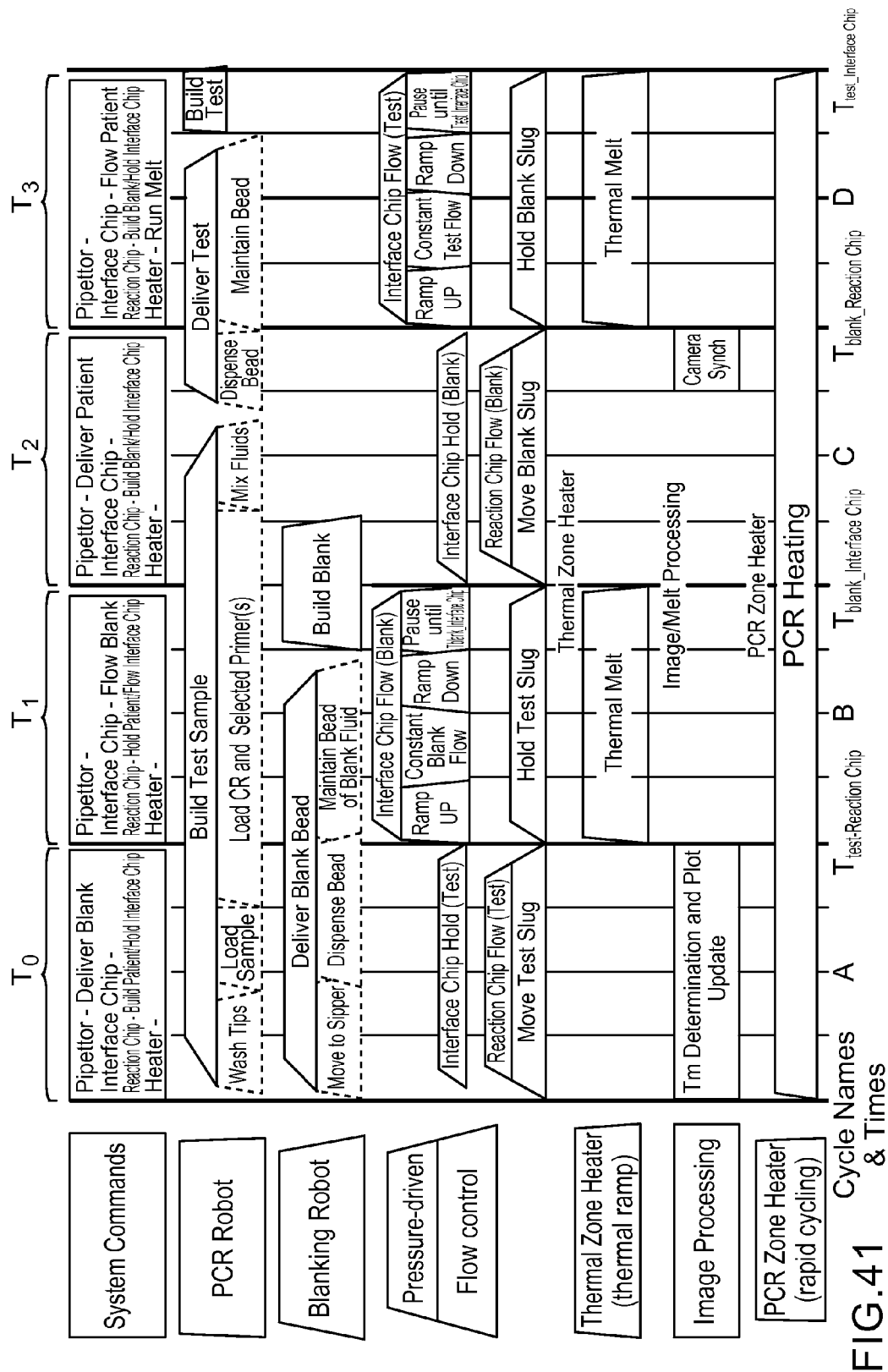
FIG. 41 is a timing diagram for fluid delivery and movement through microfluidic devices according to aspects of the present invention.

FIG. 41 illustrates a timing diagram for a non-limiting example of fluid delivery and fluid movement through a microfluidic device, including an interface module and a reaction chip, in addition to the timing of heating and optical processing according to some embodiments of the present invention. The timing illustrated in FIG. 41 can be used to create a segmented flow in stop and go mode in the reaction chip 804 that allows for both PCR amplification and thermal melt analysis.

Referring to FIGS. 40 and 41, in one embodiment, at time $T_0$, a PCR robot (i.e., an automated controller of pipettes for collecting, mixing, and delivering PCR samples) begins to build a test sample. In some embodiments, this includes washing the pipette tips, loading a sample fluid 1116, loading a common reagent 1114 and selected primers 1112, and mixing the loaded fluids. In a preferred embodiment, the loaded fluids may be mixed by process 600 (FIG. 17).

Also at $T_0$, a blanking robot (i.e., an automated controller of pipettes for collecting, mixing, and delivering PCR samples) may begin to deliver a blank fluid segment that is already present in the pipettes of the blanking robot. In some embodiments, this includes moving the pipettes of the blanking robot to the capillaries of the interface module 802, dispensing beads of blanking fluids 1118 from the pipettes and holding the beads of contact fluid in contact with the capillaries. Examples of suitable blanking fluids include a buffer solution alone, a buffer solution with the sample, or a buffer solution (with or without sample) and a dye such as, Alexa 647, Fluorescien, HPTS, Rhodamine B, Sulforhodamine, Kiton Red, Texas Red, Phloxine B, LDS 698, and 1-4 DHPN. Blanking fluids may also include water, buffer, gas, oil, or non-aqueous liquid. The blanking solution may contain dye if it is necessary to "see" (e.g., image) the blanking solution, but if the blanking solution is used only for separating boluses of test solution, the dye could be included with the test solution for flow tracking purposes. The PCR and blanking robots together are referred to as the pipettor on FIG. 41. The PCR and blanking robots may be embodied in a single pipettor that provides blanking solutions and PCR reagents. Multiple robotic pipettors could be used for timing purposes—one pipettor can be drawing up fluids while the other is dispensing fluids to the microfluidic device.

Also at $T_0$, a flow control module may move a sample segment from the interface module 802 to the reaction chip 804.

At time $T_1$, the PCR robot may be continuing to build the next test sample.

By time $T_1$, the blanking beads from the blanking robot may be ready to be drawn into the microchannels 812 of the interface chip, or module, 802. Therefore, at time $T_1$, the blanking robot may maintain the beads of blanking fluid at the input ports, and a flow control module (e.g., flow control module 208 of the system controller 250 of FIG. 1B) may cause blanking fluid to flow through the input ports and into the microfluidic channels 812 of the interface chip 802 while, in some embodiments, holding the sample fluid from moving in the microfluidic channels 814 of the reaction chip 804. In some embodiments, the system may include a monitor to determine when the microfluidic channels of the interface chip are filled. In these embodiments, the blanking robot may receive a signal when the microfluidic channels 812 are filled with blanking fluid so that the blanking robot can perform other activities.

At time $T_2$, the PCR robot may complete building the test sample (i.e., completes mixing the fluids), and move to the input ports of the interface chip 802 to deliver beads of the samples.

Also at time $T_2$, the blanking robot may build additional blanks (i.e., generates more blanking fluid). In some embodiments, this may be performed only as needed.

Also at time $T_2$, a flow control system may hold the blanking fluid in the microfluidic channels 812 of the interface chip 802 while drawing the blanking fluid into the microfluidic channels 814 of the reaction chip 804 (creating a blanking segment in the reaction chip 804).

By time $T_3$, beads from the PCR robot may be ready to be drawn into the input ports of the interface chip 802. Therefore, at time $T_3$, the PCR robot may maintain the sample beads at the input ports, and a flow control module (e.g., flow control module 208 of system controller 250 of FIG. 1B) may cause the sample fluid to flow through the input ports and into the microfluidic channels 812 of the interface chip 802 while holding the blanking fluid from moving in the microfluidic channels 814 of the reaction chip 804. In some embodiments, the system may include a monitor to determine when the microfluidic channels 814 of the interface chip 802 are filled. In these embodiments, the PCR robot may receive a signal when the microfluidic channels 812 are filled with sample fluid so that the PCR robot can perform other activities.

In some embodiments, the PCR zone temperature controller 210 (see FIG. 1B) may continue to perform rapid PCR heat cycling throughout the time period illustrated in FIG. 41. It is also possible that the PCR cycling is only occurring during some steps in the process (e.g. PCR cycling may occur when the sample slug is in the middle of the PCR Zone or PCR cycling may not occur during thermal melt). Additionally, in some embodiments, the thermal melt zone temperature controller 224 (see FIG. 1B) may perform a thermal melt ramp during one of the above time periods. That is, depending on the number of fluid segments in the microchannels 814 of the reaction chip 804, in some embodiments, a sample fluid segment will be in a thermal melt zone of the reaction chip 804 (e.g., thermal melt zone 242 of the microfluidic device 240 of the system 200 in FIG. 1B) during one or more of the time periods described above. Therefore, the thermal melt zone ramp may be provided by the thermal melt zone temperature controller during one of the time periods during which a sample fluid segment is within the thermal melt zone.

Figure 42:
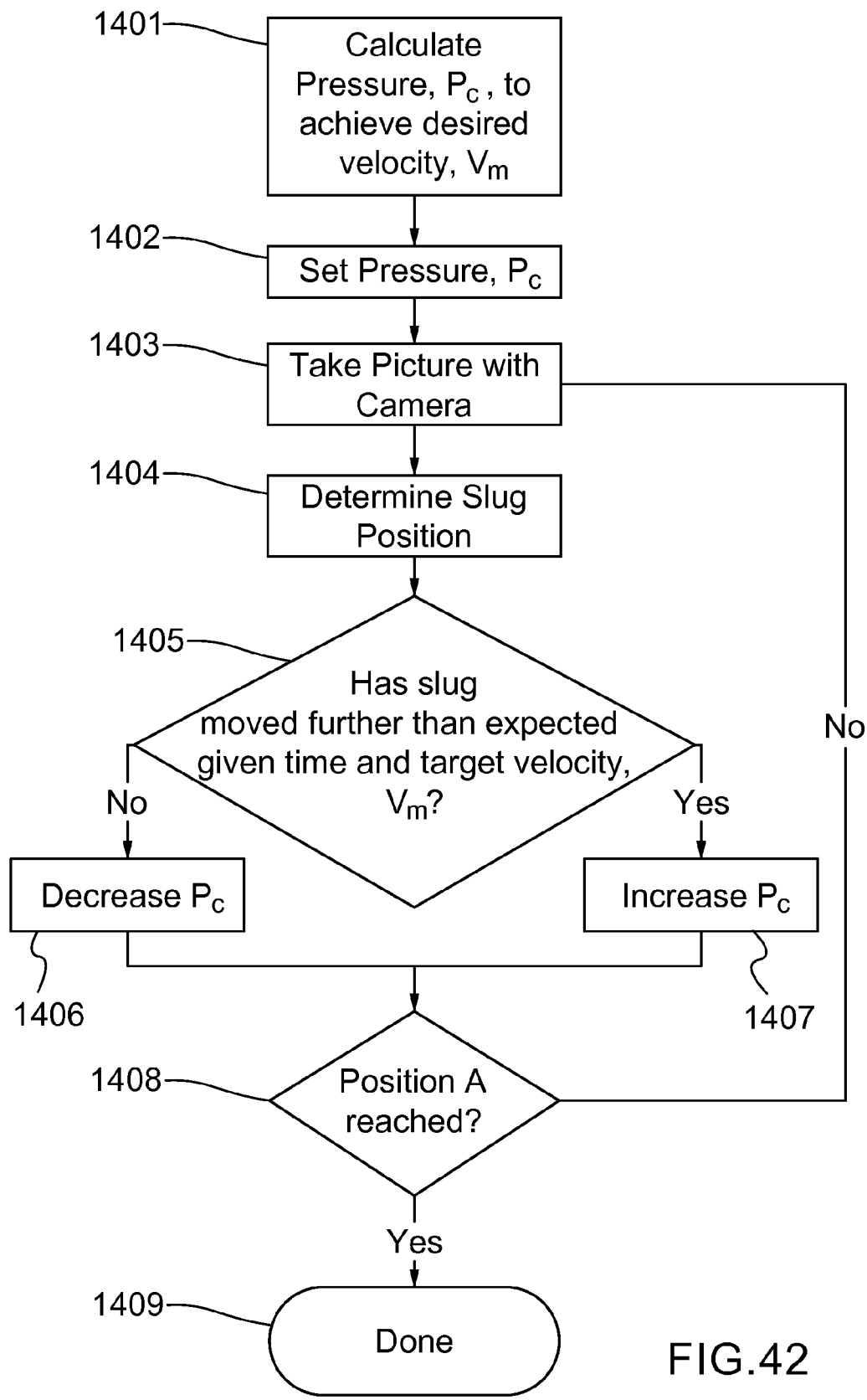
FIG. 42 is a flow chart illustrating a process for tracking and controlling the moving of fluid segments through a microfluidic device according to aspects of the present invention.

Furthermore, image processing may be employed as necessary to obtain accurate position information of the fluid segments and accurate data for thermal melt analysis. FIG. 42 is a flow chart illustrating an embodiment of a process for utilizing image processing to track the location and movement of the fluid segments. In Step 1401, a flow module (e.g., a flow control module of system controller 250) may compute initial pressure $P_c$ to force a slug to travel in the desired direction at velocity $V_m$. In step 1402, the flow control module may drive pumps (e.g., pump module 114, see FIG. 1A) and monitor pressure sensors (e.g., sensor 116, see FIG. 1A) until the pressure sensors measure the desired pressure $P_c$. In step 1403, an image trigger may be sent out and an image capturing device (e.g., image capturing device 118b of imaging system 118 of system 100 of FIG. 1A) returns an image of the slug. In step 1404, the image may be analyzed to find slug features and to determine the location of the slug. In step 1405, the flow control module may determine whether the slug position as a function of time (i.e., the target velocity) is too high or too low and will cause the process to move to step 1406 or 1407. If the target velocity is too high in comparison to a desired velocity, the flow control module may move to step 1406. If the target velocity is too low in comparison to a desired velocity, the flow control module 208 may move to step 1407. In step 1406, the analysis of step 1405 determined that the slug was moving too fast in comparison to a desired velocity, and the flow control module 208 may then decrease the pressure setpoint $P_c$. In step 1407, the analysis of step 1405 determined that the slug was moving too slowly in comparison to a desired velocity, and the flow control module 208 then increases pressure setpoint $P_c$. In step 1408, system controller 250 may determine whether the slug is located in the desired position. If so, the movement process is complete, otherwise, the system controller 250 will continue the process with step 1403. In some embodiments, when the slug is in the desired position, the pressure control system switches into a position maintenance mode instead of velocity control. Although some processes depicted in FIG. 42 have been described as being the function of the flow control module 208 or the system controller 250, it is envisioned that the actual controller that implements these steps may vary depending on variations in programming and system architecture, including as described below in FIG. 43.

Furthermore, in some embodiments, each time fluid segments are moved, the position of each fluid segment may be verified (e.g., via the PCR zone flow monitor 218). In one non-limiting embodiment, if any fluid segments are not within a specified percentage of their target locations, such as, for example 25%, the affected channel is disabled for further tests. Other percentages could also be used.

Figure 43:
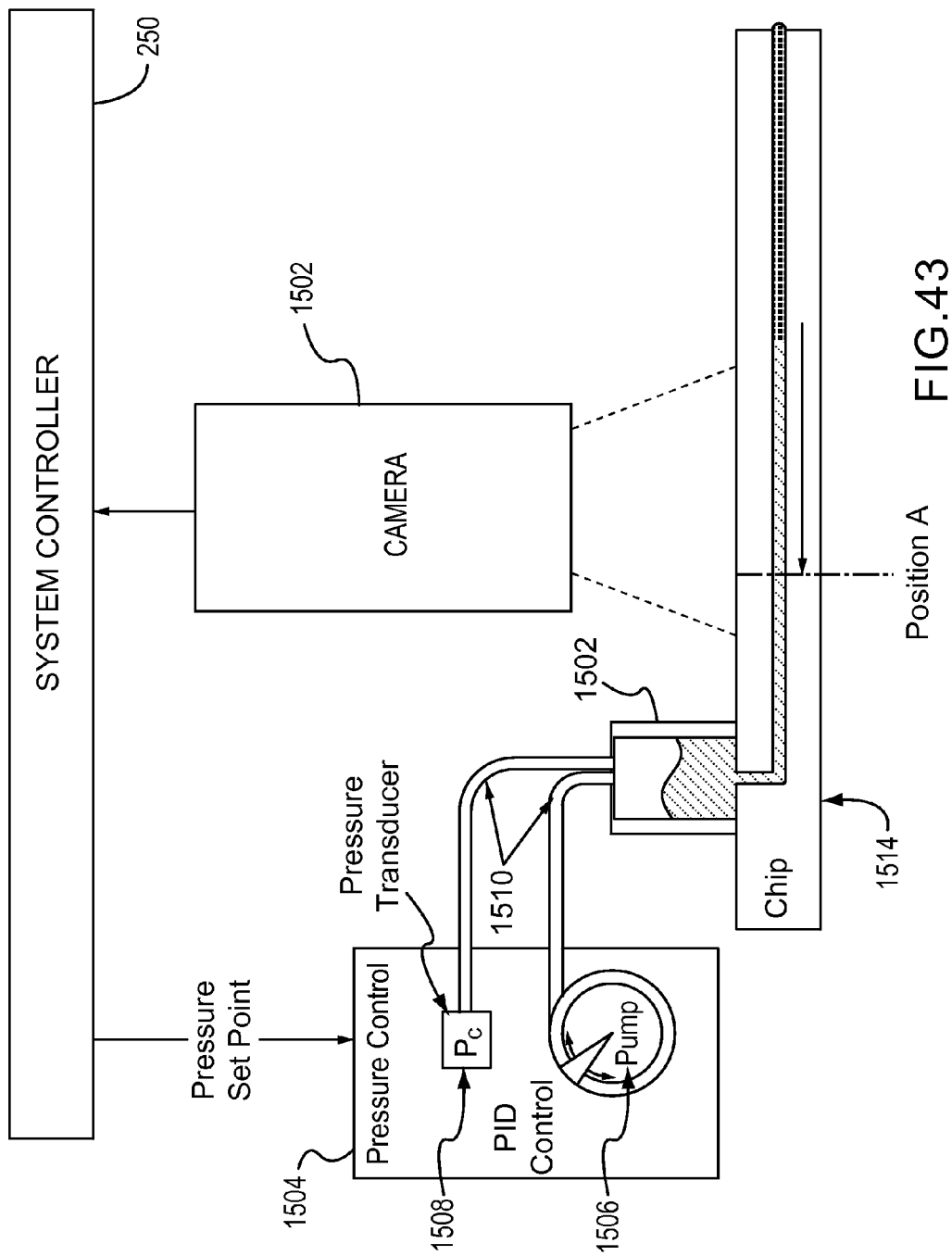
FIG. 43 is a schematic diagram illustrating components of a flow control system for controlling the moving of fluid in a microfluidic device according to aspects of the present invention.

FIG. 43 is a block diagram of a flow control system that can be used in the process depicted in FIG. 42 or in other embodiments of the present invention. System controller 250 may interface with an image capturing device 1502 (e.g., image capturing device 118b of imaging system 118 of system 100 of FIG. 1A or detection element 222 or 236 of FIG. 1B, such as a camera) to send an image trigger and to receive an image in response. The system controller 250 may request pressure readings from a pressure controller 1504, which may be implemented using a printed circuit board (PCB), and will send the desired pressure setpoint values to one or more pumps 1506 (which may correspond to system pump module 114, see FIG. 1A) of the pressure controller 1504. The pressure controller 1504 may run a local control loop to cause the one or more pumps 1506 to maintain the desired pressure sent by the system controller 250. The pressure controller 1504 may use a pressure transducer 1508 (which may correspond to system pressure sensor 116, see FIG. 1A) to detect pressure. Pump tubing 1510 may be connected to fluid wells or reservoirs 1512 (e.g., reservoirs or wells 502) on a microfluidic device, or chip or cartridge, 1514 (e.g., interface module 802 or reaction chip 804 coupled to the interface module, see FIG. 39) to force liquids to flow in the desired direction.

Figure 44:
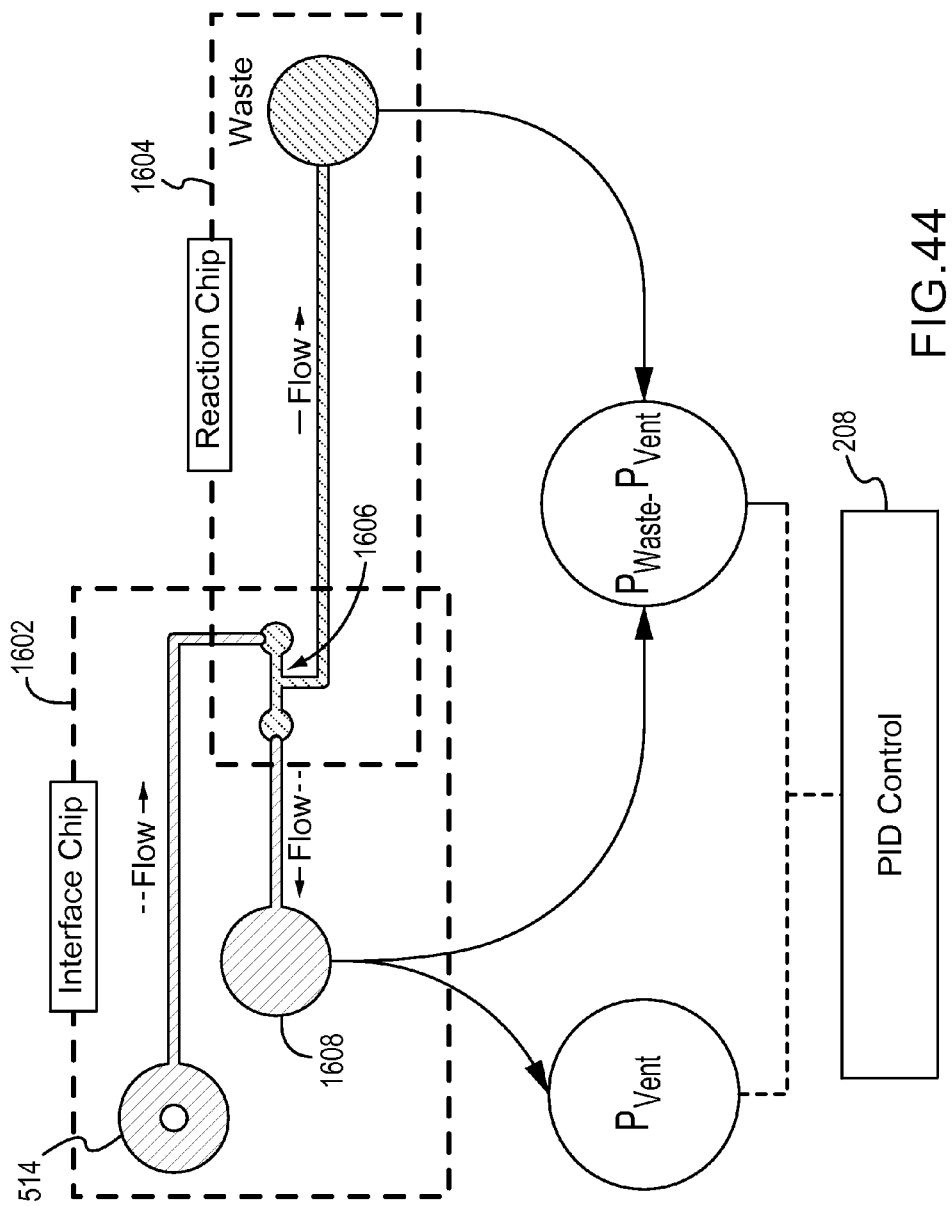
FIG. 44 is a schematic diagram illustrating a flow control system for moving fluid segments through a microfluidic device according to aspects of the present invention.

FIG. 44 illustrates an embodiment of a mechanism for controlling the flow of fluid in a system. A capillary or sipper 514 is present in an interface module 1602 (e.g., interface module 802) at atmospheric pressure with a drop of fluid located at an end. The drop may be applied via the methods and systems described above. The system controller 250 will set a negative pressure at a vent well to cause fluid to flow from microchannel 514, through the interface module 1602 (e.g., interface module 802) onto the reaction chip 1604 (e.g., reaction chip 804) and through a "T" junction 1606 present in the reaction chip. Pressures may be controlled via a pump controlled by a flow control module (PID control) 208. The fluid will then flow back out of the reaction chip onto the interface module and to the vent well 1608. During this process, the pressure control system controls the waste pressure to maintain the slug in a fixed position in the reaction chip. When the "T" junction 1606 and surrounding area of the interface chip 1602 are loaded with fluid, the system controller 250 will stop the fluid flow in the interface chip 1602. The system controller 250 will then start the fluid flow in the reaction chip 1604 to move the slug to desired location. Once the slug has reached the desired location, the system controller 250 will cause the fluid flow to stop in the reaction chip 1604, and the system controller 250 can cause the pipetting system 202 (FIG. 1B) to place a new drop of fluid on the microchannel 514. The system controller 250 can then cause the process to begin and loop until all desired slugs have been created.

In one aspect of the present invention, the T-junction between an interface chip and a reaction chip can be utilized to create alternating slugs of multiple fluids while decreasing the amount of diffusion between the slugs, as is described in U.S. Patent Application Publication No. 2011-0091877, entitled "Systems And Methods For Minimization Or Elimination Of Diffusion Effects In A Microfluidic System," hereby incorporated by reference herein in its entirety. The present invention therefore may include a method of collecting, from a continuous flow of two or more miscible fluids sequentially present in a channel, one or more samples that are substantially free from contamination by the other miscible fluids present in the channel. In one embodiment, the method may comprise the steps of: a. identifying and monitoring the position of a diffusion region between uncontaminated portions of a first miscible fluid and a second miscible fluid in a first channel; b. diverting the diffusion region into a second channel; and c. collecting a portion of the second miscible fluid which is substantially free from contamination by any miscible fluids adjacent to the second miscible fluid.

Although FIGS. 43 and 44 illustrate examples of a flow control system and mechanism for controlling the flow of fluid, respectively, that may be used in embodiments of the present invention, use of the particular system and mechanism illustrated in FIGS. 43 and 44 is not required and other systems and mechanisms may be used.

A microfluidic device comprising flow through channels that may be used in connection with systems and methods of the present invention may include features other than, or in addition to, those described above.

For example, the microfluidic device can be configured, implemented, and/or used in association with compositions and methods for in-system priming of the microfluidic device, as described in U.S. Provisional Patent Application No. 61/378,543, entitled "Composition And Method For In-System Priming Microfluidic Devices" and U.S. application Ser. No. 13/221,948 claiming priority therefrom the disclosures of which are hereby incorporated by reference. The composition for in-system priming provides a priming solution for dry priming microfluidic chips. The priming solution has high wettability, is PCR compatible, and enables higher PCR efficiency. In one embodiment, the priming solution comprises a conventional 1×PCR buffer with an increased concentration of surfactant. The surfactant in the PCR buffer is increased by adding a surfactant to the PCR buffer or by increasing the concentration of the surfactant in the PCR buffer Furthermore, the microfluidic device can be configured, implemented, and/or used in association with systems and methods for minimizing and/or eliminating diffusion effects in a microfluidic system having one or more channels, so that concentration-dependent measurements can be made on a segmented flow of multiple miscible fluids in the one or more channels, as described in U.S. Patent Application Publication No. 2011-0091877, entitled "Systems And Methods For Minimization Or Elimination Of Diffusion Effects In A Microfluidic System," the disclosure of which is hereby incorporated by reference. The system includes a microchannel configuration in which diffused regions of a segmented flow of multiple, miscible fluid species may be vented off to a waste channel, and non-diffused regions of fluid may be preferentially pulled off the channel that contains the segmented flow. Multiple fluid samples that are not contaminated via diffusion may be collected for analysis and measurement in a single channel. The systems and methods for minimizing or eliminating diffusion effects may be used to minimize or eliminate diffusion effects in a microfluidic system for monitoring the amplification of DNA molecules and the dissociation behavior of the DNA molecules.

Furthermore, the microfluidic device can be configured, implemented, and/or used in association with systems and methods for preventing undesired materials from contaminating an assay performed in a microfluidic channel, as described in U.S. Patent Application Publication No. 2009-0325159, entitled "System And Method To Prevent Cross-Contamination In Assays Performed In A Microfluidic Channel," the disclosure of which is hereby incorporated by reference. A buffer of non-reactive fluid is provided between an input port and a microchannel in which assays are performed during such times that flow from the input port is stopped. In general, an amount of non-reactive fluid is drawn into a channel connecting the stopped input port to the microchannel. Thus, any seepage, or diffusion, from the channel connecting the stopped input port to the microchannel will be of the non-reactive fluid, not the reagent, or other potentially-contaminating fluid, introduced through the input port. Microvalves and a negative pressure differential source control flow of reagents into the microchannel and the flow of non-reactive fluid into the inlet conduits.

Furthermore, the microfluidic device can be configured, implemented, and/or used in association with systems, methods, and/or apparatus for mixing materials within channels of a microfluidic device, as described in International Patent Publication No. WO 2010/118430; entitled "A Method Of Delivering PCR Solution To Microfluidic PCR Chamber," the disclosure of which is hereby incorporated by reference. Systems and methods are provided for performing in-line mixing of assay components and delivery of such mixed components into microfluidic channels. In one aspect, a method comprises causing an unmixed primer solution, comprising a common reagent and a primer, to flow into a first mixing channel. The unmixed primer solution is held in the first mixing channel for at least a threshold amount of time to allow the unmixed primer solution to transition into a mixed primer solution. A buffer, comprising the common reagent but not including a primer, is caused to flow into a second mixing channel after holding the unmixed primer solution in the first mixing channel for at least the threshold amount of time. The mixed primer solution is drawn from the first mixing channel into a common exit channel, and after drawing the mixed primer solution into the exit channel, the buffer is drawn from the second mixing channel, into the common exit channel.

Figure 12:
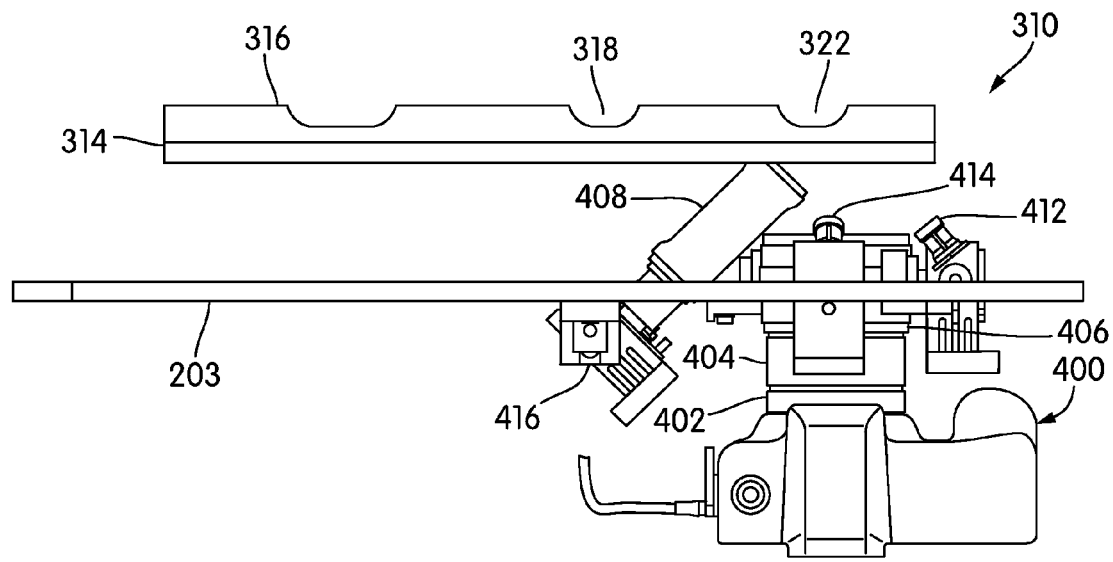
FIG. 12 is a front view of an optical imaging system in relation to a removable tray of the instrument of FIG. 4 according to one embodiment.

Referring back to the exemplary embodiment illustrated in FIG. 4, the optical system 310 is configured to be located directly below the location for the microfluidic device 322. FIG. 12 illustrates a front view of an imaging system that may be implemented as the optical system 310 in relation to the tray 314 according to one embodiment. The imaging system includes a sensor (e.g., a camera) 400 anchored beneath a mounting plate 203 of the frame chassis 202. A lens barrel 406 and/or extension tubes 402 and 404 extend through the mounting plate 203. LEDs 408, 410, 412, 414 are also mounted on the mounting plate 203. According to one embodiment of the present invention the LEDs 408, 410, 412, 414 are mounted on the upper surface of the mounting plate 203.

As further illustrated in FIG. 12, according to one non-limiting embodiment, the detector can be a digital color camera that is capable of recording data at video frames rates, such as, for example, 20-30 frames per second. A non-limiting example would be the Canon EOS 5DMkII Digital SLR camera. The lens assembly preferably includes an appropriate fluorescence emission filter. In this exemplary embodiment, the emission filter is a dual bandpass filter with a pass-band for the DNA binding dye LC Green Plus from Idaho Technology and a pass-band for a red flow tracking dye such as Alexa Fluor 647 from Life Technologies. However, alternative filters may be substituted for appropriate alternative combinations of fluorescent dyes. Excitation may be provided by several different high-powered LEDs as shown.

Other details of imaging systems that may be used in connection with the systems and methods of the present invention, as well as further details regarding their use, are described in U.S. Provisional Patent Application No. 61/378,471, entitled "Optical System For High Resolution Thermal Melt Detection," and U.S. application Ser. No. 13/222,487 claiming priority therefrom, the disclosures of which are hereby incorporated by reference.

According to an embodiment, optical system 310 of the instrument 300 comprises a CMOS sensor that, in one embodiment, may comprise part of an off-the-shelf digital single-lens reflex (DSLR) camera, which has a large format CMOS sensor (such as, for example, 24 mm×36 mm). The field of view is much larger than prior systems that employ microscope lenses and allows imaging of the entire microfluidic chip. The optical system 310 could be used as the imaging system 118 of the system 100 of FIG. 1A or the excitation elements 220, 234 and detection elements 222, 236 of system 200 of FIG. 1B. and could be used for both flow tracking of the microfluidic system and thermal melt signal detection.

Methods for flow tracking, e.g., measuring flow rate through the micro channels 104a, 104b of the system 100 of FIG. 1A, are described in U.S. Pat. No. 7,629,124. A method for flow tracking is also shown in FIG. 42. For example, in one embodiment, the average flow rate is measured by comparing sequential images of the reaction-dependent fluorescent signal from the channel. In a second embodiment, the average flow rate is measured by comparing sequential images of a reaction-independent flow marker from the channel. More specifically, the system acquires one or more images of the contents of the channel. These image data and the time of acquisition are stored to a database for subsequent analysis. A feature of two or more sequential images—e.g., reaction-dependent fluorescent signal from the channel or reaction-independent flow marker from the channel—may be compared to determine how far the fluid has moved along the channel from one image to a subsequent image. Dividing the average displacement by the elapsed time gives an average flow speed. In another embodiment, scattered light from the reaction-independent flow marker is resolvable from the reaction-dependent fluorescence by wavelength spectrum. In an alternative embodiment, scattered light from the reaction-independent flow marker is resolvable from the reaction-dependent fluorescence on the basis of fluorescence lifetime. In another embodiment, the reaction-independent flow marker is further used to determine the flow dispersion of the test bolus. In a further embodiment, the image of reaction-dependent fluorescence is captured at least once per PCR cycle. In one embodiment, the image of reaction-dependent fluorescence is captured sequentially by scanning a length of the channel on a time scale shorter than the duration of one PCR cycle. In an alternative embodiment, the image of reaction-dependent fluorescence is captured by acquiring signals from multiple points along the channel simultaneously. In another embodiment, the flow rate measurements are part of a feedback loop for regulating the flow rate. In a further embodiment, the flow rate is measured through detecting a sample bolus entrance into and exit from a defined section of the channel.

In some embodiments, the determined flow rate may be used as an input to control the pump module 114, via the main controller 130, in a feedback flow control loop.

In an embodiment of the imaging system, a digital single-lens reflex (DSLR) camera is employed for high resolution thermal melt and flow tracking in microfluidic chips. In a non-limiting example, the DSLR camera can be a Canon EOS 5D Mark II. The DSLR camera is also suitable to acquire real-time PCR information (as described, for example, in U.S. Pat. No. 7,629,124) when applicable. Usually, digital cameras save pictures in RAW or JPEG format. To achieve a fast frame rate, JPEG format is usually adopted. In one non-limiting embodiment, the DSLR camera has a CMOS sensor of 24 mm×36 mm, with a pixel array of 5616×3744 arranged in a Bayer pattern (2 Green, 1 Blue, 1 Red sub-pixel for each pixel).

To record fluorescence change over time during DNA thermal melt, a high frame rate is preferred. In one embodiment, the detector can be a digital color camera that is capable of recording data at video frames rates, such as, for example, 20-30 frames per second. The live view function of a suitable DSLR camera, such as, for example, the Canon EOS 5D Mark II, provides a frame rate of 30 fps. Of course, a suitable DSLR camera with a higher or lower frame rate may be used as well in certain embodiments. In a non-limiting example, files from the live view function are saved in JPEG format with two choices of resolutions:

a. full sensor images with sub-sampled pixels, image size 1120×752 (1× zoom); and b. a crop of the sensor with full pixel resolution, image size 1024×680 (5× zoom).

In one embodiment, the 1× zoom is used for flow tracking, since it images a relatively large area (at a reduced pixel density), which may include portions of the microfluidic chip where PCR and thermal melt occur and part of an interface chip coupled to the microfluidic chip for liquid handling. In one embodiment, the 5× zoom is used for thermal melt detection where increased resolution (detail) of a small portion of the microfluidic chip is required. In a preferred embodiment, all the pixels in the imaged area are preserved so better signal to noise ratio (SNR) can be achieved. In other embodiments, a different zoom setting could be used for either flow tracking or thermal melt detection.

JPEG image format offers 8-bit resolution, i.e., 256 digital levels for each pixel. In some embodiments, more bit depth could be achieved by averaging many pixels in the region of interest ("ROI") to achieve greater than 8-bit resolution.

As described in the U.S. Pat. No. 7,593,560, the pixel array of the sensor may be divided into zones of interest corresponding to particular ROI's. That is, the image sensor has the ability to read out or "window" a predefined portion of the pixel array (this is known as "windowing"). For thermal melt imaging, the melting zone 136 (see FIG. 1A) of the micro-channel 104a, 104b is uniformly illuminated with a high power LED and is imaged into the CMOS sensor with ~1:1 ratio. In the melting zone 136 where thermal melt is measured, the fluorescence intensity is calculated by averaging the JPEG values of all the pixels in the ROI. In one embodiment, fluorescence intensity is calculated by averaging JPEG values of >2000 pixels. By averaging pixel JPEG values (8-bit) of an ROI with numerous pixels, better than 11 bit resolution could be achieved.

Another benefit from averaging the pixels in the ROI is to improve signal-to-noise ratio ("SNR").

Fluorescence from LC Green (DNA binding dye used for high resolution melting) is nearly equally sensed by green and blue pixels of the CMOS sensor. Thus, the average of the green and blue pixels is used to represent the fluorescence intensity on that specific pixel of the sensor. Because of the Bayer filter in front of the sensor in accordance with one embodiment, in each pixel there are 2 green pixels and 1 blue pixel. Accordingly:

$$\text{Pixel fluorescence intensity} = (2*\text{Green} + 1*\text{Blue})/3.$$

In reality, the weight of Green and Blue may deviate from the 2:1 ratio due to other camera settings. One such setting that can affect the Green to Blue ratio is white balance. White balance manipulates green, blue, and red pixel JPEG values to adapt the image to different illumination conditions. Using SNR as a metric, optimized condition of white balance settings and green, blue ratio could be calculated or measured.

Figure 18:
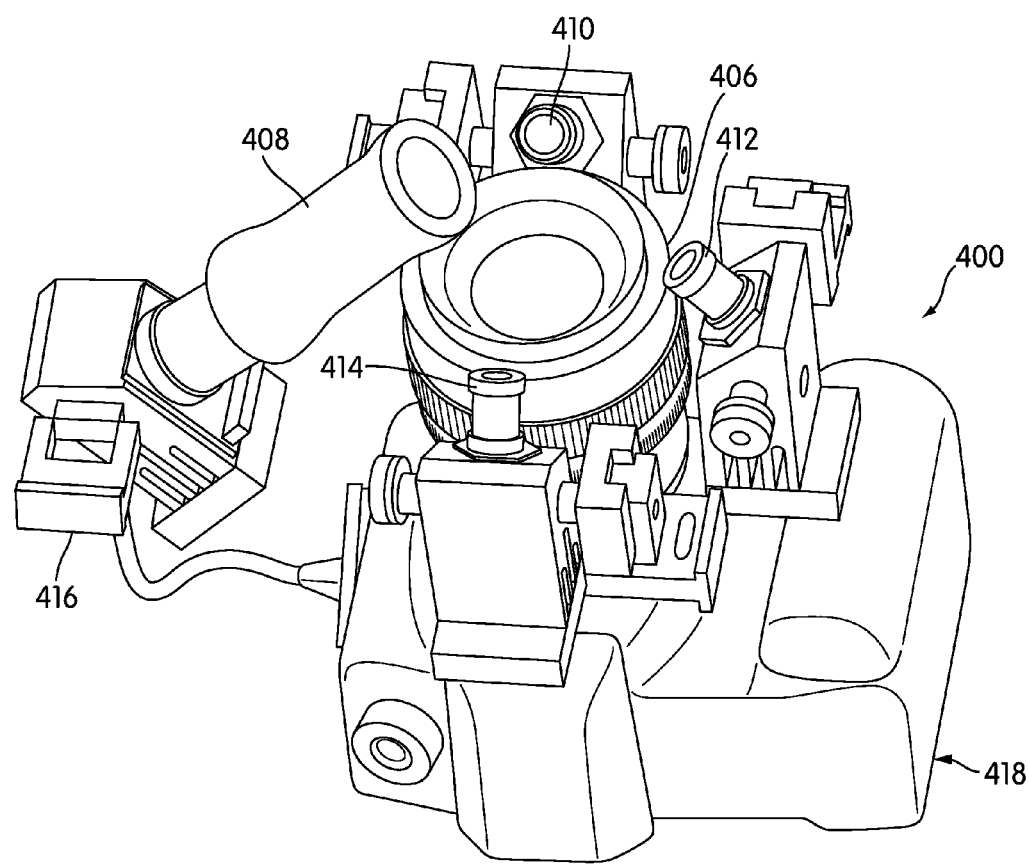
FIG. 18 is a perspective view of an imaging system, including a sensor and LED layout, that may be used in association with the present invention.
Figure 19:
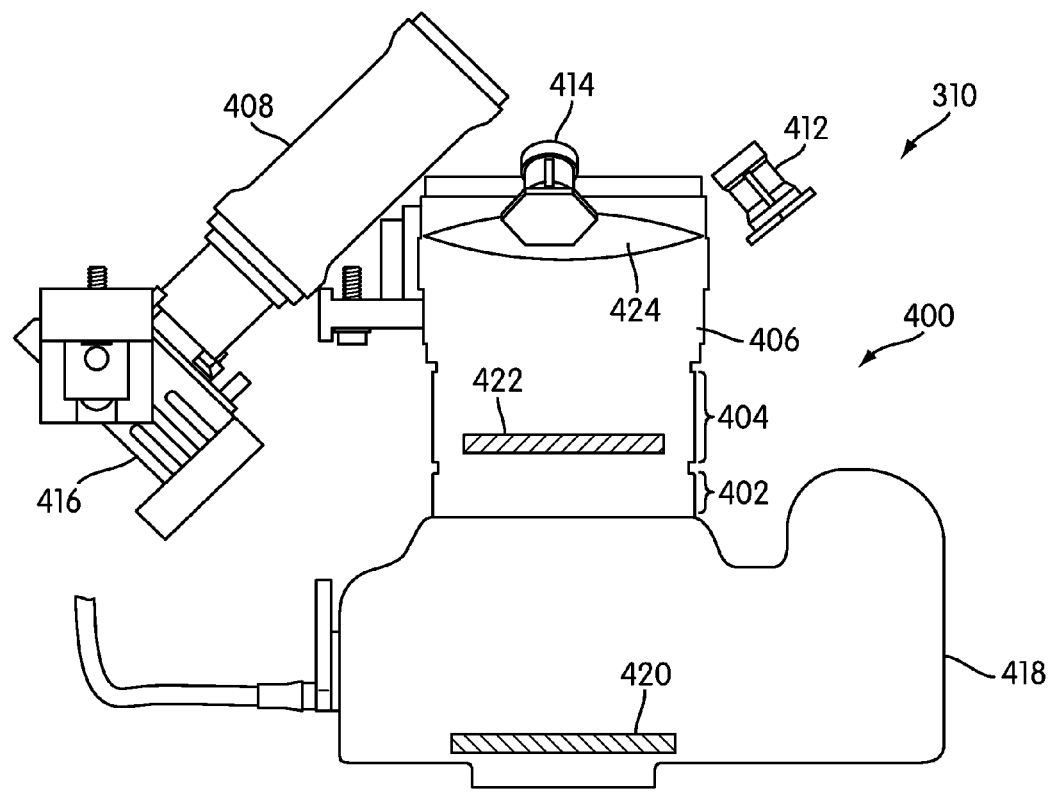
FIG. 19 is a side view of the imaging system, including a sensor and LED layout, that may be used in association with the present invention.

An imaging system 310, according to an embodiment of the invention, is shown in FIGS. 12, 18 and 19. The imaging system 310 includes a CMOS sensor 420, which, in one embodiment, is provided within a camera 400, for example, a DSLR camera, such as the Canon EOS 5D Mark II, which may include a camera body 418 (which houses the CMOS sensor 420) and a lens barrel 406 containing one or more lenses 424. In embodiments of the invention, the imaging system 310 may be used for thermal melt measurement and flow tracking. In one embodiment, the imaging system 310 is configured to generate and record multiple images per second for flow tracking and thermal melt analysis. For example, the Canon EOS 5D Mark II includes a live view mode that is used to generate and record JPEG images at ~1 Hz for flow tracking purposes while boluses flow in microfluidic channels. It could also be used for real-time PCR purposes. In certain embodiments, for thermal melt data recording, images, such as JPEG files, are recorded at ~30 Hz rate, with integration time ~33 ms. Other recording rates and integration times also may be used.

In one embodiment, an F/1.4 lens may be used for greater photon collection. Lenses with smaller F/# have higher light collection capability.

Extension tubes 402, 404 may be used to make the distance between lens 424 and the microfluidic device 322 to be imaged as close as possible. Light collection is proportional to the square of distance between lens and fluorescence source. In one embodiment, the extension tubes have lengths of 25 mm and 12 mm, for a total extension length of 37 mm, which can make the distance between lens 424 and the microfluidic device 322 to be imaged as close as about 6 cm.

The sensor may include a dual band emission filter 422, which may be fitted in one of the extension tubes 402, 404 to allow only selected wavelengths to reach the sensor. In one embodiment, the filter is configured to allow only fluorescence from LC Green and Alexa 647 (or Texas Red) tracking dye to reach the sensor. In one exemplary embodiment, the emission filter is a dual bandpass filter with a pass-band for the DNA binding dye LC Green Plus from Idaho Technology and a pass-band for a red flow tracking dye such as AlexaFluor 647 from Life Technologies. However, alternative filters may be substituted for appropriate alternative combinations of fluorescent dyes. Fluorescence from LC Green has a blue-green color that is sensed by both blue and green pixels of the CMOS sensor. However, because the camera's green filter will block blue photons, and the camera's blue filter will block green photons, at least half of the photons are rejected by either filter. In one embodiment, the filter has a shifted spectrum (e.g., to the blue-green wavelength) so all the photons could pass the filter to reach the sensor pixels. The camera's red filter can be kept unchanged so the 'dual color' sensor can still do both flow tracking and thermal melt detection with two different dyes.

In one embodiment, the imaging system 10 includes four LEDs 408, 410, 412, 414 for illumination of the microfluidic chip. The LEDs are excitation sources that generate light at desired wavelengths to excite labels used for detecting amplification products during real-time PCR, dissociation behavior during thermal melt analysis, and/or to detect markers that may be present to monitor the flow rate of the test solution in microchannel 104a and/or 104b. As explained above, PCR zone 138 of the chip is for PCR, and melting zone 136 is for thermal melt (see FIG. 1A). An embodiment of the layout of the sensor 400 and LEDs 408, 410, 412, 414, of the imaging device 310 is shown in FIGS. 18 and 19. FIG. 18 is an illustration of an imaging device 310, including the sensor (e.g., camera) 400 and the LED layout. As shown in the illustrated embodiment, the LEDs 408, 410, 412, 414 are arranged adjacent to the lens barrel 406 at 90° angular intervals around the lens 424. LEDs 410 and 414 are disposed opposite each other with respect to the lens 424, and LEDs 408 and 412 are disposed opposite each other with respect to the lens 424.

In an exemplary embodiment, LED 408 comprises an assembly with a slot aperture and an imaging lens and is positioned and oriented for melting zone 136 (thermal melt) illumination. LED 410 and LED 414 are positioned and oriented for PCR zone 138 (PCR) heater calibration and can also be used to monitor PCR process and melt in zone 138 if necessary. LED 412 is positioned and oriented to excite flow tracking dye in the whole chip 102 (microfluidic chip 328). In one embodiment, a goal is to limit illumination of LED 412 to PCR zone 138, thus avoid photobleaching in melting zone 136 when doing thermal melt.

Figure 20:
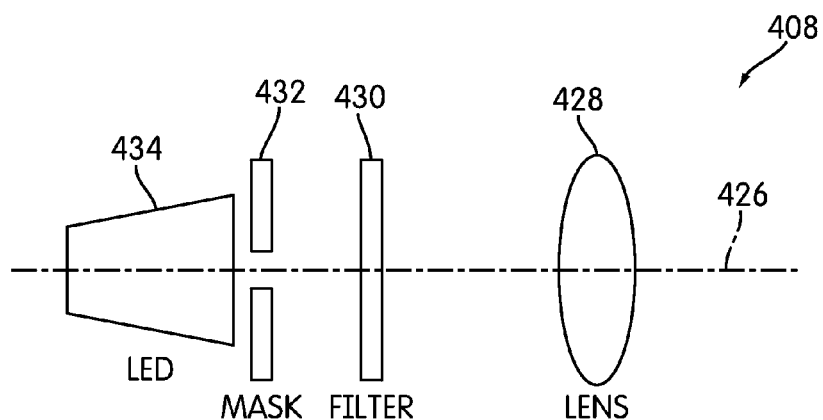
FIG. 20 is a schematic view of an LED assembly of the imaging system that may be used in association with the present invention.

FIG. 20 is a schematic view of the melting zone 136 LED (LED 408) assembly in accordance with one embodiment. As shown in FIG. 20, LED 408 is actually an assembly that includes an LED 434, a mask 432, a filter 430, and a lens 428 aligned along an optic axis 426. As shown in FIG. 20, it is within the scope of the invention that the optic axis 426 may continue behind the lens 428. Although not depicted, the filter 430 can be placed on either side of the lens 428, depending on the specific conditions desired for the application. For instance, the filter 430 can be used to reflect light when placed behind the lens 428. Mask 432 includes a slot for limiting the illumination from the LED 434 to thermal melt zone 136 of the microfluidic chip 102. Filter 430 controls the spectral content of excitation light directed at the chip 102, and lens 428 images the light band onto melting zone 136. Melting zone 136 is illuminated with the band shape light from the mask 432 of the LED assembly 408. With the band-shaped light, this LED (blue LED) illuminates only melting zone 136, so as to avoid photobleaching of the dye in PCR zone 138. The assembly may also include heat sinks and fans 416.

In one embodiment, two high-powered blue LEDs (410, 414) are placed at both sides of PCR zone 138 to excite LC Green in zone 138 for heater calibration. In an embodiment of a system for nucleic acid analyses using a microfluidic chip with one or more micro-channels, the heating element may comprise metal wires or filaments disposed adjacent to the micro-channels, for example, as disclosed in U.S. Patent Application Publication No. 2009-0248349 entitled "Microfluidic Devices With Integrated Resistive Heater Electrodes Including Systems And Methods For Controlling And Measuring The Temperature Of Such Heater Electrodes" and U.S. Patent Application Publication No. 2011-0048547 entitled "Microfluidic Systems And Methods For Thermal Control," the disclosures of which are hereby incorporated by reference in their entireties.

In one embodiment, LEDs 410 and 414 are disposed on opposite sides of the microfluidic chip 102 (microfluidic chip 328) to avoid shadow in PCR zone 138 due to the heater elements. Additionally, this disposition of LEDs 410 and 414 creates more uniform illumination across all channels. Heater calibration can be performed by passing a substance with a known nucleic acid concentration through a microchannel 104a, 104b, illuminating PCR zone 138 with LEDs 410 and 414 and generating thermal melt curves that are compared to expected thermal melt curves for the known nucleic acid concentration. In some embodiments, LEDs 410 and 414 could also be used to monitor PCR and/or thermal melt in zones 138 and 136, respectively.

In one embodiment, LED 412 (red LED) flood illuminates the whole chip 102, which can be used for flow tracking purposes. In some embodiments, the LEDs may be turned on selectively. For example, the LED 408 is only turned on for melt tracking.

In preferred embodiments, all of the LEDs 408, 410, 412, 414 and the sensor 400 are facing up, and the transparent side of the microfluidic chip 102 (328) faces down. This arrangement allows a liquid handling system (e.g., robotic pipetter) to use the space above the chip 102 (328) with minimal obstacles.

In preferred embodiments, LEDs 408, 410, 412, 414 are controlled by a controller 118c of the imaging system 118 and/or the main controller 130 executing control algorithms written, in one non-limiting example, in Labview from National Instruments. Other control algorithms also can be used as would be known by persons skilled in the art.

It is understood that the CMOS sensor 420 of imaging system 310 need not be a DSLR camera. In embodiments of the present invention, the CMOS sensor of imaging system 10 can be another suitable sensor having the characteristics described herein.

When heaters are not uniform, only a small portion of melting zone 136 can be used as the ROI (the thermally uniform portion). Typically, the uniform portion of melting zone 136 corresponds to that part of melting zone 136 heated by calibrated heating elements, and the non-uniform, fringe portions of melting zone 136 include non-calibrated heating elements. An effectively larger ROI can be created under conditions of non-uniform heating by dividing the non-uniform ROI portion of melting zone 136 into several smaller "sub-ROIs", each of which is small enough to have a uniform temperature. In some embodiments, melt curves are plotted for each small sub-ROI and are then shifted to the temperature calibrated region in the ROI mathematically to correlate the melt curves of the non-calibrated sub-ROIs with the melt curve of the ROI of the calibrated portion of melting zone 136. SNR could be improved with the larger effective ROI.

Reference fluorescence materials could be placed near the sample (without interfering with the fluorescence from the sample) so that fluctuations from the light source can be identified and removed. That is, fluctuations from the expected fluorescence signal of the reference fluorescence materials can be identified so that corrections in the fluorescence signal measured from the sample material can be made. In addition, the reference fluorescence materials could be used to identify whether distortion is from the light source or a heater when debugging the system. That is, distortions that exhibit in both the reference fluorescence materials and the sample materials are likely due to excitation light source distortions, whereas distortions that exhibit in the sample materials but not in reference fluorescence materials are likely due to distortions in the heater. Such reference materials could be any fluorescence material that can be excited and detected by the imaging system 10. Suitable, non-limiting examples include Sytox blue, CFP, Alexa 647, Cy5, BODIPY650/665, or various quantum dots. In addition, the plastics in the microfluidic fixture could be used as fluorescence reference too.

In one embodiment, glue (e.g., Lens Bond Type SK-9 available from Summers Optical of Hatfield, Pa.) used to bond the microfluidic-chip and a heat sink can be used as reference.

The reference fluorescence material can be chosen to be temperature dependent. Heater fluctuation can be identified and removed using such reference fluorescence material. When proper materials are chosen which have temperature dependent fluorescence intensity (fluorescence intensity of most dyes is temperature dependent, such as Alexa Fluor 647, fluorescein, et al), the temperature fluctuation of the heaters can be monitored using the fluorescence of the reference dye. When a heater temperature changes, the fluorescence intensity of the reference dyes will follow the temperature changes. When the reference materials has strong enough intensity and large enough area, the fluorescence signal from the reference material measurement will have a sufficiently high SNR so the change in fluorescence intensity could reflect the heater temperature fluctuations. Error caused by a heater can be removed by data processing using the information acquired from the thermal sensitive reference materials, e.g., varying fluorescent intensity. The reference material need to be placed close enough to the heaters for this purposes. The temperature dependence does not need to be same as the sample under measurement.

In some embodiments, only one detector is needed to measure both the sample fluorescence and reference fluorescence.

In one embodiment, thermal melt data is recorded by the imaging system 118 (optical system 310) as a function of time (JPEGs are saved with their time stamps as file name). Temperature is also recorded by the temperature control system 120 as a function of time. This creates two data sets: an image vs. time data set and a temperature vs. time data set. Preferably, these two sets of data are synchronized accurately to give the correct melt temperature.

There are many ways to synchronize two independent data sets. In one embodiment, with a DSLR, a signal can be sent from a PC to the remote shooting control port of the camera to take a static image right before thermal melt is started. For example, the static image signal can be sent at the same time the initial heater signal is sent. Thus, both the images and the heaters will have the same start time. The time the static image is taken has a known relation with both the PC time (temperature time) and camera live view image time stamps, so the temperature and images can be synchronized, in some cases to within <30 ms resolution. When imaging a uniform object, the images usually are not ideally uniform. The center will have higher intensity then the edges. In order to make melt data better, the microfluidic chip can be shifted so that melting zone 136 (where thermal melt occurs) is as close to the center of image as possible.

Still other details of fluorescence imaging systems and methods that may be used in connection with the systems and methods of the present invention, as well as further details regarding their use, are described in U.S. Provisional Patent Application No. 61/378,558, entitled "Slug Control During Thermal Cycling," and U.S. application Ser. No. 13/222,887 claiming priority therefrom, the disclosures of which are hereby incorporated by reference, which describes system and method for controlling slugs (i.e., boluses of fluid reaction mixture) that include temperature dependent fluorescent dye during thermal cycling by, for example, enhancing the ability of a system to determine the position of a slug within a microfluidic channel.

Some embodiments of systems and methods for compensating for temperature dependence include a saturation approach, in which the intensity of the blanking slugs' fluorescence is maximized, for example, by increasing the intensity of blanking slug excitation light source. The intensity of the blanking slugs can also, or alternatively, be increased by increasing the concentration of dye within the blanking slugs. The saturation approach makes the blanking slugs fluoresce so brightly that they saturate the sensor despite variations in fluorescence that may occur, for example, due to temperature or other changes.

In another embodiment, the temperature dependence of the fluorescent dyes may be overcome by modulating the intensity of the excitation light (i.e., "light modulation"). For instance, if the red blanking slug is excited by a laser or LED, the power of output of the excitation source can be increased or decreased (e.g., by adjusting the current and/or voltage) as necessary to maintain an approximately constant fluorescence intensity despite variations in temperature. For example, in a non-limiting embodiment, the fluorescence of the dye can decrease as the temperature of the reaction increases. To compensate for this, the power output of the excitation source can be appropriately increased as the temperature of the reaction increases to maintain an approximately constant fluorescence intensity.

Light modulation can be implemented in a variety of ways in accordance with aspects of the invention. For example, in some embodiments, software determines the temperature of the dye (e.g., the PCR zone temperature controller 210 or the thermal melt zone temperature controller 224 (see FIG. 1B) knows the temperature of the corresponding zone and thus can determine the temperature of the dye). In a non-limiting embodiment, the light power is varied by using an analog output on a data acquisition card. In another embodiment, an excitation laser or LED can be modulated using hardware feedback. For example, if a circuit is used to measure the temperature of a sensor on the microfluidic device (e.g., a resistance temperature detector whose voltage and current are measured), then signals from that circuit can be used as inputs to vary the LED or laser power. In yet another embodiment, the excitation source can be turned on and off at different duty cycles (i.e., pulse width modulated) to maintain an approximately constant fluorescence intensity during varying temperatures.

In another non-limiting embodiment, a laser or other appropriately imaged and focused excitation source can be used to create an excitation stripe across a plurality of microchannels so that the slugs fluoresce brightly in the area of the excitation stripe. In a preferred embodiment, the excitation stripe would be placed in a small area of nominally constant temperature so that the fluorescence of slugs in the excitation stripe would not vary and the slugs could remain under control despite temperature variation in other areas of the channel. In some embodiments, the focused excitation could also be used to saturate the imaging system as described above.

In another embodiment, a laser (or other appropriately imaged and focused light source) can be used to photobleach a spot or stripe into the dye. In this manner, the photobleached spot or stripe can be tracked since the florescence of the dark spot will not vary. Tracking a photobleached spot or stripe could be used to track slugs, but this technique will be less sensitive to temperature variation only if the edges of the photobleached spot or stripe are sharper than the edges of diffused slugs.

After one or more images of the slug are acquired, a signal processing step is implemented, which includes a normalization process.

Embodiments of the normalization approach include scaling the threshold based on the range of intensities observed in the ROI. Some embodiments can be implemented by analyzing fluorescence values in the pixels of the image acquired that correspond to the ROI, determining the peak intensity in the ROI, and determining the scaling factor S required to bring that peak to the maximum intensity of the sensor (e.g., in an 8-bit image, determining the scaling factor S required to scale the maximum intensity in the ROI to 255). In some embodiments, the scaling factor S can be determined by dividing the maximum intensity of the sensor (e.g., 255 in an 8-bit sensor) by the maximum intensity observed in the ROI. The normalization process can then scale the intensity values in the entire region of interest and then use a threshold intensity to determine the edge of a slug within the region of interest.

Still other details of fluorescence imaging systems and methods that may be used in connection with the systems and methods of the present invention, as well as further details regarding their use, are described in U.S. Provisional Patent Application No. 61/378,700, entitled "Slug Control During Thermal Cycling," and U.S. application Ser. No. 13/222,887 claiming priority therefrom, the disclosures of which are hereby incorporated by reference, which describes systems and method for controlling slugs using temperature dependent fluorescent dyes in polymerase chain reaction (PCR) thermal cycling applications. In some embodiments, one or more techniques to enhance the visibility of slugs, enhance a system's ability to differentiate between slugs, and enhance a system's ability to identify the positions of slugs are described.

For example, if in the software the user sets a threshold of 50%, the threshold intensity will be 127 (in the 8-bit system), and the edge of a slug will be detected where pixels cross that threshold (i.e., where pixels transition from values below 127 to values above 127). In some embodiments, the particles identified in the ROI by a threshold detection method may be filtered (e.g., using a low-pass spatial filter or a noise reduction filter) to make a smooth edge to better facilitate slug control by ignoring dust or other image artifacts.

In further embodiments, the normalization method may also include scaling the minimum intensity as an alternative to, or in addition to, scaling the maximum. In this case, the scaling factor S will be based on the span between the maximum and minimum intensities observed in the ROI. In this case, it is preferable that the ROI only include information corresponding to the microfluidic channel (i.e., the ROI should not include dark pixels corresponding to areas outside the microchannel, or bright pixels caused by dust on the microfluidic chip).

Furthermore, in some embodiments the control system may be configured to check the span of intensities in the ROI to verify that a minimum span is present in the ROI. This feature is preferable for determining whether a slug edge is present in the ROI because it can ensure that the slug control system is not tricked by the normalization.

In another non-limiting embodiment, the normalization approach may use an average of the bright pixels in the ROI for determining the maximum intensity value in the ROI and an average of the dark pixels in the ROI for determining the minimum intensity value of the ROI. This can, for example, be implemented using a fixed number of pixels (e.g., the mean intensity of the brightest ten pixels) or using the distribution of intensities such as a histogram.

In another embodiment, the normalization may include areas outside the region of interest for the purposes of determining the maximum intensity value and the minimum intensity value. This may be preferable when the slugs are smaller than the region of interest.

In another embodiment, the normalization may use the maximum and standard deviation of intensity values for determining the appropriate threshold.

Signal processing may also include a color thresholding process. That is, in some embodiments, the slugs can be controlled by determining the edges or slug positions using more than one color plane of the image acquired. An embodiment incorporating this aspect may be preferable when the colors used in adjacent slugs are similar or appear similar because of the imaging system (e.g., cross-talk). National Instrument's Labview software includes a color thresholding function that may be appropriate for some embodiments. In further embodiments, color thresholding can be used in combination with the normalization process described above.

Other details of fluorescence imaging systems that may be used in connection with the systems and methods of the present invention, as well as further details regarding their use, are described in U.S. Patent Application Publication No. 2008/0003594 (U.S. Pat. No. 7,906,319 entitled "Systems And Methods For Monitoring The Amplification And Dissociation Behavior Of DNA Molecules," the disclosures of which are hereby incorporated by reference.

Figure 13:
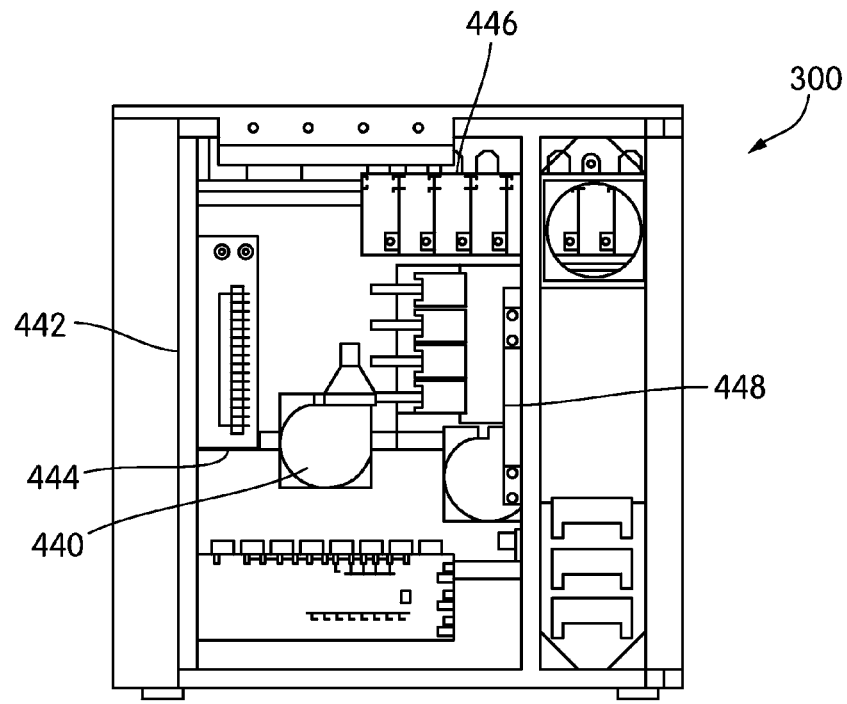
FIG. 13 is a rear, cutaway view of an instrument showing additional components of the instrument according to one embodiment.

Referring now to FIG. 13, a rear view of the instrument 300 is illustrated which includes several features which are not visible from the perspective shown in FIG. 4. In the illustrated embodiment, FIG. 13 includes a blower 440, a bank of peristaltic pumps 442, a pressure measurement and control circuit board 444, a bank of syringes 546 (for use with a robot pipettor 308a, 308b), and a power supply 448.

Several banks of syringe pumps 546 are illustrated in accordance with one exemplary embodiment. In the illustrated embodiment, the pumps are connected via tubing (not shown) to the robotic pipettors and are used to draw small volumes (such as, for example, in the range of 0.1 µL to 10 µL) of liquids into and out of the pipette tips. In one non-limiting example, suitable syringe pumps are available from Tricontinent.

A bank of peristaltic pumps 442 are connected to the vacuum manifold via tubing (not shown). Pumps 442 may correspond to pump module 114 of system 100 shown in FIG. 1A, and the vacuum manifold may correspond to manifold 112 in FIG. 1A. In one non-limiting example, suitable peristaltic pumps are available from Watson-Marlow. In the non-limiting embodiment shown, there are sixteen total pumps, eight for vent wells (to pull liquids into the upstream end of the 8-channel microfluidic chip) and eight for the waste wells (used to pull liquids through the microfluidic chip). The peristaltic pumps 442 can apply positive or negative pressures relative to atmospheric pressure. These pumps are used to control pressure via a feedback system implemented in a pressure measurement and control circuit board. However, the pressure target set points are adjusted regularly by the system controller based on data on the slug position obtain by the fluorescence imaging system 310.

Other details of pressure measurement and control systems for applying variable pneumatic pressures to the microfluidic device that may be used in connection with the systems and methods of the present invention are described in U.S. Patent Application Publication No. 2009/0325159.

Still other details of pressure measurement and control systems for applying variable pneumatic pressures to the microfluidic device that may be used in connection with the systems and methods of the present invention are described in U.S. Patent Application Publication No. 2009/0320930 entitled "System And Method For Microfluidic Flow Control," the disclosure of which is hereby incorporated by reference.

In one embodiment, when positioned inside the instrument, the microfluidic device 322 mates to a cooling manifold/connector assembly 306 that performs several functions. In one embodiment, the manifold/connector assembly 306 provides electrical connections to allow resistive heating power delivery and temperature sensing. The manifold/connector assembly 306 also provides sealed pneumatic connections to apply pressure or vacuum to the microfluidic channels within the cartridge, and a duct for forced cooling air for cooling the microfluidic device 322. In the embodiment shown, these connections are made to the top side of the microfluidic device 322. FIG. 13 illustrates a blower that connects to the manifold assembly 306 to provide forced air cooling to the microfluidic device in accordance with one embodiment. Systems and methods for cooling that are suitable for incorporation in the present invention can be configured, implemented, and/or used in association with systems, methods, and/or apparatus for isolating the cooling air from exposed liquids by using confinement channels, as described in U.S. Provisional Patent Application No. 61/378,467, entitled "Air Cooling System For Microfluidic Devices," and U.S. application Ser. No. 13/222,565 claiming priority therefrom, the disclosures of which are hereby incorporated by reference.

Figure 21A:
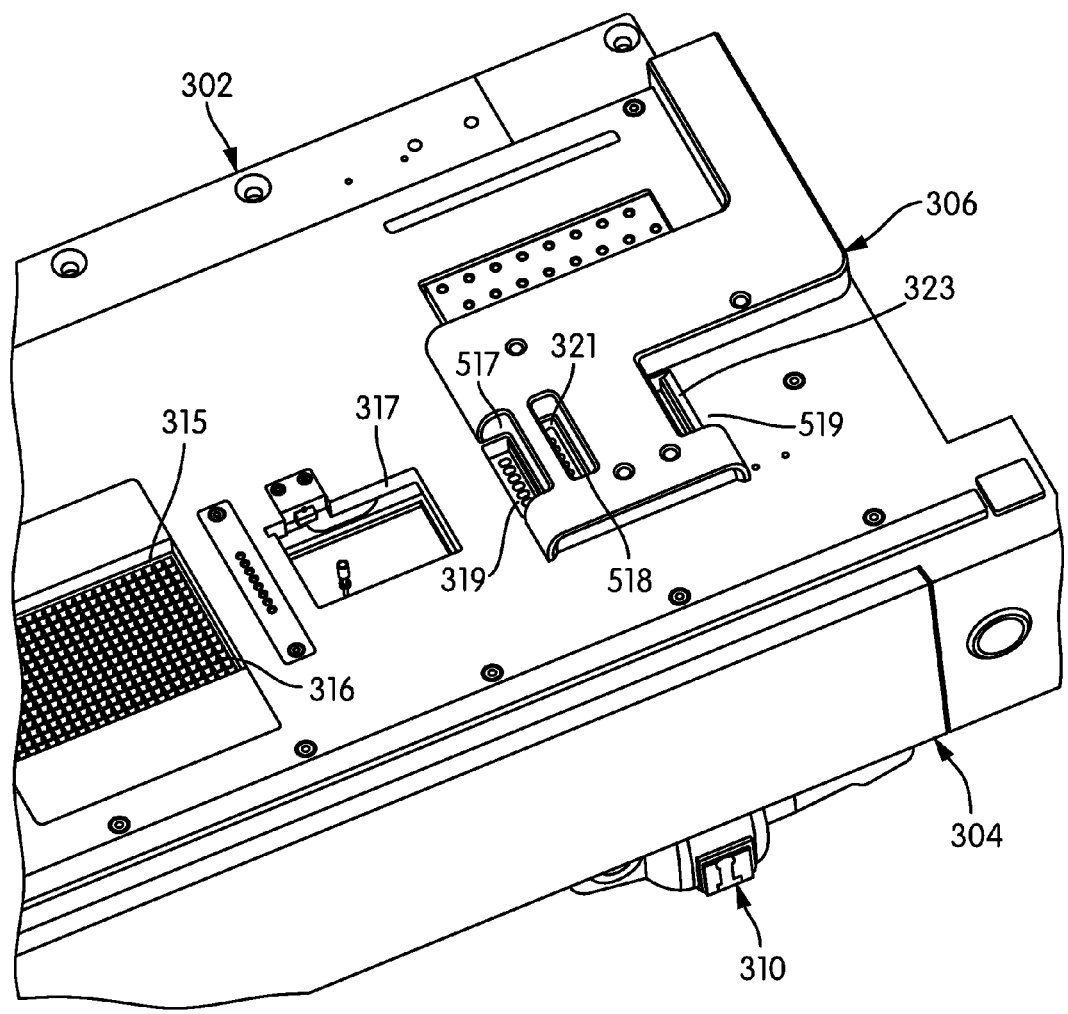
FIG. 21A is a partial perspective top view of the instrument of FIG. 4 illustrating a split-level cooling manifold according to one embodiment.

FIG. 21A shows the cooling manifold 306 located above the microfluidic device 322 contained in processing drawer 304 in accordance with one embodiment. Cooling manifold may be configured to direct air to and/or from microfluidic device 322. Cooling manifold 306 may have a ports 517, 518, 519 that align with access openings 319, 321, 323, respectively, formed in the shelf of the frame chassis 302 or in the manifold itself above the drawer 304 and that allow fluid access or interface to the microfluidic device, e.g., by pipettors 308a and 308b. As shown in FIG. 21A, each of ports 517, 518, and 519 may be an opening extending through cooling manifold 306 to allow liquids to be delivered to the microfluidic device 322 without being disturbed by the cooling airflow. In other words, in some embodiments, the liquids may be exposed when being delivered to the one or more inlet ports of the microfluidic device 322, and the cooling manifold 306 isolates the cooling airflow from the exposed liquids at the inlet ports. Liquids can also be exposed at the one or more outlet ports. The cooling manifold 306 may, alternatively or in addition, isolate the cooling airflow from exposed liquids at the one or more outlet ports.

In one embodiment, cooling manifold 306 may utilize a split level design such that inlet and outlet air streams are segregated into different ducts within the manifold. This enables warm air that is heated by the microfluidic device 322 to be directed away from microfluidic device 322. For instance, the air heated by the microfluidic device 322 may be directed outside the instrument to isolate the airflow from liquids and prevent heat build-up within the instrument. In directing the heated air away from the microfluidic device 322, cooling manifold 306 may direct the heated air to a rear enclosure 1037 (see FIG. 27), which is isolated from the front of instrument 300 shown in FIG. 4.

Figure 22:
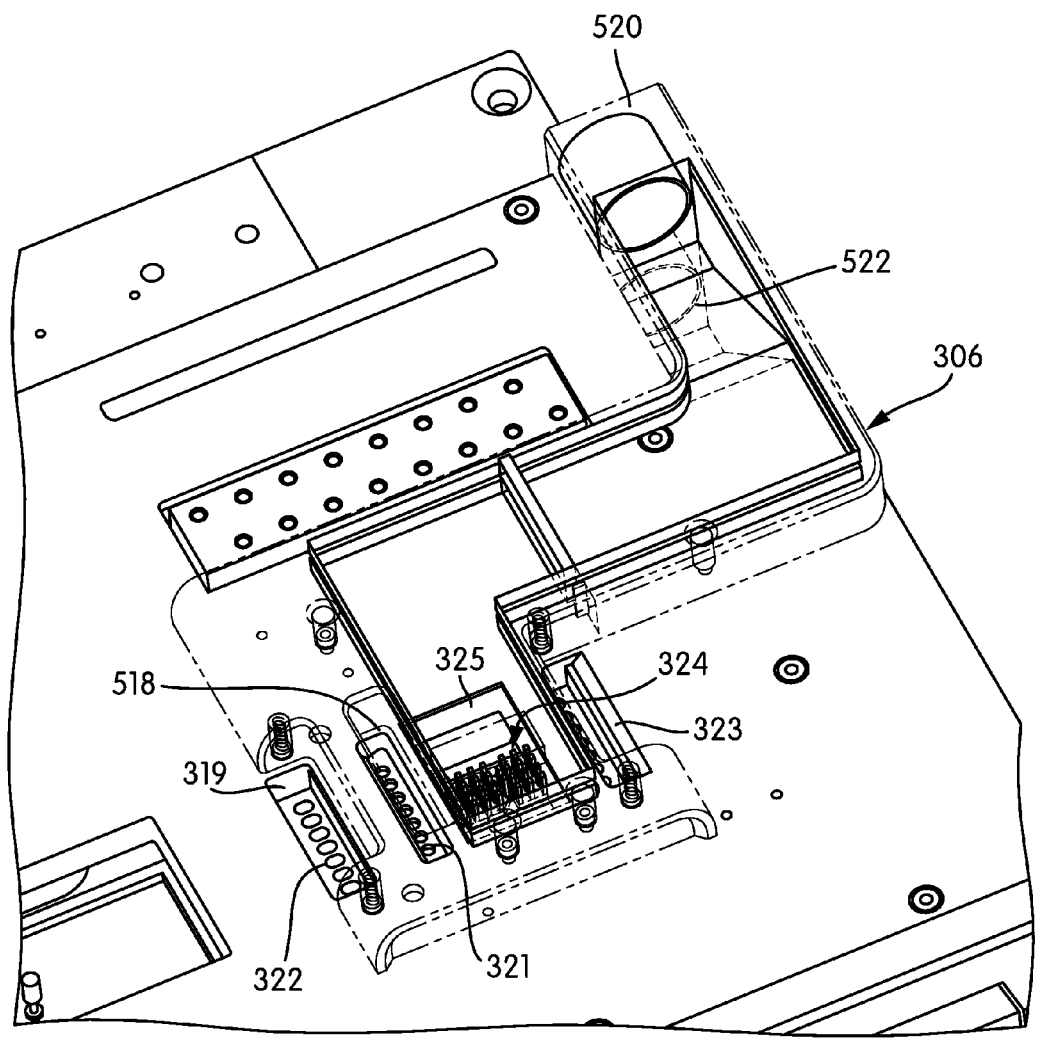
FIG. 22 is a partial perspective top view, with certain components shown as transparent, of the split-level cooling manifold of FIG. 21A showing the relationship of the split-level cooling manifold and microfluidic device according to one embodiment.
Figure 23A:
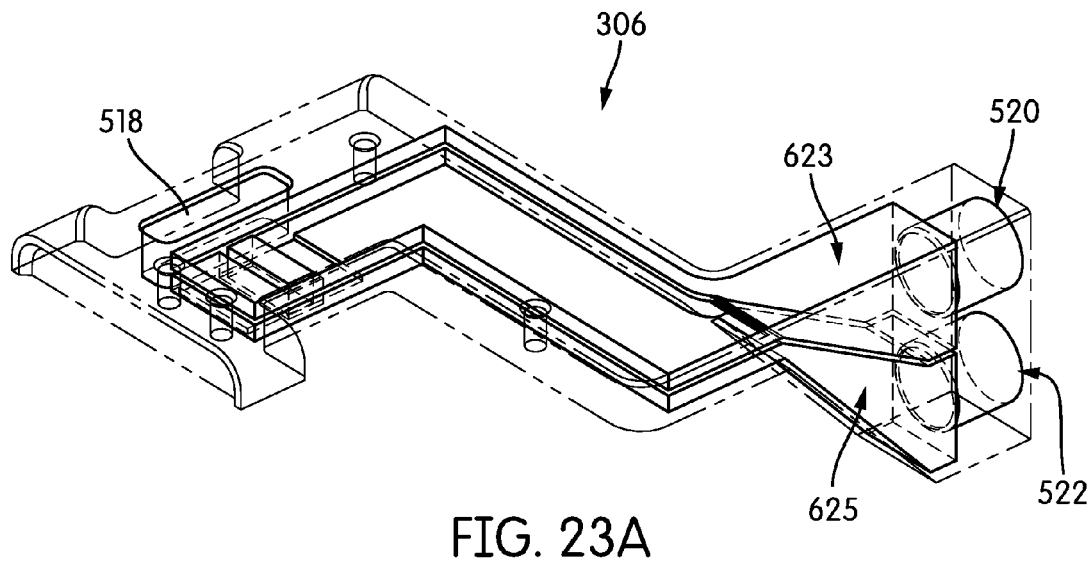
FIG. 23A is a perspective, partially transparent view of the split-level cooling manifold of FIG. 21A illustrating inlet (i.e., top) and outlet (i.e., bottom) ducts thereof according to one embodiment.
Figure 23B:
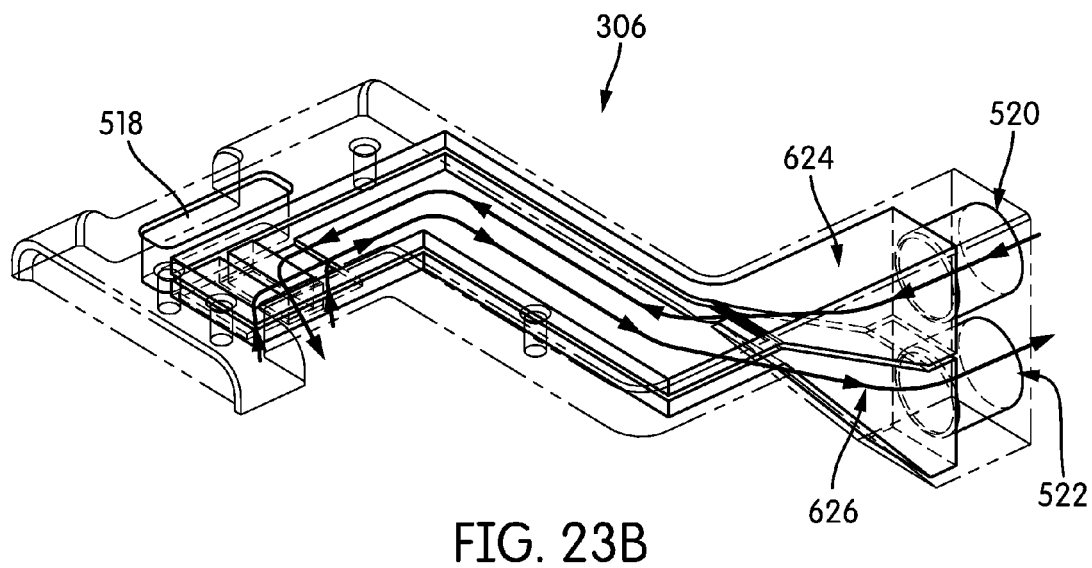
FIG. 23B is a perspective, partially transparent view of the split-level cooling manifold of FIG. 21A illustrating airflow through the inlet and outlet ducts of FIG. 23A according to one embodiment.
Figure 24A:
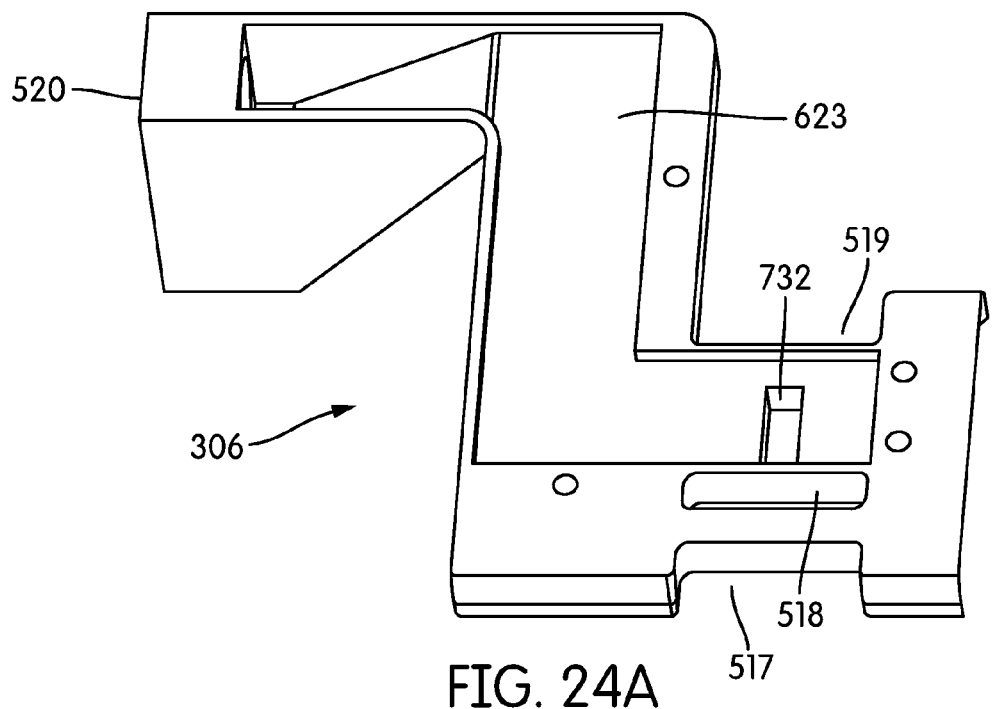
FIGS. 24A and 24B are partial top perspective views of the split-level cooling manifold of FIG. 21A illustrating the inlet duct according to one embodiment.
Figure 24B:
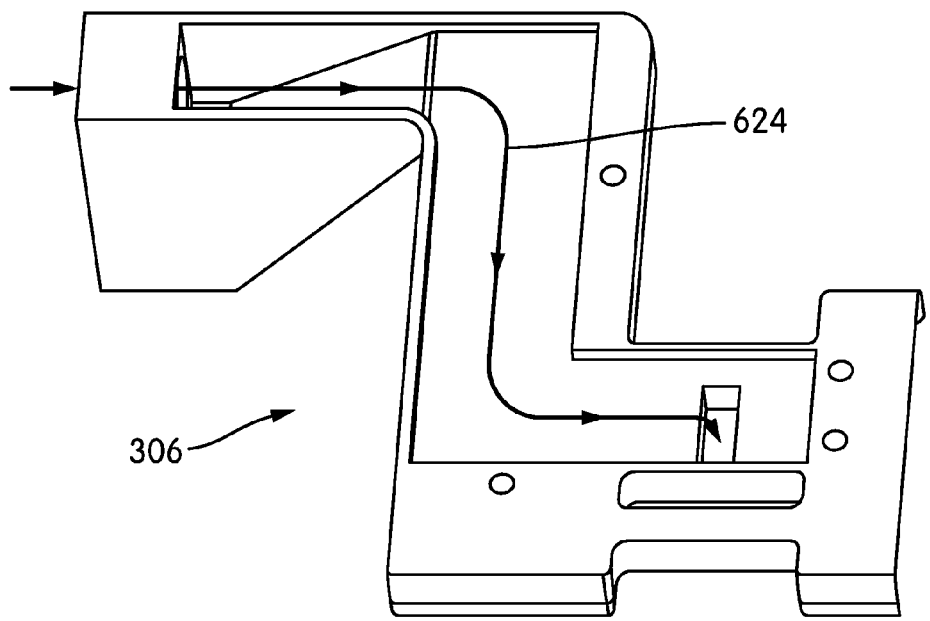
Figure 25A:
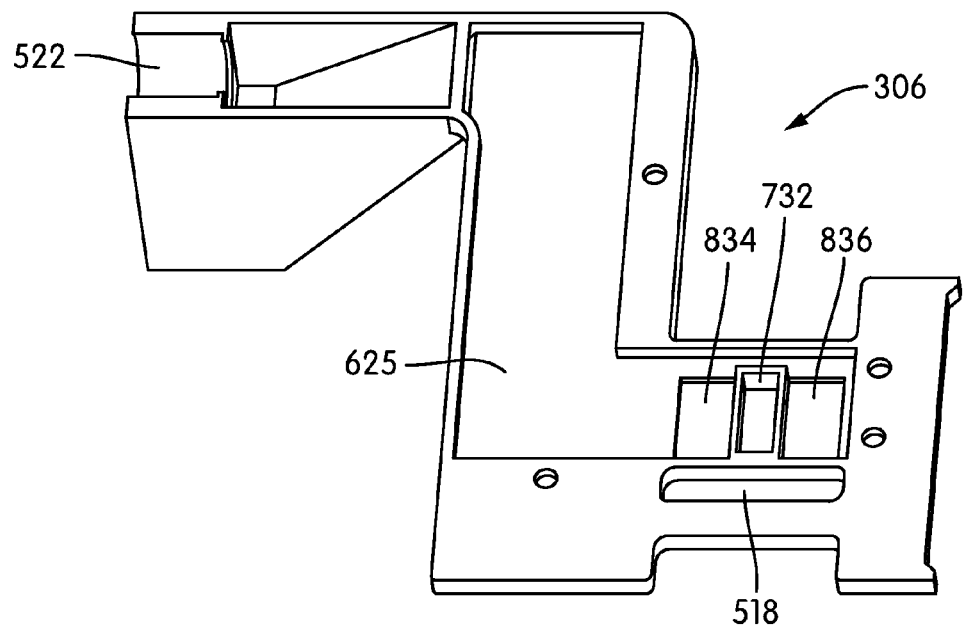
FIGS. 25A and 25B are partial to perspective views of the split-level cooling manifold of FIG. 21A illustrating the outlet duct according to one embodiment.
Figure 25B:
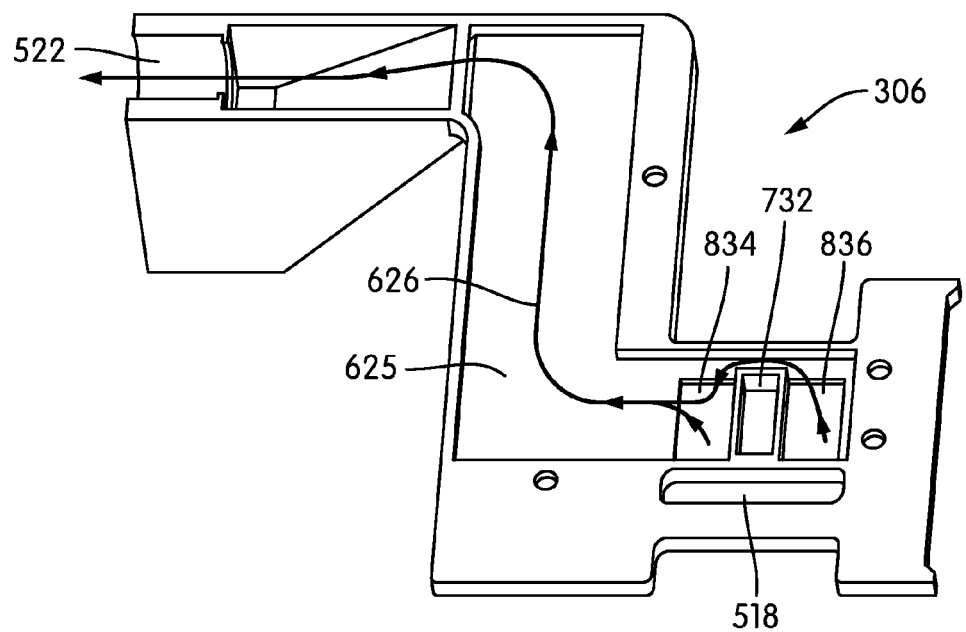
Figure 26A:
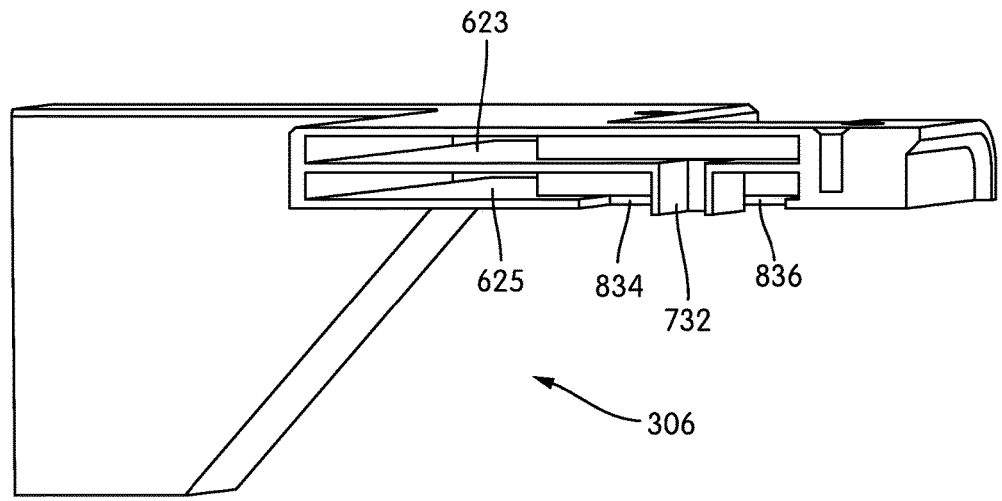
FIGS. 26A and 26B are partial side perspective views of the split-level cooling manifold of FIG. 21A illustrating the inlet and outlet ducts and confinement channels according to one embodiment.
Figure 26B:
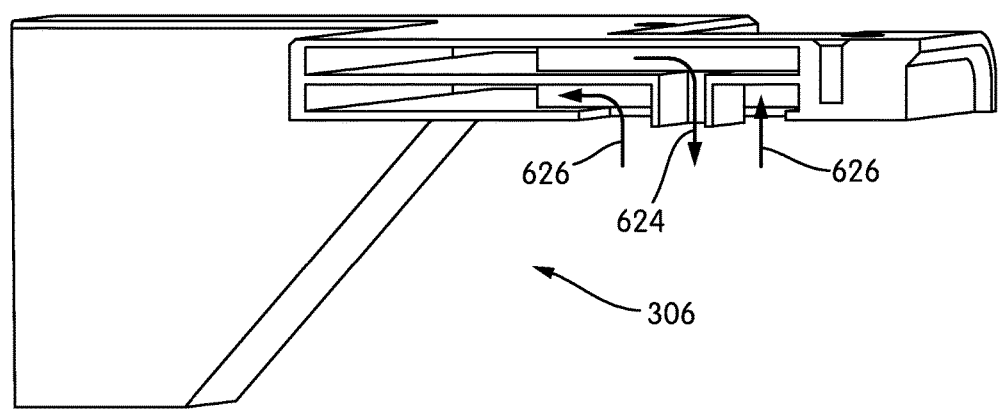

FIGS. 22, 23A, 23B, 24A, 24B, 25A, 25B, 26A and 26B illustrate the split levels of cooling manifold 306 according to one exemplary embodiment. FIG. 22 shows an inlet duct and an outlet duct of cooling manifold 306 when assembled in instrument 300 and shows the relationship of the cooling manifold 306 and microfluidic device 322. The embodiment may include a rectangular opening 325 formed in the manifold 306 or in the shelf of the frame chassis 302 above the drawer 304 which provides cooling air access to portions of the microfluidic device 322, such as the heat sinks 324 and the flexible circuit connectors 348 (see FIGS. 7 and 8). FIGS. 23A and 23B show inlet and outlet ducts of cooling manifold 306, their relationship to each other and the airflow of cooling air 624 and heated air 626 through the upper confinement channel (inlet duct) 623 and lower confinement channel (outlet duct) 625, respectively. FIGS. 24A and 24B depict a cross-section view of the split-level cooling manifold 306 to illustrate the upper, inlet duct and airflow of cooling air 624 in isolation. FIGS. 25A and 25B depict a cross-section view of the split-level cooling manifold 306 to illustrate the lower, outlet duct and airflow of the heated air 626 in isolation. FIGS. 26A and 26B depict a side cross-section view of the split-level cooling manifold 306.

In the illustrated embodiment, the top level of the cooling manifold 306 forms an inlet duct and the bottom level of the cooling manifold 306 forms an outlet duct. The inlet duct may comprise an inlet 520, upper confinement channel 623 and vertical channel 732 (See FIGS. 23A, 23B, 24A, 24B). The outlet duct may comprise openings 834 and 836, lower confinement channel 625 and outlet 522 (See FIGS. 23A, 23B, 25A, 25B). Cooling air 624 enters the inlet duct of cooling manifold 306 at inlet 520 and is directed towards vertical channel 732 through upper confinement channel 623. Cooling air 624 exits the inlet duct through vertical channel 732, which extends through the outlet duct, and is directed downwards onto the fins 326 of the one or more pin-fin heat sinks 324a, 324b of microfluidic device 322.

After being heated by the microfluidic device 322, heated air 626 enters the outlet duct of cooling manifold 306 through openings 834 and 836. Heated air 626 is then directed towards outlet 522 through lower confinement channel 625. Heated air 626 exits the outlet duct through outlet 522. As shown in FIG. 25B, heated air 626 that enters opening 836 at the front of cooling manifold 306 flows around vertical channel 732 on its path towards outlet 522.

In preferred embodiments, cooling manifold 306 does not significantly reduce the airflow rate and maintains a high heat transfer coefficient. Also, cooling manifold 306 may provide a substantially uniform airflow distribution to the device so that hot spots are not created on the device. For example, too little flow on the left side of the device 322, may cause overheating of that side of the device.

Although the upper level is used for the inlet duct and the lower level is used for the outlet duct in the illustrated embodiment, such a configuration is not required. In the alternative, the upper level may be used as an outlet duct and the lower level may be used as an inlet duct.

In some embodiments, one or more temperature measuring devices (i.e., temperature probes) may be located in the cooling manifold 306. The temperature measuring devices could be located anywhere along the manifold. In a preferred embodiment, the temperature measuring devices would be close to the heated microfluidic device so the measurement is indicative of the air temperature when it hits or flows off of the device. The temperature measuring devices may be, for example, wire like with a probe tip suspended in air. The temperature measuring device may be any suitable device known in the art for measuring temperature. The temperature measuring device may be, for example, a thermistor, thermocouple or resistance temperature detector.

In the illustrated embodiment, cooling manifold 306 may have a first temperature measuring device (not shown) located in the upper confinement channel 623. First temperature measuring device may be located close to the microfluidic device 322 by locating the first temperature measuring device near the vertical channel 732. In an alternative embodiment, the first temperature measuring device may be located in the vertical channel 732. For instance, the first temperature measuring device may be located in the vertical channel 732 where cooling air 624 exits the cooling manifold 306.

In the illustrated embodiment, cooling manifold 306 may have a second temperature measuring device (not shown) located in the lower confinement channel 625. Second temperature measuring device may be located close to the microfluidic device 322 by locating the second temperature measuring device near opening 834 and/or opening 836. For instance, the second temperature measuring device may be located in the lower confinement channel 625 where heated air 836 enters the cooling manifold 306.

Figure 21B:
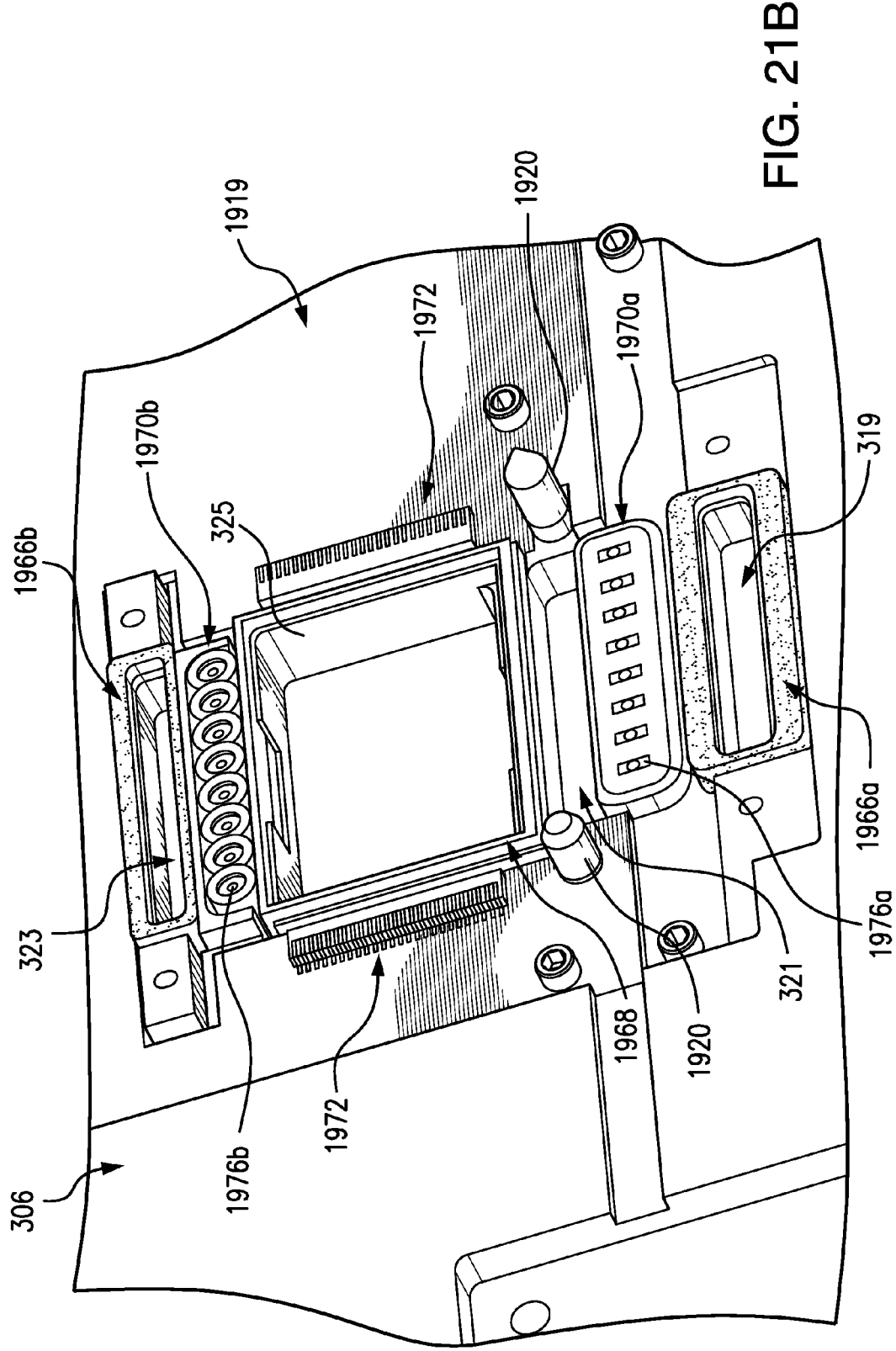
FIG. 21B is bottom, partial perspective view of the manifold, showing a gasket arrangement for providing a sealed interface between the manifold and a microfluidic device.

In some embodiments, one or more baffles are used to help keep air flowing in the confinement channels 623, 625 directed at the heat sinks 324a, 324b and away from exposed liquids in the wells of the microfluidic device 322. In one non-limiting embodiment, the baffles may comprise one or more gaskets configured to provide an air-tight seal between portions of the microfluidic device 322 and the cooling manifold 306. Such gasket(s) may be provided on the bottom of the cooling manifold 306 wherein the manifold interfaces with the microfluidic device 322. Alternatively, gaskets may be provided on the microfluidic device 322 itself and/or on portions of the shelf of the frame chassis 302 above the drawer 304 that interface with portions of the microfluidic device 322. FIG. 21B shows a bottom portion of the cooling manifold 306 that extends through, or is aligned with, one or more openings formed in the shelf of the instrument frame chassis 302 above the drawer 304. In other words, FIG. 21B is a view of the cooling manifold 306 that might be seen looking up at the cooling manifold 306 from inside drawer 304 of instrument 300.

In one embodiment, a connector printed circuit board ("PCB") 1919 is attached to the bottom of cooling manifold 306. The connector PCB 1919 may include electrical contacts 1972, which may be configured to mate with and establish an electrical connection to flexible circuit connectors 348 of a microfluidic device 322 when the microfluidic device 322 is positioned beneath the manifold 306. The cooling manifold 306 shown in FIG. 21B is configured to operatively mate with the microfluidic device 322 shown in FIG. 6A (although other manifold configurations for different microfluidic device configurations are contemplated). Access openings 319, 321, and 323 that extend through the cooling manifold 306 (or through the shelf of the frame chassis 302 above the drawer 304) allow fluid access or interface (e.g., access for robotic pipettors 308a, 308b) to portions of the microfluidic device 322. Rectangular opening 325 allows cooling air flowing within the manifold 306 to flow to portions of the microfluidic device 322, such as the heat sinks 324a, 324b, and allows heated air to flow from the microfluidic device 322 back into the manifold to flow away from the microfluidic device 322. The manifold 306 may also include pressure ports 1976*a* and pressure ports 1976*b* connected to tubes 311 (See FIG. 4).

In the non-limiting embodiment shown in FIG. 21B, the gaskets are configured to cooperate with a microfluidic device 322 including a microfluidic chip 328 that will generally be aligned with rectangular opening 325 and an interface module 330 including sample storage wells 334 and/or blanking solution storage wells 346 that will generally be aligned with access openings 319 and 323, respectively, one or more inlet ports 332 that will generally be aligned with access opening 321, and pressure connection ports or wells (e.g., vent wells 336 and waste wells 340) that will generally align with manifold pressure ports 1976*a* and 1976*b*. Access opening 319 may provide access to sample storage wells 334 of the microfluidic device 322. Access opening 321 may provide access to inlet ports 332 of the microfluidic device 322. Access opening 323 may provide access to blanking solution storage wells 346 of the microfluidic device 322.

The gaskets may include well gaskets 1966*a* and 1966*b* that partially or completely surround access openings 319 and 323, respectively, microfluidic device gasket 1968 that partially or completely surrounds rectangular opening 325, and/or pressure coupling gaskets 1970*a* and 1970*b* that surround the individual pressure ports 1976*a* and 1976*b*, respectively. Microfluidic device gasket 1968 surrounding the rectangular opening 325 seals in cooling air 624 flowing in the inlet duct 623 of the cooling manifold 306 and heated air 626 flowing in the outlet duct 625 from one or more heat sinks 324*a*, 324*b* of the microfluidic device 322. As shown in FIG. 21B, microfluidic device gasket 1968 may be a rectangular gasket. However, the microfluidic device gasket 1968 may have rounded edges, and other shapes, such as an oval, may alternatively be used.

Registration posts 1920 extend below the manifold 306 and enter registration features 338 of the interface module 330 of the microfluidic device 332.

According to one embodiment, pressure coupling gaskets 1970*a* and 1970*b* may be configured to provide substantially pressure-tight seals between pressure ports 1976*a* and 1976*b* of the manifold 306 and the vent wells 336 and waste wells 340, respectively, so that pressure (positive pressure or vacuum) can be administered to the microfluidic device 322 via pneumatic coupling between the pressure ports 1976*a* and 1976*b* of the manifold 306 and the vent wells 336 and waste wells 340, respectively. In an embodiment, well gaskets 1966*a* and 1966*b* may be configured to seal air (particularly the cooling air and heated air flowing in the manifold) out of the storage wells 334, 346 of the microfluidic device 322. More specifically, well gasket 1966*a* may be configured to seal air out of sample storage wells 334 of the microfluidic device 322, and well gasket 1966*b* may be configured to seal air out of blanking solution storage wells 346 of the microfluidic device 322. Some embodiments may include an additional well gasket surrounding access opening 321 and configured to seal air out of the inlet ports 332 of the microfluidic device 322. The additional well gasket may extend partially or completely around the inlet ports 332 of the interface module 330 of the microfluidic device 322. The well gaskets 1966*a* and 1966*b* illustrated in FIG. 21B are configured to extend completely around the storage wells 334, 346 of the microfluidic device 322. However, this is not necessary, and, in alternative embodiments, well gaskets 1966*a* and/or 1966*b* may be configured to extend only partially around the storage wells 334, 346 of the microfluidic device 322.

In some embodiments, the well gaskets 1966*a* and 1966*b* and microfluidic device gasket 1968 may, individually and/or together, seal the cooling air from exposed liquids in storage wells 334, 346 of the microfluidic device 322. Pressure coupling gaskets 1970*a* and 1970*b* provide pressure-tight seals with pressure ports 1976*a* and 1976*b*, respectively. However, in some embodiments, no baffles or gaskets are provided on the cooling manifold and/or microfluidic device. In one embodiment, the microfluidic device gasket 1968 alone may be employed to seal in cooling air from the cooling manifold and heated air from one or more heat sinks of the microfluidic device (and thereby keep the cooling and heating air from exposed liquids of the microfluidic device 322), and the well gaskets 1966*a* and 1966*b* are omitted.

In one embodiment, the drawer 104 includes angled guide tracks or other features that cause the microfluidic device 322, to raise when the drawer 304 is closed. This will cause the microfluidic device 322 to be pressed against the gasket(s), thereby enhancing the sealing effects of the gaskets. When the microfluidic device 322 is raised, registration posts 1920 engage with and enter into registration features 338 of the microfluidic device 322 to properly orient the microfluidic device 322 with respect to the manifold 306 and the access openings 319, 321, 323. The registration posts 1920 have tapered, or frusto-conical, tips to compensate for initial, partial misalignment between the registration posts 1920 and the registration features 338.

The gasket(s) may be made from any suitable gasket material, including rubber, silicone foam, or neoprene.

Figure 27:
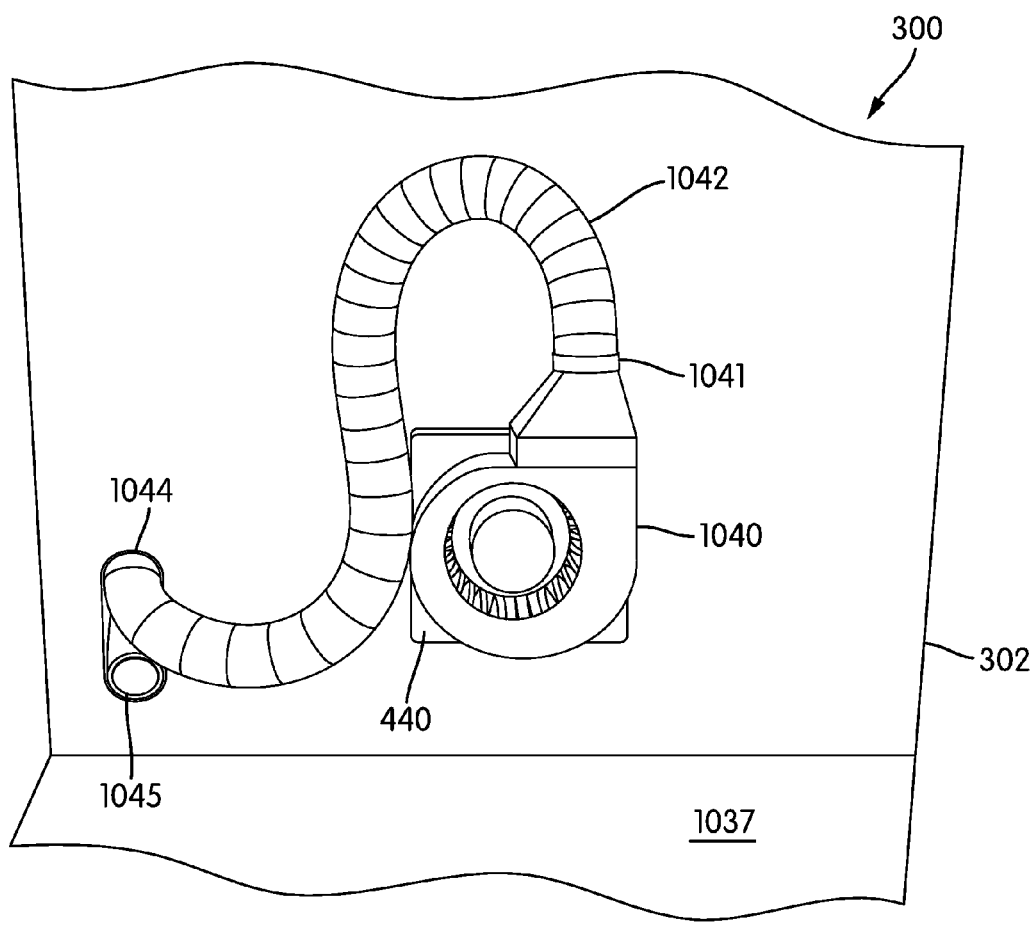
FIG. 27 is a rear view of the instrument of FIG. 4 and illustrates a blower, blower holder and duct according to one embodiment.

FIG. 27 depicts a rear enclosure 1037 of instrument 300 according to one embodiment. Rear enclosure 1037 may be enclosed and isolated from the front of instrument 300 shown in FIG. 4 by frame chassis 302. Rear enclosure 1037 may contain a blower 440. In a preferred embodiment, blower 440 is a high pressure drop blower drive capable of high flow rates despite large pressure drops. In a non-limiting example, the San Ace B97 (9BMB12P2K01) made by Sanyo Denki may be used as blower 440.

Blower 440 may be attached to a wall of instrument 300 such that cool air may be drawn into the instrument 300. By doing so, a consistent stream of cool air is ensured irrespective of heat build-up inside instrument 300. Although the blower 440 is shown as drawing air from rear enclosure 1037, blower 440 may instead draw air from outside of instrument 300.

In one embodiment, blower 440 may be supported and interfaced to a duct 1042 by a blower holder 1040. Blower holder 1040 directs the air flow from the outlet of blower 440 into a duct mounting flange 1041. Duct 1042 may be connected from blower holder 1040 to inlet 520 of cooling manifold 306 through an opening 1044 in frame chassis 302. Duct 1042 may be a flexible hose, such as corrugated tubing (e.g., Freelin Wade 1" corrugated tubing (1E-055-04)), or rigid pipes, for example, made of PVC.

In operation, airflow is ducted into instrument 300, and cooling manifold 306 directs the ducted airflow onto the microfluidic device 322. Cooling manifold 306 provides an effective cooling airflow that is isolated from exposed liquids. To isolate the airflow from exposed liquids, cooling manifold 306 directs the airflow away though a suitable outlet. Heated air may exit through an outlet within the instrument. For example, heated air 626 may simply exit outlet 522 into rear enclosure 1037 through opening 1045. In an alternative embodiment, heated air 626 may be further ducted away from the instrument.

Preheating the cooling air to a temperature that is just slightly higher than any normal ambient temperature may dramatically improved robustness. For example, in an embodiment in which PCR reactions are performed in/on the microfluidic device, preheating the cooling air to a temperature that is just slightly higher than any normal ambient temperature may result in cooling rates for the PCR reactions that are consistent regardless of ambient temperature. In another example, in an embodiment where precision temperature measurements are taken on the microfluidic device, having a repeatable cooling airflow with the same temperature regardless of ambient temperature ensures that temperature measurements on the microfluidic device remain under calibration conditions. In other words, more accurate on-chip temperature measurements are possible using cooling air at a temperature above a temperature range within which the ambient temperature is expected to remain.

A preheating system may include a heat exchanger that preheats the cooling airflow. The heat exchanger may be any suitable heat exchanger known in the art. The preheating may be done in conjunction with a temperature controller, which may be a proportional-integral-derivative ("PID) controller, which may receive feedback from one or more temperature measuring devices.

In use, the one or more temperature measuring devices detects the temperature of the cooling air after it has been preheated by heat exchanger. The temperature controller receives the measured temperature of the cooling air from the one or more temperature measuring devices and controls the heat exchanger to adjust the preheating so that the measured temperature of the cooling air from the one or more temperature measuring devices reaches a desired temperature. The desired temperature may be, for example, a temperature above a temperature range within which the ambient temperature is expected. The desired temperature may be adjustable or may be predetermined. In this way, the preheating system may be used to control the temperature of the cooling air provided to a microfluidic device.

Another aspect of the present invention relates to airflow temperature measurement and uses thereof. In one embodiment, airflow temperature measurement includes measuring the inlet (i.e., cooling) airflow temperature. The measuring of inlet airflow temperature may be carried out in conjunction with preheating or without any preheating at all. The inlet airflow temperature may be measured with a suitable temperature measuring device, such as a thermistor, thermocouple, or resistance temperature detector. The inlet airflow temperature may be measured by, for example, any of the temperature measuring devices discussed above.

By measuring the input airflow temperature, the airflow temperature may be used to enhance thermal control on the microfluidic device. For instance, a correction (i.e., adjustment) may be provided to cooling and/or heating times and/or calibration equations that are based on the temperature measured by the inlet air flow temperature measurement. These types of corrections may be implemented as automatic (i.e., instrument controlled) corrections. For instance, the corrections may be performed by a thermal controller, such as temperature controller 120c (see FIG. 1A).

In one particular embodiment, a temperature measuring device is placed within a cooling manifold where air leaves the manifold's inlet duct and is directed at a microfluidic device. The cooling manifold may be a cooling manifold as described above or any known cooling manifold. Newton's Law of cooling states that heat transfer (q) from an object is proportional to area (A) and the temperature difference between the object and the environment ($T-T_\infty$), where the proportionality constant (h) is called the heat transfer coefficient.

$$q=h*A*(T-T_\infty)$$

Because the microfluidic device can be controlled, the power q is known, and, because area A and heat transfer coefficient h are fixed, only the ambient temperature $T_\infty$ of the microfluidic device is required to determine the microfluidic device temperature T. Finally, from the perspective of the microfluidic device, the ambient temperature $T_\infty$ is the temperature of the air that hits the microfluidic device. In one embodiment, a thermal controller, such as temperature controller 120c, may determine the temperature T of the microfluidic device. However, in other embodiments, the temperature T of the microfluidic device may be determined by a different controller and/or or off the microfluidic device. In an embodiment, where the temperature T of the microfluidic device is not determined on the microfluidic device, the determined temperature T may be transmitted to the microfluidic device (e.g., to a thermal controller that is a component of the microfluidic device).

In accordance with other aspects of the invention, the instrument 300 includes a system to control the temperature inside the microfluidic device 322 to effect rapid PCR cycling and to perform high resolution melt analysis on the PCR products. According to a non-limiting embodiment, preferred systems and methods for temperature control can be configured, implemented, and/or used in association with systems, methods, and/or apparatus for determining and controlling the temperature of integrated resistive heater elements in microfluidic devices, as described in application U.S. Application Publication No. 2011-0048547, entitled "Microfluidic Systems And Methods For Thermal Control," the disclosure of which is hereby incorporated by reference in its entirety.

Figure 28:
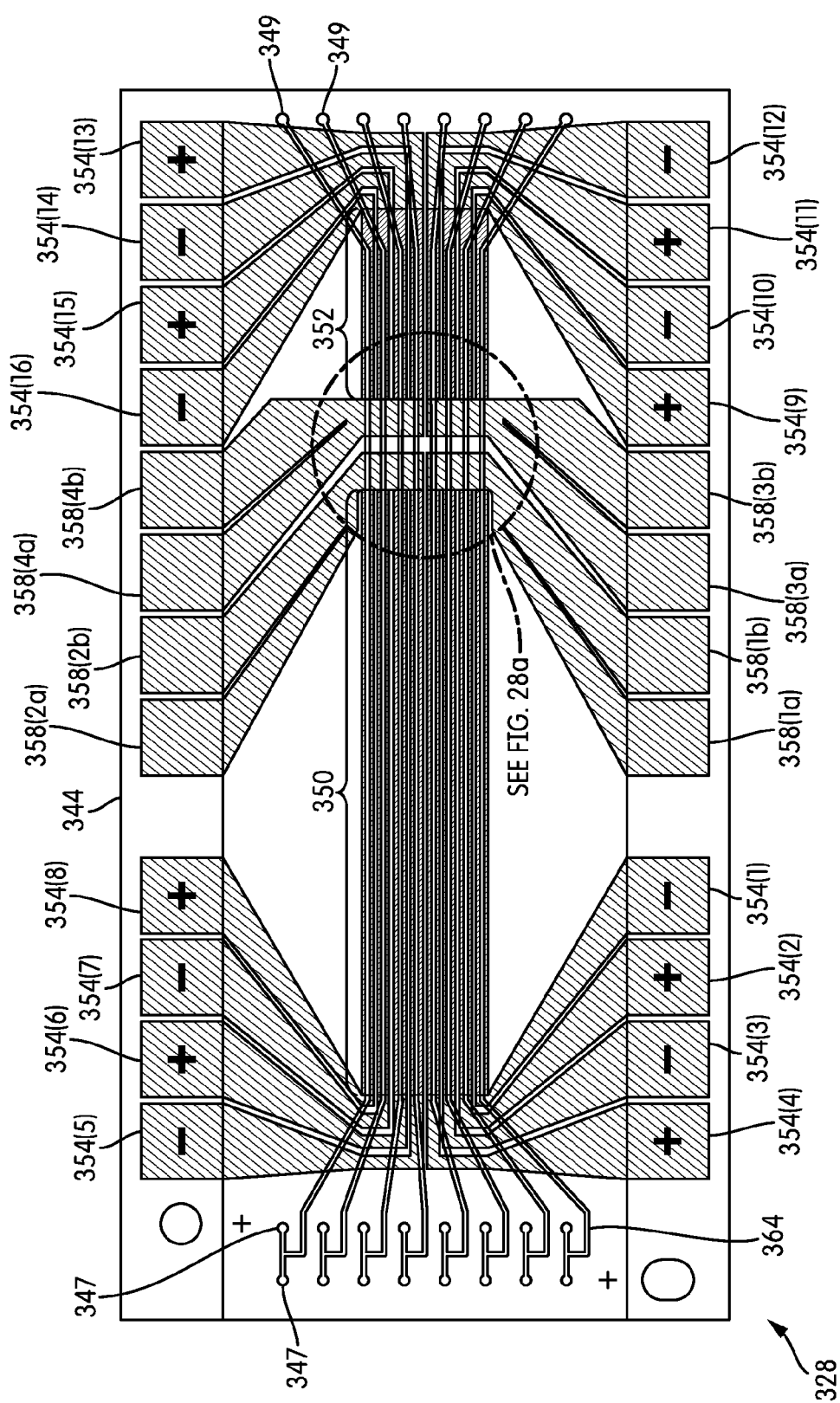
FIG. 28 is a top plan view of a microfluidic chip that may be used in association with the present invention.
Figure 28A:
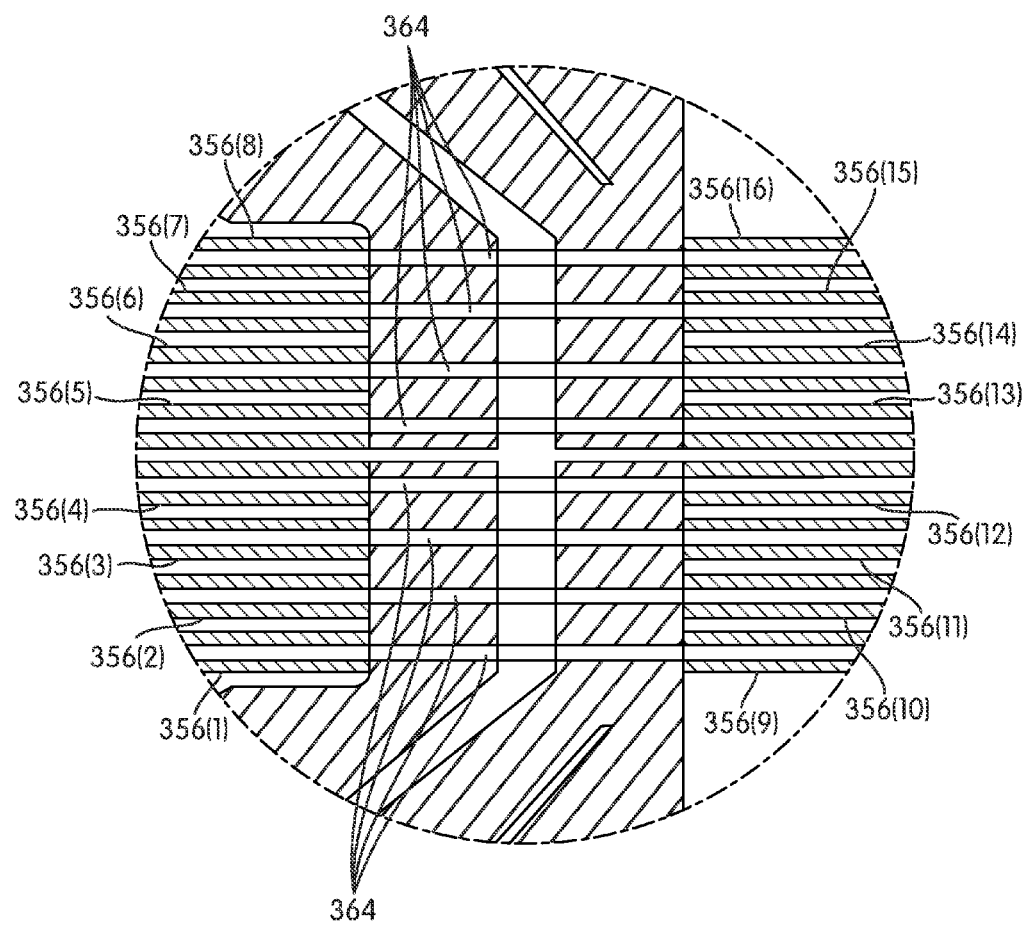
FIG. 28A is an enlargement of a portion of FIG. 28.

A more detailed illustration of the microfluidic chip 328 is shown in FIGS. 28 and 28A. The microfluidic chip 328 includes a plurality of microchannels 364 that are adjacent to thin-film resistive temperature detectors (RTDs or thermistors) 356, in accordance with one embodiment. The term RTD should be interpreted in this context in the sense that it is a heating and/or temperature measurement device constructed of any material for which resistance varies as a function of temperature. The RTD could be a thermistor, for example, and the terms RTD and thermistor may be used interchangeably herein. The RTD could be made from metals (e.g., platinum or nickel), ceramics, semi-conductors, and/or polymers. For example, in one non-limiting embodiment, microchannels 364 may be underlain with thin-film resistive temperature detectors 356. The thin-film resistive temperature detectors 356 function as precise temperature sensors as well as quick response heaters. Further, to decrease waste heat and better thermally isolate separate functional zones 350 and 352 (e.g., PCR zone and thermal melt zone), the thin-film resistive temperature detectors include lead wires or electrodes 354 and 358 which are more conductive than the thin-film resistive temperature detectors 356. The electrodes 354 and 358 may be any suitable conductive material and, in one preferred embodiment, are gold. The thin-film resistive temperature detectors 356 may be made from any suitable resistive material that demonstrates good response to temperature and is capable of being used as a heater.

Typical PCR temperatures are 95° C. for denaturation, 55° C. for annealing, and 72° C. for extension. The temperature during a step may be held for an amount of time from fractions of a second to several seconds. In principle, the DNA doubles in amount at each cycle, and it takes approximately 20 to 40 cycles to achieve a desired amount of amplification. To achieve good yield of target product, it is necessary to regulate the sample temperatures at each step to the desired temperature for each step. To reduce the process time, it is desirable to heat and cool the samples to desired temperatures very quickly and maintain those temperatures for the desired length of time to complete the synthesis of the DNA molecules in each cycle. This can be accomplished, in accordance with one embodiment, using microfluidic chip 328 with thin-film RTDs 356 as heaters.

As shown in FIGS. 28 and 28A, microfluidic chip 328 may have a plurality of microfluidic channels 364 extending across a substrate 344. The illustrated embodiment shows eight channels 364; however, fewer or more channels could be included. Each channel 364 may include one or more inlet ports 347 (the illustrated embodiment shows two inlet ports 347 in a "T" configuration per channel 364) and one or more outlet ports 349 (the illustrated embodiment shows one outlet port 349 per channel 364). Each channel may include a first portion extending through a PCR thermal zone 350 and a second portion extending through a thermal melt zone 352. As described above, a sipper (not illustrated) can be used to draw liquid into the plurality of microfluidic channels 364.

The microfluidic chip 328 further includes heater elements, which may be in the form of thin film resistive thermal detectors (RTDs) 356. In one embodiment, one or more heater element 356 are associated with each microfluidic channel 364 and are located adjacent to the microfluidic channel 364. For example, each microfluidic channel 364 may be situated above (or otherwise adjacent to) one or more heating element 356. In the illustrated embodiment, heater element 356(1)-356(8) are associated with the microfluidic channels 364 in PCR thermal zone 350 and heater elements 356(9)-356(16) are associated with the microfluidic channels located in thermal melt zone 352. For example, in the non-limiting illustrated embodiment, heater elements 356(1) and 356(9) are associated with one microfluidic channel 364 with heater element 356(1) being located in PCR thermal zone 350 and heater element 356(9) being located in thermal melt zone 352.

In one embodiment, heater electrodes 354 and 358 provide electrical power to the plurality of heating elements 356. To best utilize the limited space provided by substrate 344 of microfluidic chip 328 and reduce the number of electrical connections required, multiple RTDs share a pair of common electrodes 358. Heater electrodes 354 and 358 include individual electrodes 354 and common electrodes 358. Each pair of common electrodes includes, for example, a first common electrode 358(a) and a second common electrode 358(b). The pairs of common electrodes 358 allow the microfluidic sensors to be controlled in three-wire mode.

In the non-limiting illustrated embodiment, there are sixteen RTD heater elements 356(1)-356(16), sixteen individual electrodes 354(1)-354(16) and four common electrode pairs 358(1)-358(4). Accordingly, as illustrated in FIG. 26, there are four first common electrodes 358(1a)-358(4a) and four second common electrodes 358(1b)-358(4b). Each heater element 356 is connected to an individual electrode 354 and a pair of common electrodes 358. Multiple heater elements 356 share a pair of common electrodes 358 and are thereby multiplexed with the pair of common electrodes 358. For example, RTDs 356(1), 356(2), 356(3), 356(4), 356(5), 356(6), 356(7), and 356(8) are connected to individual electrodes 354(1), 354(2), 354(3), 354(4), 354(5), 354(6), 354(7), and 354(8), respectively. RTDs 356(1), 356(2), 356(3), and 356(4) are connected to pair of common electrodes 358(1a) and 358(1b). RTDs 356(5), 356(6), 356(7), and 356(8) are connected to pair of common electrodes 358(2a) and 358(2b). RTDs 356(9), 356(10), 356(11), 356(12), 356(13), 356(14), 356(15), and 356(16) are connected to individual electrodes 354(9), 354(10), 354(11), 354(12), 354(13), 354(14), 354(15), and 354(16), respectively. RTDs 356(9), 356(10), 356(11), and 356(12) are connected to pair of common electrodes 358(3a) and 358(3b). RTDs 356(13), 356(14), 356(15), and 356(16) are connected to pair of common electrodes 358(4a) and 358(4b).

Although the microfluidic chip 328 shown in FIG. 28 has four heater elements 356 connected to each of the four pairs of common electrodes 358, more or fewer RTDs may be multiplexed with each pair of common electrodes 358. Furthermore, more or fewer pairs of common electrodes 358 may be used to create more or fewer multiplexed sets of heater elements.

In one embodiment, each of the heater elements 356 of microfluidic device 101 is independently controlled for rapid heating and temperature sensing. As a result, the temperature of a microfluidic channel 364 in PCR thermal zone 350 may be controlled independently of the temperature of the microfluidic channel 364 in thermal melt zone 352. Also, the temperature of each microfluidic channel 364 in a zone 350 or 352 may be controlled independently of the temperature of the other microfluidic channels 364 in the zone 350 or 352.

Figure 29:
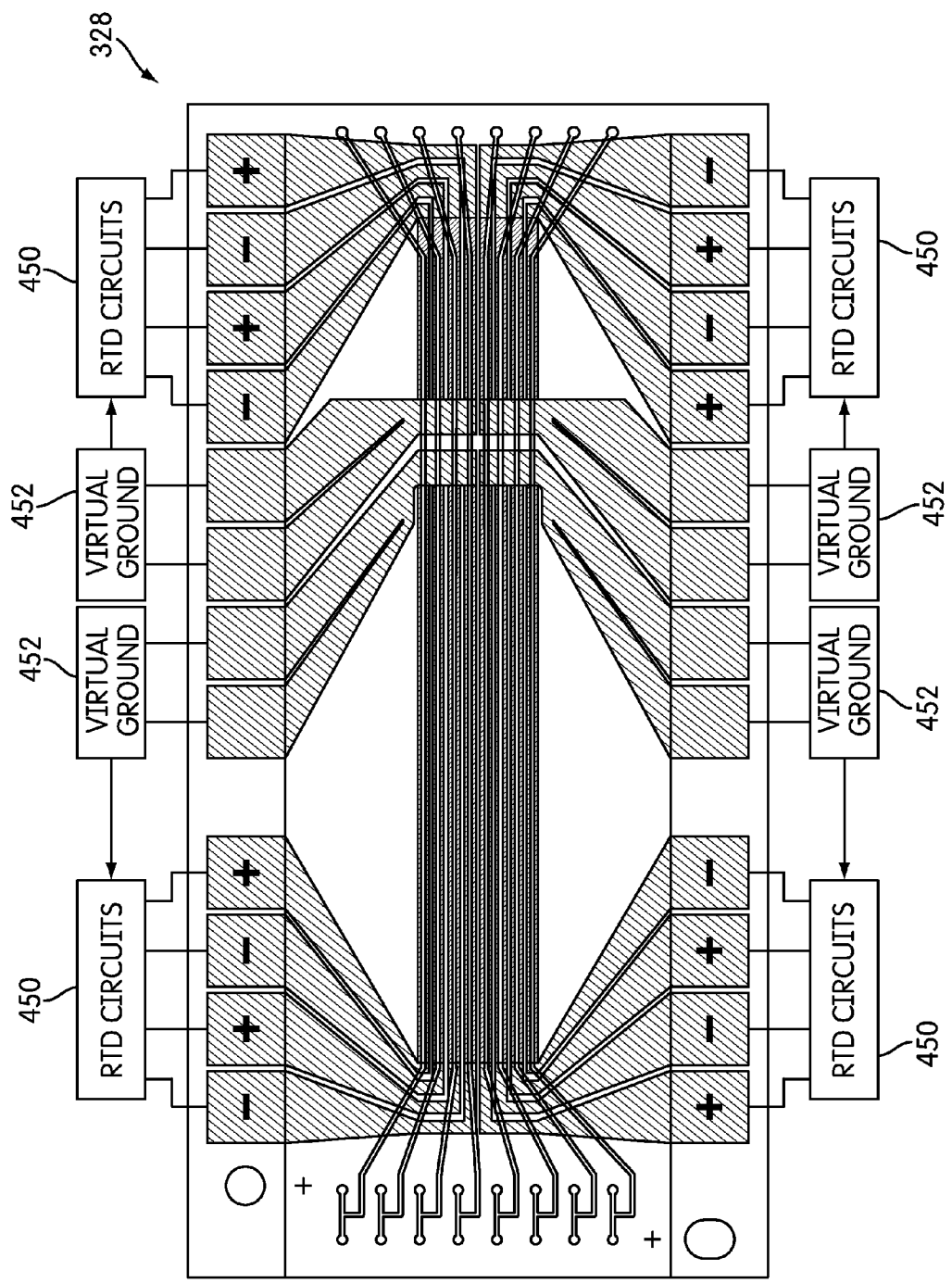
FIG. 29 is a block diagram illustrating functional units of a heater control and measurement circuit and their connections with electrodes of the microfluidic chip of FIG. 28 according to one embodiment.
Figure 30:
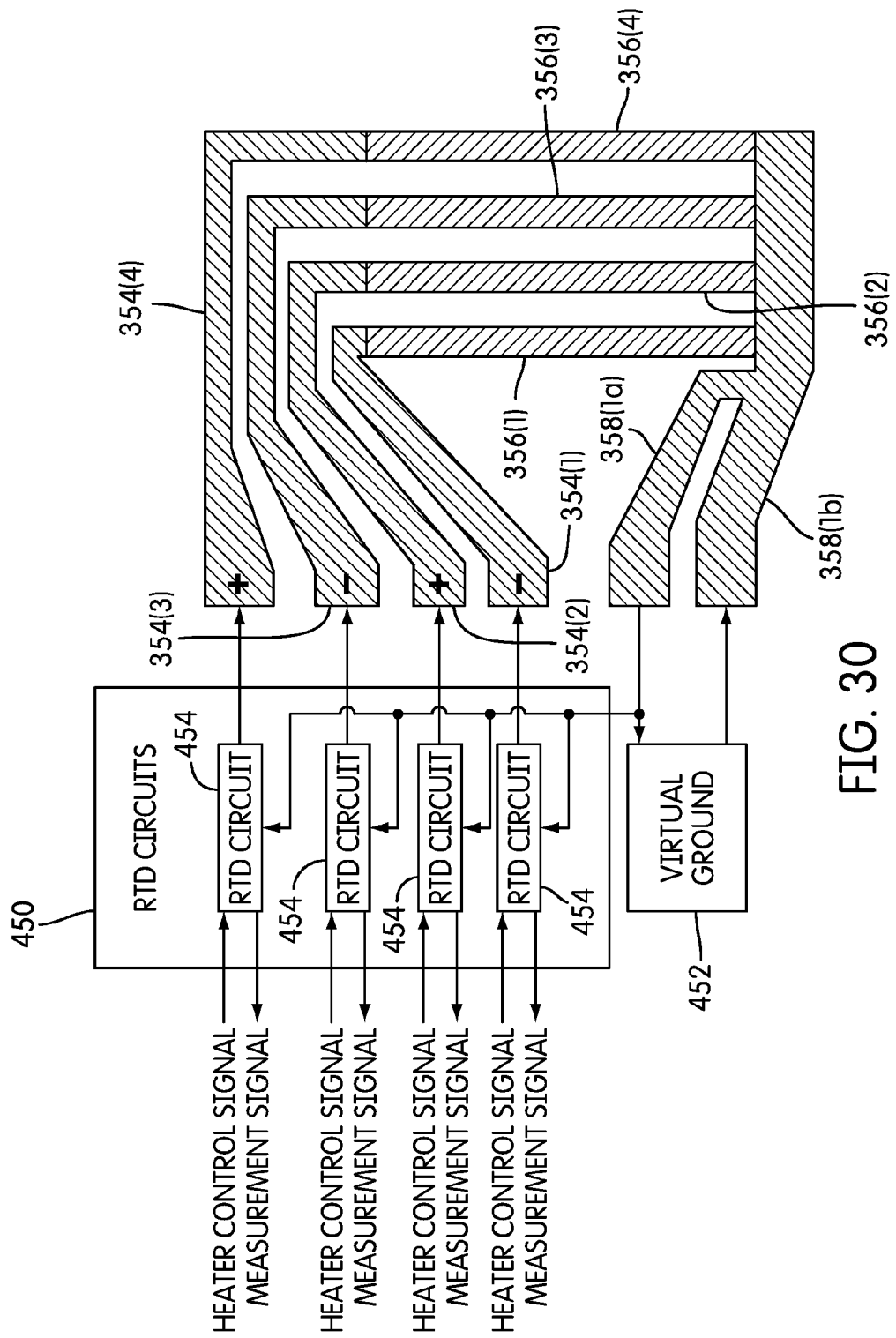
FIG. 30 is a block diagram illustrating further detail of the functional units of the heater control and measurement circuit of FIG. 29 and their connections with electrodes of the microfluidic chip of FIG. 28 according to one embodiment.
Figure 31:
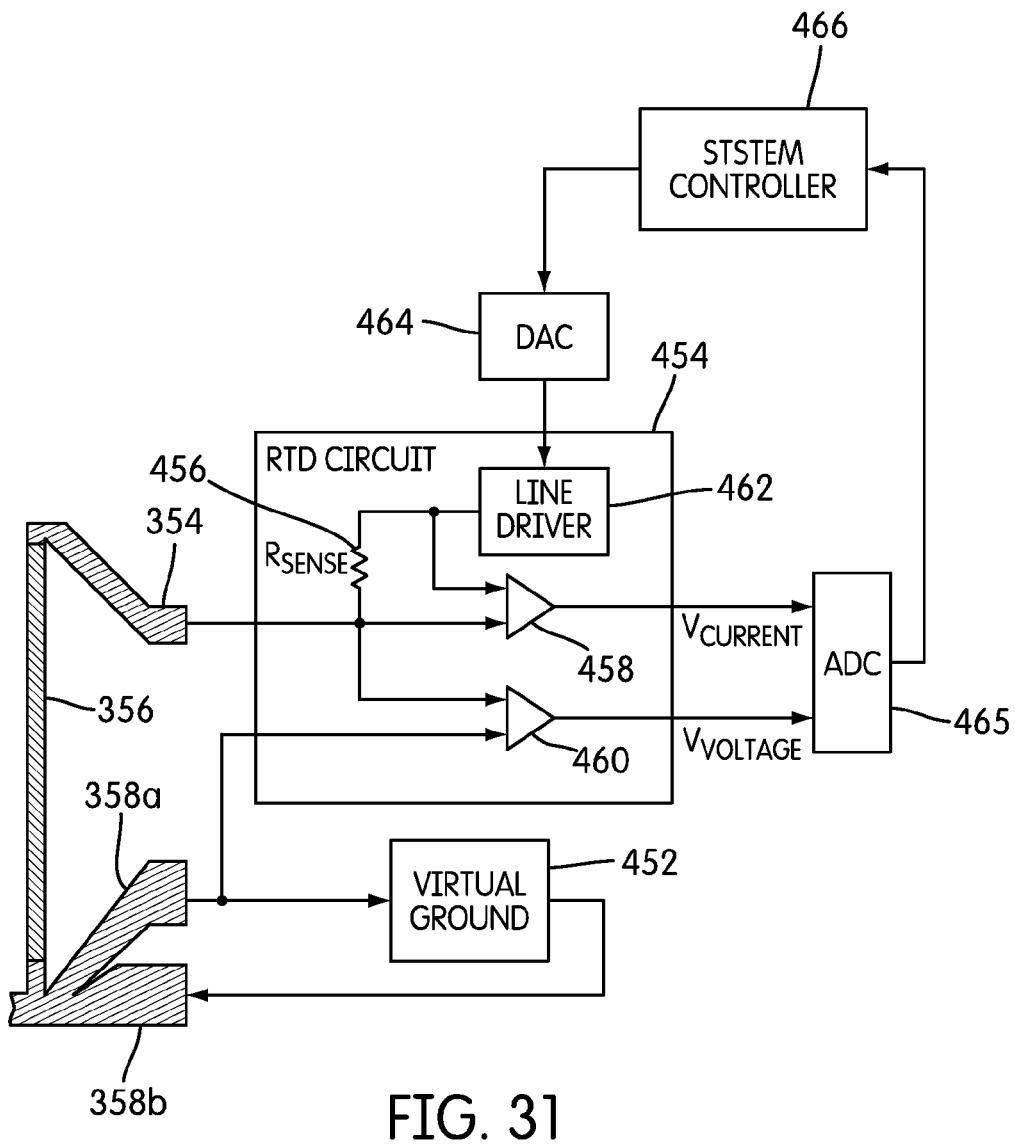
FIG. 31 is a schematic diagram illustrating a thermal control circuit for a single resistive thermal detector according to one embodiment.

FIGS. 29-31 illustrate the configuration of heater control and measurement circuit according to one embodiment. The heater control and measurement circuit may be part of temperature control system 120 of the system 100 shown in FIG. 1A. FIG. 29 shows the general configuration of heater control and measurement circuit and, generally, the manner in which heater control and measurement circuit is connected to the heater electrodes 354 of microfluidic chip 328. The heater control and measurement circuit may include groups of RTD control circuits 450 and virtual ground circuits 452, as shown in FIG. 29. Each group of RTD control circuits 450 is associated with a set of multiplexed RTDs 356. Each virtual ground circuit 452 is associated with one of pair of common electrodes 358.

FIG. 30 shows the configuration of a group of RTD control circuits 450 and shows the manner in which one group of RTD control circuits 450 and one virtual ground circuit 452 are connected to the electrodes 354, 358 of a set of multiplexed RTDs 356, in accordance with one embodiment. Specifically, the connections to individual electrodes 354(1)-354(4), first common electrode 358(1a) and second common electrode 358(1b) are shown to provide an illustrative example. Heater control and measurement circuit may be connected to the individual electrodes 354 and common electrodes 358 associated with the other sets of multiplexed RTDs 356 in a similar fashion.

As shown in FIG. 30, a group of RTD circuits 450 includes a plurality of RTD circuits 454. Each RTD circuit 454 is associated with one RTD 356 (e.g., 356(1)) and has an RTD control output connected to the individual electrode 354 (e.g., 354(1)) that is connected to the associated RTD 356. Further, each RTD circuit 454 has an input connected to the first common electrode 358 (e.g., 358(1a)) of the common electrode pair (e.g., 358(1)) connected to the associated RTD 356. The temperature of each RTD 356 is individually controlled and measured by its own RTD circuit 454.

FIG. 31 schematically illustrates the configuration of an RTD circuit 454 used for thermal control of a single thin-film RTD 356, in accordance with one embodiment. The manner in which RTD circuit 454 is connected with the individual electrode 354, first common electrode 358a and second common electrode 358b associated with an RTD 356 is also shown.

As shown in FIG. 31, each RTD circuit 454 comprises a line driver circuit 462, sense resistor 456, and differential amplifiers 458 and 460. Each RTD circuit 454 receives a heater control signal from system controller 466 through DAC 464. Line driver circuit 462 may be either a non-inverting line driver circuit or an inverting line driver circuit. Sense resistor 456 is connected in series with RTD 356, and differential amplifier 458 is configured to measure the voltage drop $V_{current}$ across the sense resistor 456. Because sense resistor 456 is connected in series with an RTD 356, the voltage drop across the sense resistor 456 is indicative of the current across the RTD 356. Differential amplifier 460 is configured to measure the voltage drop $V_{voltage}$ across RTD 356. The signals $V_{current}$ and $V_{voltage}$ respectively output from differential amplifiers 458 and 460 are transmitted to system controller 466 through ADC 465.

As stated above, each virtual ground circuit 452 is associated with a pair of common electrodes 358. As shown in FIGS. 30 and 31, according to an embodiment, a virtual ground circuit 452 has an input connected to a first common electrode 358a of the associated pair of common electrodes 358 and an output connected a second common electrode 358b of the associated pair of common electrodes 358.

Figure 32:
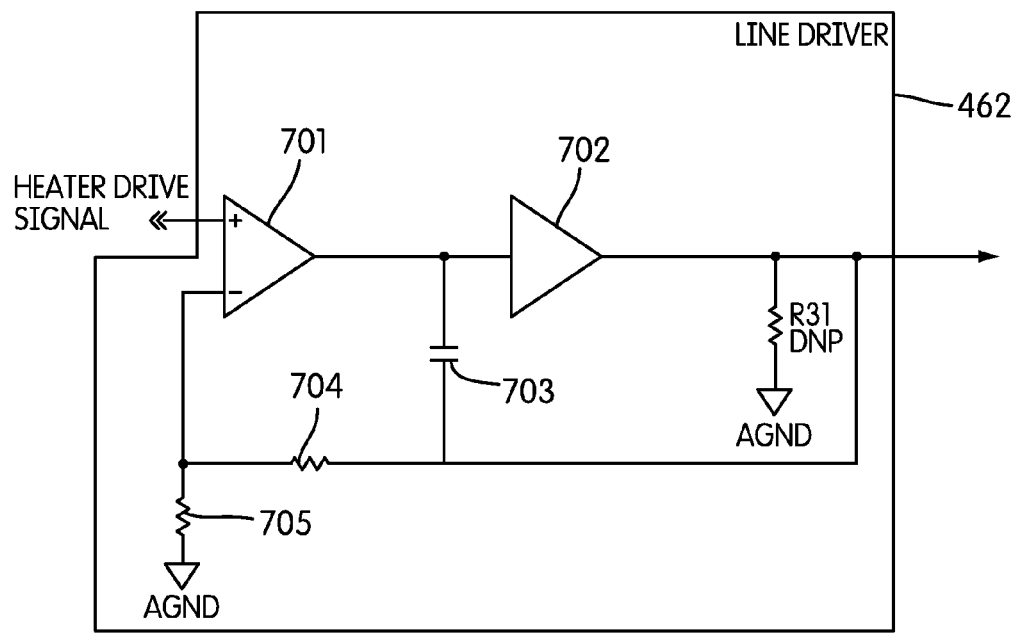
FIG. 32 is a schematic diagram illustrating a line driver circuit according to one embodiment.

FIG. 32 illustrates the configuration of a non-inverting line driver 462 according to one embodiment. Line driver circuit 462 comprises an operational amplifier 701 followed by a power buffer 702. Line driver circuit 462 additionally comprises capacitor 703 and resistors 704 and 705.

Figure 33:
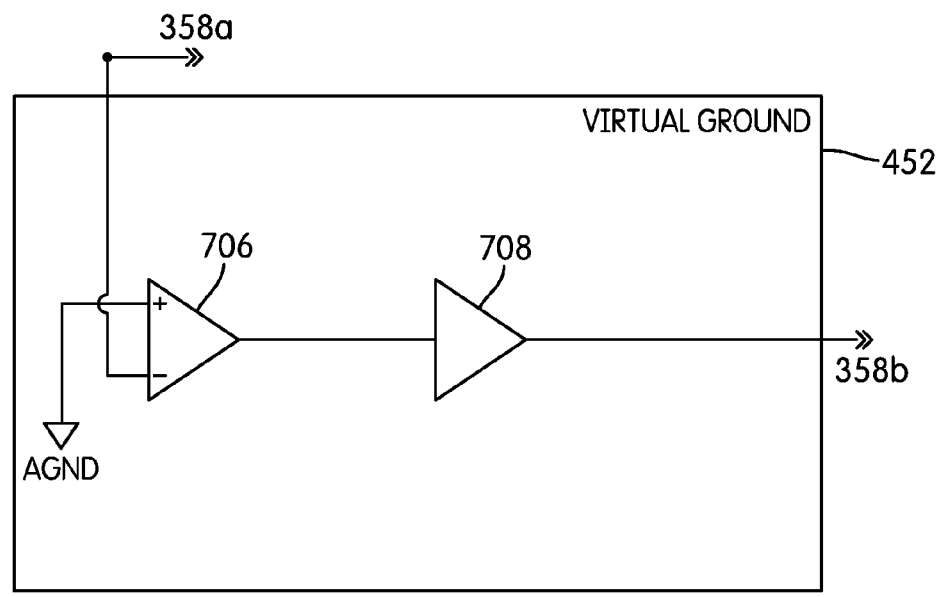
FIG. 33 is a schematic diagram illustrating a virtual ground circuit according to one embodiment.

FIG. 33 illustrates the configuration of a virtual ground circuit 452 according to one embodiment. Virtual ground circuit 452 comprises an operational amplifier 706 followed by a power buffer 708. Operational amplifier 706 has a first input connected to a first common electrode 358a and a second input connected to ground. The output of operational amplifier 706 is input into power buffer 708. The output of power buffer 708 is connected to a second common electrode 358b.

Figure 34:
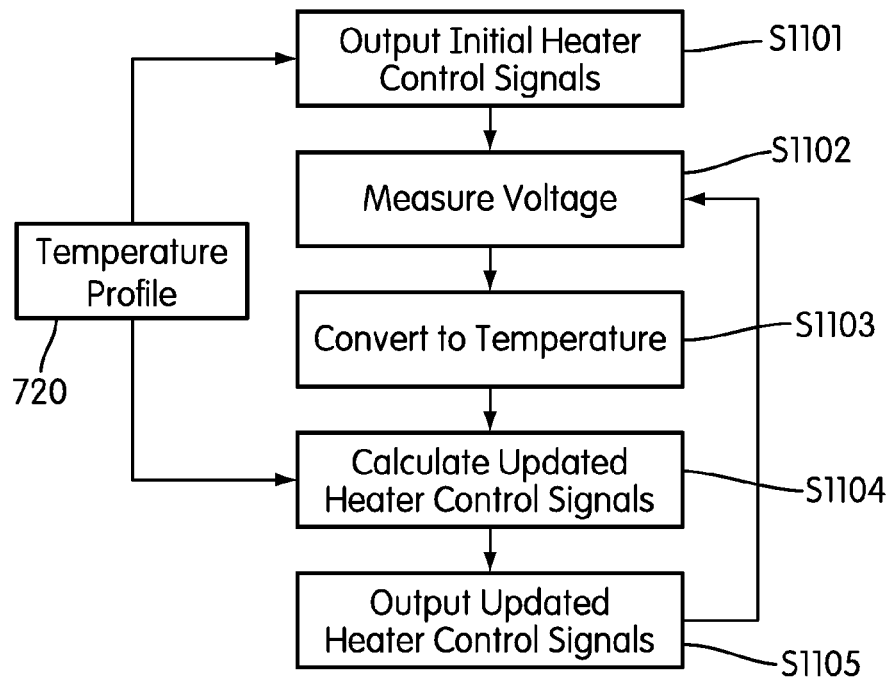
FIG. 34 is a flow chart showing a closed-loop thermal control algorithm according to one embodiment.

In operation, the thin-film RTDs 356 may be used for temperature sensing as well as rapid heating. System controller 466 may utilize both of these functions to perform high speed closed-loop thermal control of RTDs 356. A flow chart illustrating the closed-loop thermal control according to one embodiment in shown in FIG. 34. At step S1101, system controller 466 outputs initial heater control signals to the RTD circuits 454 of heater control and measurement circuit through DAC 464. System controller 466 may use temperature set points output from one or more temperature profiles 720 to generate the heater control signals. For example, system controller 466 may have a PCR profile for generating heater control signals for RTDs 356(1)-(8) located in PCR thermal zone 350 of microfluidic chip 328 and a thermal ramp profile for generating heater control signals for RTDs 356(9)-(16) located in thermal melt zone 352 of microfluidic chip 328.

The temperature of each of the RTDs 356 is sensed. Temperature sensing may be achieved by performing steps S1102 and S1103. In step S1102, the currents and voltage drops across each of the RTDs 356 are measured. The currents across each of the RTDs 356 may be measured by using the differential amplifiers 458 of the RTD circuits 454 to detect the voltage drops $V_{current}$ across the sense resistors 456 connected in series with the RTDs 356. The voltage drops $V_{voltage}$ across each of the RTDs 356 may be measured by using the differential amplifiers 460 of the RTD circuits 454 having inputs respectively connected to the individual electrode 354 and first common electrode 358 to which the RTD 356 is connected. In step S1103, the measured currents and voltage drops are converted to temperatures, which may be accomplished using a two-step process.

In the first step, the resistance of each RTD 356 is determined using the ratio of the measured currents to the measured voltages (i.e., $V_{voltage}/V_{current}$). In the second step, the determined resistances of the RTDs 356 are converted to the temperatures of the RTDs 356. The conversion of resistance to temperature may be achieved using a simple mathematic expression or lookup table. Given an RTD 356 with sufficient linearity over the temperatures of interest, one may determine the resistance with just two calibration coefficients:

(i.e., Temperature=$k0+(k1*Resistance)$).

The specific expression used to determine temperature may be altered by the system designers to give the appropriate level of accuracy for a particular application. Specifically, for example, a quadratic relationship may be appropriate for some materials and applications.

After the temperature of the RTDs 356 has been sensed, in step S1104, system controller 466 calculates updated heater control signals. The updated heater control signals may be calculated using temperature set points from one or more temperature profiles 720, such as the PCR profile and thermal ramp profile described above. In addition, the updated heater control signals may be calculated using proportional-integral-derivative (PID) control (i.e., three-term control). Under PID control, the weighted sum of proportional, integral and derivative values may be used to adjust/update the heater control signals where the proportional value determines the reaction to the current error, the integral value determines the reaction based on the sum of recent errors, and the derivative value determines the reaction based on the rate at which the error has been changing.

In step S1105, the system controller 466 outputs the updated heater control signals to the RTD circuits 454 of a heater control and measurement circuit through a DAC. The process then begins again at step S1102.

The heater driving performed by thermal control circuit of the microfluidic system will now be described. Heating of each thin-film heater/sensor RTD 356 may be digitally controlled and, in a preferred embodiment, is amplitude modulated. Amplitude modulation is preferred because a continuous modest change in voltage, rather than large voltage steps, avoids slew rate limits and improves settling time. However, since the heater control is digital, various heating schemes are possible and easily implemented. For example, pulse width modulation (PWM) and alternating current (AC) concepts may also be used.

In some embodiments, system controller 466 outputs a heater control signal to heat heater elements 356 that instructs a DAC to output a suitable voltage, whose magnitude is determined by the thermal load. Suitable DACs include multifunction data acquisition (DAQ) devices such as the PXI-6289 from National Instruments, as well as numerous other analog output cards available. Some of the desired characteristics of the DAC include the resolution, absolute accuracy, linearity, response time, and current output capabilities. Specifically, the DAC should have sufficient bit resolution to ensure the desired precision of heating. With too low a resolution for the heater drive signal, the RTD 356 will oscillate around the desired set point. A multifunction DAQ device should address these characteristics as well as have sufficient number of output channels to provide independent control of the multiplexed RTDs 356. Alternatively, system controller could be configured to output digital signals through a digital output device which are interpreted by an integrated circuit that features many DACs, such as, for example, the LTC2600 Octal 16-bit rail-to-rail DACs from Linear Technology.

Many otherwise suitable DACs lack sufficient current sourcing capabilities for the desired heating. One specific application where this is of concern is in PCR. The throughput of a PCR chip can be dramatically increased if PCR cycle times are reduced. Having excess heating capability (large current sourcing) can reduce the denature and extension transition times. Furthermore, it allows the system to overcome highly efficient cooling means which are desired for fast annealing but would reduce the heating rate. To improve the current sourcing capabilities, in accordance with one embodiment, a power buffer circuit (i.e., line driver circuit) 462 pre-conditions the DAC signal before it is used by an RTD circuit 454. One such line driver 462 is the combination power buffer 702 with operational amplifier 701 circuit shown in FIG. 32. Operational amplifier 701 may be, for example, Linear Technology Operational Amplifier LT1012. Power buffer 702 may be, for example, Linear Technology Power Buffer LT1010. The desired characteristics of this circuit 462 are the response time, current output capacity, noise, linearity, operating voltage, and absolute accuracy. In a preferred embodiment, power buffer 702 is capable of providing up to 150 mA of current.

It may also be desirable to amplify or attenuate the DAC's signal with the above described line driver circuit 462. For example, with fast PCR it may be desirable to drive the thin-film RTDs 356 with up to 20 V for fast heating. A typical DAC may have insufficient range to achieve this voltage (such as is the case with the PXI-6289 which can output up to ±10V). In some embodiments (preferred for PCR), the line driver circuit 462 could be configured to provide 2 times gain to the original DAC output. This amplification could be realized with inverting or non-inverting feedback (see FIG. 32) since the DAC is capable of bi-polar output.

Further, in accordance with one preferred embodiment, the thermal control circuit is configured for bi-polar driving potential. This can be achieved through digital control of bi-polar DACs, or alternatively, the output of uni-polar DACs could be inverted with the circuitry of line driver circuit 462. The bi-polar driving potential or alternating polarity of the heater driving signals functions in concert with the virtual grounding circuits 452, which are described in further detail below.

In FIGS. 28, 29, and 30, the individual electrodes 354 have been labeled with pluses (+) and minuses (−) to illustrate the alternating polarity of the heater drive signals with which the RTDs 356 may be driven, in accordance with one embodiment. Individual electrodes 354 driven with heater driving signals having a positive polarity are not structurally different from individual electrodes 354 driven with heater driving signals having a negative polarity. The pluses (+) and minuses (−) with which the individual electrodes 354 have been labeled merely provide an illustrative example of the bi-polar driving of RTDs 356. Further, the specific manner with which RTDs 356 have been labeled in FIGS. 28, 29, and 30 is not limiting. For example, RTDs 356(1)-356(8) and/or RTDs 356(9)-356(16) could be driven with polarities opposite to the polarities shown in FIG. 28. Alternating the polarities of the heater drive signals in combination with the virtual grounding of the common electrodes 358 reduces the current density in and temperature of the common electrodes 358 compared to uni-polar driving in which all RTDs are driven with heater driving signals have the same polarity.

The virtual ground circuit 452 shown in FIG. 33, in accordance with one embodiment, works in conjunction with the alternating polarity of the heater driving signals to reduce the current in the pairs of common electrodes 358. Minimizing the current in the pairs of common electrodes 358 decreases waste heat, which is advantageous from a system level and improves the thermal isolation of microfluidic functional zones 350 and 352 in which, for example, PCR and high resolution thermal melt are performed. Furthermore, decreasing the unwanted heating of the common electrodes 358 improves the specificity of the temperature measurement because, for example, at least one of the common electrodes 358 must be used for temperature measurement.

In accordance with embodiments, the function of the virtual ground circuit 452 is to utilize a pair of common electrodes 358 to drive those common electrodes to near zero potential. Further, in some embodiments, nearly all of the current in the pair of common electrodes 358 is contained in one of the common electrodes 358 (e.g., second common electrode 358*b*), leaving the other common electrode 358 (e.g., first common electrode 358*a*) available for temperature sensing as will be described in further detail below.

In one embodiment, a virtual grounding circuit 452 is implemented for each pair of common electrodes 358 (i.e., one virtual ground circuit 452 for each multiplexed set of RTDs 356). As described above, the number of RTDs sharing a pair of common electrodes 358 may be chosen for the specific application. However, in some embodiments, it is desirable to consider the current imbalance that may result. If all of the multiplexed RTDs 356 were driven with the same polarity potential, then a large current would flow through one of the common leads 358 (e.g., second common electrode 358*b*). In contrast, with bi-polar driving signals, any current imbalance will be much smaller. Specifically, positive driving signals tend to cancel out negative ones. A small current imbalance may still exist due to imperfections in the thin-film RTDs 356, differences in RID layout, or non-uniformity of cooling. In some embodiments, the preferred condition would be a symmetric layout in which polarities alternated for each RTD (e.g., positive/negative/positive/negative). If true symmetry were achieved, there would be no current imbalance and nearly no current in the common electrodes 358.

Further, in some embodiments, the virtual grounding circuit 452 may be capable of sourcing/sinking a resulting current imbalance. In an embodiment, operational amplifier 706 may be, for example, Linear Technology Operational Amplifier LT1012, and power buffer 708 may be, for example, Linear Technology Power Buffer LT1010. In one preferred embodiment, the power buffer 708 is capable of providing up to 150 mA of current.

The following non-limiting example describes how a small current imbalance may result in a pair of common electrodes 358 in a microfluidic system and how this current imbalance may be offset. In the example, heater driving signals having an alternating polarity were used to drive RTDs 356(1)-356(8) of the microfluidic chip 328 shown in FIGS. 28 and 28A. Positive drive voltages were used with odd RTDs 356 (e.g., 356(1), 356(3), 356(5) and 356(7)) and negative voltages were used with even RTDs 356 (e.g., 356(2), 356(4), 356(6) and 356(8)). RTDs 356(1)-356(8) were each heated to 70° C. Due to the symmetric nature of the device, the absolute currents required to heat each RTD 356 to 70° C. exhibited a symmetric profile. Because outside RTDs 356(1) and 356(8) heat the boundaries, outside RTDs 356(1) and 356(8) may require significantly more power than RTDs 356(2)-356(7). As RTDs 356(1)-356(4) share a pair of common electrodes 358(1a) and 358(1b), a small current imbalance is preferably sourced/sinked by the virtual ground circuit 452 associated with common electrodes 358 (1a) and 358(1b). In this case, the virtual ground circuit 452 associated with common electrodes 358(1a) and 358(1b) supplies about −20 mA. Similarly, as RTDs 356(5)-356(8) share a pair of common electrodes 358(2a) and 358(2b), a small current imbalance is preferably sourced/sinked by the virtual ground circuit 452 associated with common electrodes 358(2a) and 358(2b). In this case, the virtual ground circuit 452 associated with common electrodes 358(2a) and 358(2b) supplies about +20 mA.

To sense the temperature of the RTDs 356, each RTD 356 is measured individually by measuring the current and voltage drop across the RTD 356. The current is measured using a precise sense resistor 456 that is placed in series with the RTD 356, as is shown in FIG. 31. An example of a suitable sense resistor 456 is the LVS3 0.5 ohm 15 ppm wire wound surface mount resistor from Precision Resistor Co., Inc. Alternatively, and preferably, the sense resistor 456 may be a film resistor such as Y16070R50000F9W from Vishay Precision Group. Desired characteristics of the current sense resistor 456 are high precision and low temperature coefficient of resistance. In preferred embodiments, care should be taken in the layout of the heater control and measurement circuit to ensure that the sense resistor 456 is in a consistent thermal environment and free from electro-magnetic interference. Furthermore, the resistance of the sense resistor 456 should be large enough to provide a suitable signal but not too large as to decrease the ability of the circuit to rapidly heat the RTDs 356. As such, it is preferable to condition the current sense signal.

To improve the signal to noise ratio (SNR), the differential amplifier 458 that determines the voltage drop $V_{current}$ across the current sense resistor 456 may be an instrumentation amplifier, such as, for example, the LT1167 from Linear Technologies. Characteristics of a preferred embodiment of the differential amplifier 458 include its accuracy, response time, and operating voltage limits. The differential amplifier 458 may include gain to improve SNR. Specifically, the gain should be sufficient to utilize the entire range of the ADCs 106, which is typically a range such as −10 to 10 Volts. It may be preferable for the gain of the differential amplifier 458 to be programmable by using a digital potentiometer or DAC for the gain resistor. The system controller 466 could then program the variable gain resistor to improve the SNR. Some applications of this include a system and sensor controller 466 that can operate different types of microfluidic chips 328 that feature different resistances or are used at different temperatures or in different thermal environments. Alternatively, the ADC 465 could be chosen to include variable range such as with the PXI-6289 multi-function DAQ, which can operate at ranges as small as plus/minus 1 V and as high as plus/minus 10 V. In this configuration, the range of the ADC 465 would be set as required by the application.

A measure of the voltage drop $V_{voltage}$ across the RTD 356 is also required to determine the RTD resistance. The differential amplifier 460 that determines the voltage drop $V_{voltage}$ across the RTD 356 may be an instrumentation amplifier, such as the LT1167 from Linear Technologies. Because the common electrode 358 that is connected to the input of the virtual ground circuit 452 passes little to no current, it is preferable to measure the RTD voltage drop $V_{voltage}$ as referenced to this common electrode 358. As shown in FIGS. 30 and 31, the first common electrode 358a is the common electrode 358 connected to the input of the virtual ground circuit 452.

In one embodiment, the system controller 466 is configured to have a minimum voltage limit for the heater/sensor driving signal. Specifically, it is desirable for the output of DAC 464 to be maintained at least a minimum DAC output. If the DAC output were allowed to go to zero (or below some pre-determined threshold), in some embodiments, there would be no voltage or current to sense and the system controller 466 would be "blind" to the true temperature of the RTDs 356. Care should be taken to ensure that the minimum voltage limit is not too high, as this could prevent the RTD from cooling rapidly. Furthermore, if the minimum voltage limit is sufficiently high, the RTDs 356 may not cool to a low desired temperature. In some embodiments, a minimum voltage limit of 400 mV may be appropriate, but the limit may vary based on circuit components, desired accuracy, and thermal profile required.

Figure 35:
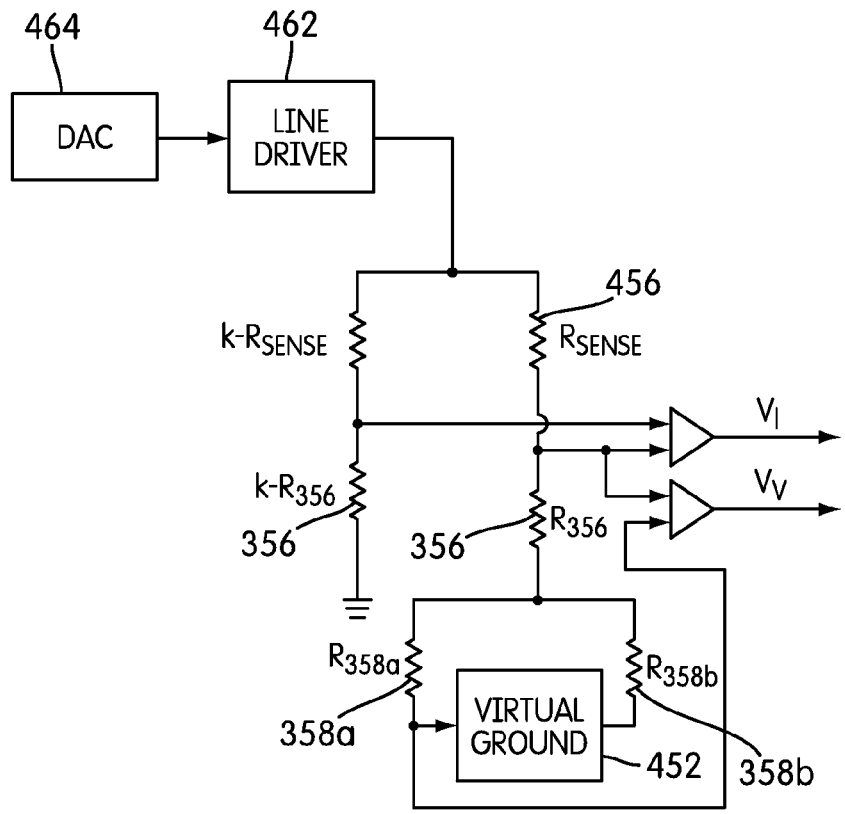
FIG. 35 is a schematic diagram illustrating a bridge configuration according to one embodiment.

In another aspect, the alternating polarity concept could be used to minimize waste heat and deliver high quality temperature measurements without using the RTDs 356 as heating elements. This configuration may be desirable if one has a need to determine the temperature on the microfluidic chip 328 but has some other means of heating (e.g., when the device is heated by an external means). Using the RTDs 356 as sensors only is easily realized using the techniques described above. In this configuration, a fixed driving potential may be used with no amplitude modulation. This configuration could, optionally, include the bridge configuration shown schematically in FIG. 35.

Figure 36:
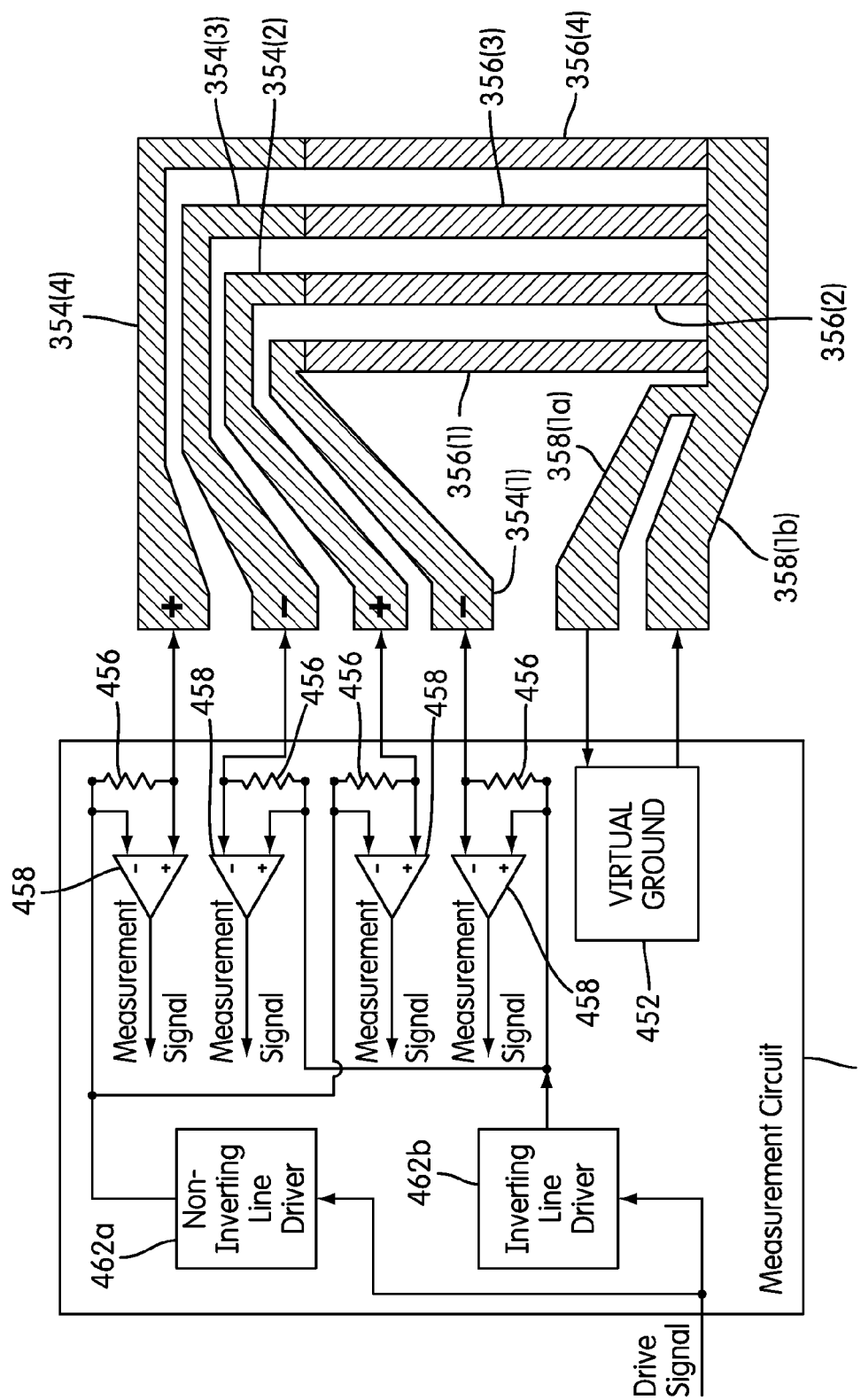
FIG. 36 is a block diagram illustrating alternating polarity temperature measurement of four sensors using a single driving signal in accordance with one embodiment.

FIG. 36 illustrates one embodiment of a configuration capable of using RTDs 356 for temperature measurement only. The temperature measurement circuit 468 shown in FIG. 36 may receive a single drive signal used for driving all of the RTDs 356. The alternating polarity may be achieved by running the drive signal for the odd RTDs 356 (e.g., RTDs 356(1), 356(3) etc.) through an inverting line driver 462b while running the drive signal for the even RTDs 356 (e.g., RTDs 356(2), 356(4) etc.) through a non-inverting line driver 462a. Measurement circuit 468 may use a bridge configuration to form reference voltage dividers. The fixed driving potential of the driving signal is preferably small to minimize self-heating and could be generated by a multi-function DAQ device such as, for example, PXI-6289, a voltage reference IC such as, for example, MAXIM's MAX6138, or a zener diode. Moreover, only one measurement per channel is required to determine temperature in this system because the driving potential is fixed.

Furthermore, systems and methods for temperature control that may be used in connection with the systems and methods of the present invention can be configured, implemented, and/or used in association with systems, methods, and/or apparatus for using a compound calibrator to calculate a relationship between temperature and an electrical characteristic of the thermal sensor, such as, for example, resistance, as described in U.S. Provisional Patent Application No. 61/378,591, entitled "Compound Calibrator For Thermal Sensors," and U.S. application Ser. No. 13/223,270 claiming priority therefrom, the disclosures of which are hereby incorporated by reference. Using a single compound calibrator, thermal control elements can be calibrated in situ. In some embodiments, a compound calibrator is used to calibrate thermal control elements on a microfluidic device. The compound calibrator can be a droplet, plug, slug, or continuous flow of any appropriate solution that, when heated, yields a thermal response profile with a plurality of features (e.g., maxima, minima, inflection points, linear regions, etc.).

Other details of a temperature measurement and control systems that may be used in connection with the systems and methods of the present invention are described in U.S. Patent Application Publication No. 2009-0248349, entitled "Microfluidic Devices with Integrated Resistive Heater Electrodes Including Systems and Methods for Controlling and Measuring the Temperature of Such Heater Electrodes" and U.S. Patent Application Publication No. 2009-0061489, entitled "Microfluidic Devices With Integrated Resistive Heater Electrodes Including Systems And Methods For Controlling And Measuring The Temperatures Of Such Heater Electrodes," the disclosures of which are hereby incorporated by reference. The publications describe a method for determining the temperature of each of a plurality of multiplexed heater electrodes, wherein the heater electrodes are part of a multiplex circuit sharing a common lead connecting the electrodes to a power supply. In one embodiment, the method includes: (a) independently measuring a voltage drop of each heater electrode in series with the common lead and storing a common power voltage drop data for each of the heater electrodes; (b) disconnecting the power supply from the common lead; (c) connecting the power supply to each of one or more of the heater electrodes, wherein the power supply is connected to one of the heater electrodes at a time; (d) while the power supply is connected to a heater electrode, isolating at least one other heater electrode from all other heater electrodes of the multiplex circuit except the heater electrode connected to power supply, measuring an isolated voltage drop at each isolated heater electrode, and storing isolated voltage drop data for each isolated heater electrode; (e) computing the resistance of each of the plurality of multiplexed heater electrodes by solving for the resistance of each heater electrode based at least in part on the stored common power voltage drop data and the stored isolated voltage drop data; and (f) deriving the temperature of each of the plurality of multiplexed heater electrodes from the computed resistance of each electrode. The publications also describe a method for calibrating a pulse width modulation thin-film heater control system for an integrated thin-film device. The publications also describe a microfluidic device for performing a biological reaction. The device includes a microfluidic chip having a plurality of microfluidic channels and a plurality of multiplexed heater electrodes. The heater electrodes are part of a multiplex circuit including a common lead connecting the heater electrodes to a power supply, and each of the heater electrodes is associated with one of the microfluidic channels. The microfluidic device also includes a control system configured to regulate power applied to each heater electrode by varying a duty cycle, and the control system is further configured to determine the temperature of each heater electrode by determining the resistance of each heater electrode.

Other details of a temperature measurement and control systems that may be used in connection with the systems and methods of the present invention are described in U.S. Patent Application Publication No. 2011-0077897, entitled "Microfluidic Devices with Integrated Resistive Heater Electrodes Including Systems and Methods for Controlling and Measuring the Temperature of Such Heater Electrodes" and U.S. Patent Application Publication No. 2011-0056926, entitled "Microfluidic Devices with Integrated Resistive Heater Electrodes Including Systems and Methods for Controlling and Measuring the Temperature of Such Heater Electrodes," the disclosures of which are hereby incorporated by reference. The publications describe a method for determining the resistance of a sensor in a multiplexed sensor network that includes a plurality of sensors sharing a common lead for connecting each of the plurality of sensors to a power supply. The combined series resistances for N number of distinct sensor pairs are sequentially measured. Each of the plurality of sensors is included in at least one of the measured sensor pairs, and "N" is the number of sensors in the plurality of sensors. Then the individual resistance of at least one of the sensors is determined based upon the measured combined series resistances.

In accordance with other aspects of the present invention, systems for data storage, processing and output are provided. In one embodiment, the systems and methods described above can be integrated into pre-existing custom data systems. These systems enable users to store, process and output data using a variety of known data processing methods, such as email.

Figure 37:
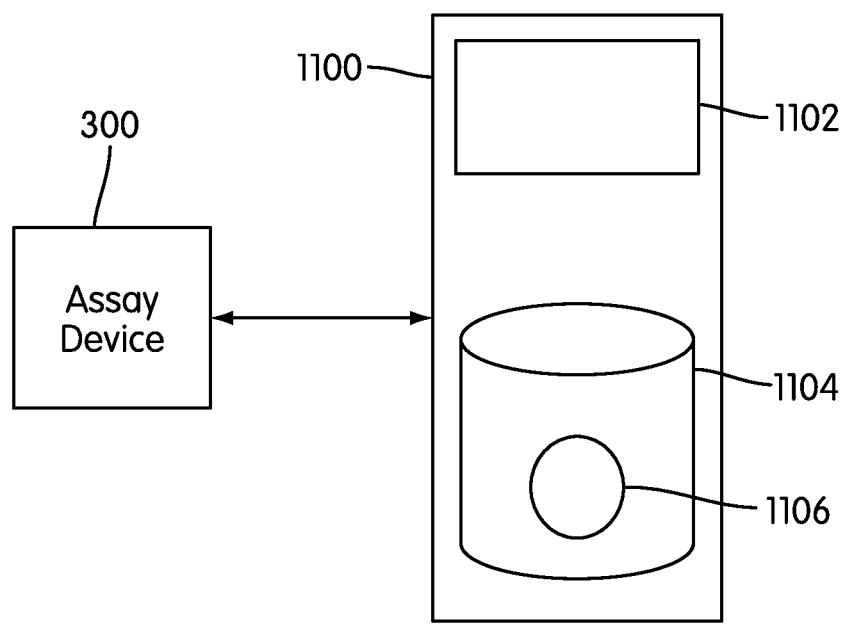
FIG. 37 is a schematic diagram of a system for storing, processing and outputting data according to one embodiment.

In one exemplary embodiment, FIG. 37 shows a computer 1100 in electronic communication, via an electronic network 1108 (e.g., a IAN) or other electronic communication pathway, with the instrument 300, such as a real-time PCR/thermal melt system described in detail above. A suitable computer 1100, as illustrated in FIG. 37, includes one or more data processing system 1102 (e.g., one or more microprocessors, one or more integrated circuits, such as an application specific integrated circuit (ASIC), Field-programmable gate arrays (FPGAs), etc. and any combination of these), a data storage system 1104 (e.g., one or more non-volatile storage devices) and computer software 1106 stored on the storage system 1104. The software 1106 is configured such that when the data processing system(s) 1102 executes the software 1106, the computer 1100 stores, processes and outputs data according to known computer programming techniques. In other embodiments, data processing system(s) 1102 is configured to perform steps described above without the need for software 1106. That is, for example, data processing system 1102 may consist merely of one or more ASICs. Hence, features of the present invention described above may be implemented in hardware and/or software. Additionally, as incorporated by reference above, there are various aspects of the invention that are carried out using computer readable instructions for performing particular tasks. These instructions can likewise be stored and processed using computer 1100.

According to other aspects of the invention, the instrument also includes a system controller, e.g., main controller 130 shown in FIG. 1A or system controller 250 shown in FIG. 1B, that coordinates the various devices and functions. The system controller may be encompassed in the computer 1100 shown in FIG. 37, or it may be a separate computer-implemented controller that may be in communication with the computer 1100. Various controllers have been described in detail above. Additionally, the patents, published applications, and applications incorporated by reference herein contain disclosures of system controllers. For example, the system controller of the present invention may have three main parts, the embedded controller, the PXI rack, and rack-mount plug-in function cards. An example of an embedded controller is the National Instruments PXI-8110

Intel quad core Personal Computer (PC) based platform, running Windows XP OS and Labview Version 8 programming language. An example rack is PXI-1044 open PXI 14 slot chassis. Plug-in function cards may be used for analog to digital conversions, digital to analog conversion, and digital I/O and can include PXI-6289 National Instruments plug-in cards. The system controller of the present invention can also utilize, for example, PXI/8430 cards to interface with serial controllers (pressure/pumps and robots). Although specific components are provided herein in describing an exemplary system controller, one of skill in the art will recognize substitute and analogous components which may be utilized in a system controller in accordance with the present invention.

Aspects of the invention are implemented via control and computing hardware components, user-created software, data input components, and data output components. Hardware components include computing and control modules, such as main controller 130, such as microprocessors, computers, and/or ASICs (e.g., computer 1100), configured to effect computational and/or control steps by receiving one or more input values, executing one or more algorithms stored on non-transitory machine-readable media (e.g., software) that provide instruction for manipulating or otherwise acting on the input values, and output one or more output values. Such outputs may be displayed, for example on display device 132, or otherwise indicated to a user for providing information to the user, for example information as to the status of the instrument or a process being performed thereby, or such outputs may comprise inputs to other processes and/or control algorithms. Data input components comprise elements by which data is input for use by the control and computing hardware components. Such data inputs may comprise positions sensors and motor encoders, as well as manual input elements via user input device 134, such as one or more of a key board, computer mouse, touch screen, microphone, switch, manually-operated scanner, etc. Data output components may comprises hard drives or other storage media, monitors, printers, indicator lights, or audible signal elements (e.g., buzzer, horn, bell, etc). Software comprises instructions stored on non-transitory computer-readable media which, when executed by the control and computing hardware, cause the control and computing hardware to perform one or more automated or semi-automated processes.

The present invention has the capability of rapidly processing very small aliquots of a nucleic acid sample solution and then subsequently running another assay on another small aliquot from the same sample. A lengthy sequence of different assays may be run. Additionally, a benefit of the present invention is that the parameters of the subsequent tests may be changed, either at the user's discretion, or in the course of a programmed script, or alternatively as a result of a decision process performed automatically by the machine. The instrument has the flexibility to rapidly mix numerous combinations of reagents and deliver them to a disposable cartridge, where the nucleic acid target is rapidly amplified and analyzed.

Furthermore, an instrument embodying aspects of the present invention can be configured, implemented, and/or used in association with systems, methods, and/or apparatus for performing thermal melt analysis on a continuously flowing fluid stream, as described in U.S. Patent Application Publication No. 2007/0231799 entitled "Method And Apparatus For Applying Continuous Flow And Uniform Temperature To Generate Thermal Melting Curves In A Microfluidic Device" and U.S. Patent Application Publication No. 2009/0318306, entitled "System And Method For Temperature Referencing For Melt Curve Data Collection," the disclosures of which are hereby incorporated by reference.

Furthermore, an instrument embodying aspects of the present invention can be configured, implemented, and/or used in association with systems, methods, and/or apparatus for performing PCR analysis on a continuously flowing fluid stream by real-time amplification and analysis of a sample of DNA within a micro-channel, as described in U.S. Patent Application Publication No. 2008/0176230, entitled "Systems And Methods For Real-Time PCR," the disclosure of which is hereby incorporated by reference.

Furthermore, an instrument embodying aspects of the present invention can be configured, implemented, and/or used in association with systems, methods, and/or apparatus for performing real time PCR in micro-channels by continuously moving boluses of test solution separated by carrier fluid through the micro-channels and performing a process, such as PCR, on each bolus and measuring signals, such as fluorescent signals, at different locations along a defined section of the channel, as described in U.S. Pat. No. 7,629,124, entitled "Real-Time PCR In Micro-Channels," the disclosure of which is hereby incorporated by reference.

Furthermore, an instrument embodying aspects of the present invention can be configured, implemented, and/or used in association with systems, methods, and/or apparatus for monitoring the amplification of DNA molecules and the dissociation behavior of the DNA molecules including the use of sensors for monitoring reactions within microfluidic channels, as described in U.S. Pat. No. 7,593,560, entitled "Systems And Methods For Monitoring The Amplification And Dissociation Behavior Of DNA Molecules," the disclosure of which is hereby incorporated by reference. The sensor has a defined pixel array for collecting image data, and image data from a select window of pixels (a sub-set of the entire array) which encompasses a portion of interest of a micro-channel is processed and stored for each of the micro-channels.

Furthermore, an instrument embodying aspects of the present invention can be configured, implemented, and/or used in association with systems, methods, and/or apparatus for monitoring the amplification of DNA molecules and the dissociation behavior of the DNA molecules, as described in U.S. Patent Application Publication No. 2008/0003593, entitled "System And Methods For Monitoring The Amplification And Dissociation Behavior Of DNA Molecules," the disclosure of which is hereby incorporated by reference. A method described includes the steps of: forcing a sample of a solution containing real-time PCR reagents to move though a channel; and, while the sample is moving through an analysis region of the channel, performing the steps of: (a) cycling the temperature of the sample until the occurrence of a predetermined event; (b) after performing step (a), causing the sample's temperature to gradually increase from a first temperature to a second temperature; and (c) while the step of gradually increasing the sample's temperature is performed, using an image sensor to monitor emissions from the sample.

Furthermore, an instrument embodying aspects of the present invention can be configured, implemented, and/or used in association with systems, methods, and/or apparatus employing continuous flow multiplex assays in which results are converted to digital format so that multiple assays can be run on each of multiple patient samples, thereby permitting high levels of multiplexing and flexibility, as described in U.S. Patent Application Publication No. 2009/0143233, entitled "Device And Method For Digital Multiplex PCR Assays," the disclosure of which is hereby incorporated by reference. A stream of sample material is introduced into each microchannel and alternating boluses of assay-specific reagents and buffer are introduced into the stream to form sequentially configured test boluses. A PCR procedure is performed on the test boluses followed by a thermal melt procedure. During the thermal melt procedure, fluorescent output is detected and fluorescence vs temperature data is collected and compared to expected normal correlations. The results, positive or negative, are converted to digital format, with positive results designated as "1" and negative results designated as "0", or vice versa.

The following applications and publications, the respective disclosures of which are hereby incorporated by reference in their entirety, provide additional details of computations and algorithms for analysis of data which may be used in connection with embodiments disclosed herein.

For example, an instrument embodying aspects of the present invention can be configured, implemented, and/or used in association with systems, methods, and/or apparatus for the analysis of denaturation data of nucleic acids as described in U.S. Patent Application Publication No. 2009/0112484, entitled "High-Resolution Melting Analysis," the disclosure of which is hereby incorporated by reference. A nucleic acid in a biological sample including at least one unknown nucleic acid is identified by fitting denaturation data, including measurements of a quantifiable physical change of the sample at a plurality of independent sample property points, to a function to determine an intrinsic physical value and to obtain an estimated physical change function, and identifying the nucleic acid in the biological sample by comparing the intrinsic physical value for at least one unknown nucleic acid to an intrinsic physical value for a known nucleic acid.

Furthermore, an instrument embodying aspects of the present invention can be configured, implemented, and/or used in association with systems, methods, and/or apparatus for genotyping and analyzing sequences of nucleic acids as described in U.S. Patent Application Publication No. 2011-0010103, entitled "Rapid Method Of Pattern Recognition, Machine Learning, And Automated Genotype Classification Through Correlation Analysis Of Dynamic Signals," the disclosure of which is hereby incorporated by reference. The publication describes methods and systems for determining whether a genotype is present in a biological sample. Steps include generating a dynamic profile an unknown genotype, correlating the dynamic profile to an average profile for a known genotype to generate a correlation value, and determining whether the correlation value falls within an acceptable threshold to determine if the unknown genotype is the known genotype. The publication also describes methods and systems for generating a training set to allow a machine to recognize a known genotype from within a class of known genotypes. Steps include generating dynamic profiles of a known genotype, averaging the dynamic profiles to generate an average profile for the genotype, and correlating the dynamic profiles of the genotype with an average profile for each known genotype in a class of genotypes to generate a correlation vector. The training set generated by these methods and systems may be used to assist in identification of unknown genotypes.

Furthermore, an instrument embodying aspects of the present invention can be configured, implemented, and/or used in association with systems, methods, and/or apparatus for analyzing denaturation data of nucleic acids as described in U.S. Patent Application Publication No. 2009/0112481, entitled "High-Resolution Melting Analysis," the disclosure of which is hereby incorporated by reference. The publication describes methods and systems for the analysis of the dissociation behavior of nucleic acids and the identification of nucleic acids. Methods and systems are described for resolving a denaturation curve of a sample containing a first and second nucleic acid into a resolved denaturation curve for the first nucleic acid and a resolved denuration curve for the second nucleic acid Embodiments of the present invention have been fully described above with reference to the drawing figures. While the present invention has been described and shown in considerable detail with reference to certain illustrative embodiments, including various combinations and sub-combinations of features, those skilled in the art will readily appreciate other embodiments and variations and modifications thereof as encompassed within the scope of the present invention. Moreover, the descriptions of such embodiments, combinations, and sub-combinations is not intended to convey that the inventions requires features or combinations of features other than those expressly recited in the claims. Accordingly, the present invention is deemed to include all modifications and variations encompassed within the spirit and scope of the following appended claims.

We claim:

1. A system for serial processing of nucleic acid assays, comprising:

a microfluidic cartridge comprising an interface chip having at least one inlet port and microfluidic channel and a separate reaction chip coupled to the interface chip, the reaction chip having at least one microfluidic channel ending in a T-junction, the T-junction in fluid communication with an associated microfluidic channel of the interface chip;

a flow control module comprising a first pumping system configured to selectively apply pneumatic pressures to the at least one microfluidic channel of the interface chip and a second pumping system to apply a pneumatic pressure to control assay fluid flow through the reaction chip;

the flow control module being configured to:
   (a) draw a first fluid into the microfluidic channel of the interface chip via the inlet port of the interface chip and stop the first fluid in the interface chip when the T-junction is loaded with the first fluid;
   (b) create a first fluid segment in the microfluidic channel of the reaction chip by drawing the first fluid from the associated microfluidic channel of the interface chip into the microfluidic channel of the reaction chip;
   (c) draw a second fluid into the microfluidic channel of the interface chip via the inlet port of the interface chip while maintaining the position of the first fluid segment in the reaction chip and stop the second fluid in the interface chip when the T-junction is loaded with the second fluid; and
   (d) create a second fluid segment in the microfluidic channel of the reaction chip by drawing the second fluid from the associated microfluidic channel of the interface chip into the microfluidic channel of the reaction chip;

a temperature measurement and control system configured to control and measure a temperature of one or more portions of the at least one microfluidic channel of the reaction chip; and a fluorescence imaging system comprising one or more illumination elements and an imaging sensor and configured to create images of fluorescent emissions from materials within the at least one microfluidic channel of the reaction chip.

2. The system of claim 1, wherein
the imaging sensor is configured to generate a storable image of at least a portion of the microfluidic channel of the reaction chip; and
a plurality of illumination elements are disposed with respect to the imaging sensor and configured to illuminate a portion of the reaction chip to be imaged by the sensor element.

3. The system of claim 2, wherein at least one of the illumination elements comprises an illumination assembly comprising:
an LED;
a mask disposed in front of the LED and having an opening formed therein so as to control an area illuminated by the illumination assembly;
a filter along an optic path of the illumination assembly for controlling the spectral content of light emitted by the illumination assembly, and
a lens for imaging an area with light emitted by the illumination assembly,
wherein the LED, the mask, the filter, and the lens are aligned along an optic axis of the illumination assembly.

4. The system of claim 2, wherein at least two of the illumination elements are configured to illuminate different portions of the reaction chip.

5. The system of claim 2, wherein the imaging sensor comprises a digital single lens reflex camera.

6. The system of claim 2, wherein each of the illumination elements comprises an LED.

7. The system of claim 2, wherein the fluorescence imaging system comprises four illumination elements disposed at 90-degree angular increments about the imaging sensor.

8. The system of claim 2, wherein the imaging sensor comprises a CMOS sensor.

9. The system of claim 2, wherein said imaging sensor includes a pixel array, and wherein an image of only a portion of the pixels of the pixel array is detected.

10. The system of claim 2, wherein said imaging sensor is configured to generate multiple images.

11. The system of claim 2, wherein said imaging sensor is configured to generate an image having a JPEG format.

12. The system of claim 2, wherein the fluorescence imaging system comprises at least one extension tube between the imaging sensor and the microfluidic channel of the reaction chip.

13. The system of claim 2, wherein the fluorescence imaging system further comprises an emission filter positioned between the imaging sensor and the microfluidic channel of the reaction chip and configured to allow light signals of only a selected wavelength to reach the sensor.

14. The system of claim 7, wherein the microfluidic channel of the reaction chip comprises a first zone and a second zone, and wherein a first LED is positioned and oriented to illuminate the second zone; a second and a third LEDs are spaced 180-degrees from each other and are disposed on opposed sides of the sensor and are positioned and oriented to illuminate the first zone; and a fourth LED is positioned and oriented to illuminate both the first zone and the second zone.

15. The system of claim 1, further comprising a liquid handling system comprising at least one pipettor configured to be accessible to the inlet port of the interface chip and configured to aspirate reagent fluids, mix the reagent fluids, and dispense a mixture of reagent fluids to the inlet port of the interface chip.

16. The system of claim 15, wherein the pipettor is configured to
(a) draw a first volume of a first fluid into the pipettor;
(b) draw a second volume of a second fluid into the pipettor;
(c) expel a droplet including the first and second fluids from the pipettor without releasing the droplet from the pipettor, wherein a volume of the droplet is greater than half the sum of the first and second volumes;
(d) draw the droplet back into the pipettor; and
(e) repeat steps (c) and (d) at least one time before dispensing a mixture of the first and second fluids to the inlet port of the interface chip.

17. The system of claim 15, wherein the pipettor includes at least one pipette tip having a docking feature configured to facilitate automatic alignment of the pipette tip with the inlet port of the interface chip.

18. The system of claim 17, wherein the inlet port of the interface chip includes a docking receptacle configured for cooperative engagement with the docking feature of the pipette tip to align the pipette tip with the inlet port.

19. The system of claim 18, wherein the pipettor is configured to
engage the docking feature of the pipette tip containing the fluid mixture with the docking receptacle of the inlet port of the interface chip;
produce a bead of the fluid mixture that makes contact with the microfluidic channel of the interface chip while the first pumping system pulls at least a portion of the fluid in the bead into the microfluidic channel of the interface chip, wherein the docking feature and the docking receptacle are configured to position the pipette tip with respect to the inlet port such that the proximity of the pipette tip and the microfluidic channel allows a portion of the bead to contact the microfluidic channel while remaining attached to the pipette tip; and
disengage the docking feature of the pipette tip from the docking receptacle of the inlet port of the interface chip while removing the bead from contact with the microfluidic channel of the interface chip, leaving fluid only inside the microfluidic channel and not in the inlet port of the interface chip.

20. The system of claim 15, wherein the interface chip includes a plurality of inlet ports and a microfluidic channel associated with each inlet port and the reaction chip includes a plurality of microfluidic channels, each in fluid communication with an associated microfluidic channel of the interface chip, and wherein the pipettor is configured to simultaneously dispense a mixture of reagent fluids to two or more of the inlet ports of the interface chip.

21. The system of claim 1, further comprising a system controller in communication with the flow control module comprising the first and second pumping systems, the temperature measurement and control system; and the fluorescence imaging system and configured transmit control signals to control operation of the flow control module, the temperature measurement and control system; and the fluorescence imaging system.

22. The system of claim 1, wherein the flow control module is configured to draw the first fluid into the microfluidic channel of the interface chip via the inlet port of the interface chip by setting a negative pressure at a vent well of the interface chip.

* * * * *